United States Patent
Delgado-Escueta et al.

(10) Patent No.: US 9,220,697 B2
(45) Date of Patent: *Dec. 29, 2015

(54) COMPOSITIONS AND METHODS FOR DIAGNOSIS AND TREATMENT OF EPILEPSY

(76) Inventors: Antonio V. Delgado-Escueta, Malibu, CA (US); Kazuhiro Yamakawa, Saitama (JP); Toshimitsu Suzuki, Saitama (JP); Marco Tulio Medina-Hernandez, Tegucigalpa (HN); Maria Elisa Alonso Vilatela, Delegacion (MX)

(*) Notice: Subject to any disclaimer, the term of this patent is extended or adjusted under 35 U.S.C. 154(b) by 0 days.

This patent is subject to a terminal disclaimer.

(21) Appl. No.: 12/914,844

(22) Filed: Oct. 28, 2010

(65) Prior Publication Data

US 2011/0287418 A1     Nov. 24, 2011

Related U.S. Application Data

(63) Continuation of application No. 11/572,201, filed as application No. PCT/US2005/025093 on Jul. 15, 2005, now Pat. No. 7,829,279.

(60) Provisional application No. 60/588,769, filed on Jul. 16, 2004.

(51) Int. Cl.
| | |
|---|---|
| *C07H 21/04* | (2006.01) |
| *C12Q 1/68* | (2006.01) |
| *A61K 31/19* | (2006.01) |
| *C07K 16/18* | (2006.01) |

(52) U.S. Cl.
CPC ............ *A61K 31/19* (2013.01); *C07K 16/18* (2013.01)

(58) Field of Classification Search
None
See application file for complete search history.

(56) References Cited

U.S. PATENT DOCUMENTS

| 7,563,567 B1 | 7/2009 | Huang et al. | |
|---|---|---|---|
| 2007/0105122 A1* | 5/2007 | Ota et al. | 435/6 |

FOREIGN PATENT DOCUMENTS

| EP | 1074617 A2 | 2/2001 |
|---|---|---|
| JP | 2002191363 A | 7/2002 |

OTHER PUBLICATIONS

Lucentini (The Scientist; 2004, vol. 24, p. 20).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Gu et al (Epilepsy Research, vol. 66, p. 91-98, 2005).*
Pinto et al. (Epilepsia, vol. 47, No. 10, pp. 1743-1746, 2006).*
Ma et al. (Epilepsy Research, vol. 71, pp. 129-134, 2006).*
Stogman et al. (Neurology, vol. 67, pp. 2029-2031, 2006).*
Bai et al. (Epilepsia, vol. 50, No. 5, pp. 1184-1190, 2009).*
Buyuk et al. (Journal of Medical Sciences, vol. 32, No. 5, 2012).*
Bittigau et al., "Antiepileptic Drugs and Apoptosis in the Developing Brain," Ann. n. Y. Acad. Sci., 2003, 993, 103-114, Abstract only.
Delgado-Escueta et al., "An Update on the Genetics of Juvenile Myoclonic Epilepsy," Epilespia, 2003, 44, Suppl 8, p. 21.
Medina, M.T. et al., "Childhood Absence Epilepsy Evolving to Juvenile Myoclonic Epilepsy: Electroclinical and Genetic Features," Myoclonic Epilepsies of Infancy and Childhood, Jun. 11, 2004, pp. 195-214.
Naffas-Mazzacaratti et al., "Growth-associated phosphoprotein expression is increased in the supragranular regions of the dentate gyrus following pilocarpine-induced seizures in rats," Neuroscience, 1999, 91(2), 485-492, Abstract only.
Sakhi et al., "p53 induction is associated with neuronal damage in the central nervous system," PNAS, 1994, 91, 7525-7529.
Suzuki, T. et al., "Mutations in EFHC1 Cause Juvenile Myoclonic Epilepsy," Nature Genetics, Aug. 2004, pp. 1-8, vol. 36, No. 8.

* cited by examiner

*Primary Examiner* — Jeanine A Goldberg
(74) *Attorney, Agent, or Firm* — Karen S. Canady; canady + lortz LLP

(57) ABSTRACT

Compositions and methods for diagnosis or treatment of epilepsy disease with EFHC1, EFHC1 agonists, or EFHC1 analogs are provided. Compositions and methods for diagnosis or treatment of epilepsy disease with EFHC1*a*, EFHC1*a* agonists, or EFHC1*a* analogs are provided.

5 Claims, 27 Drawing Sheets

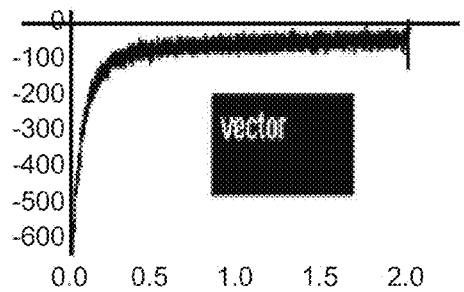
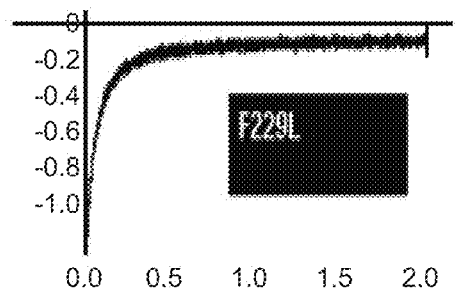
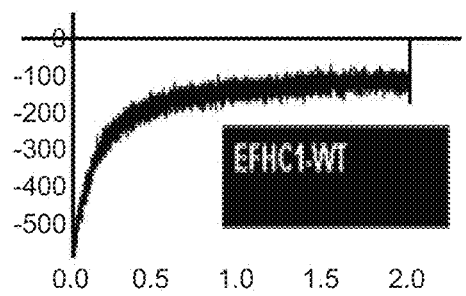
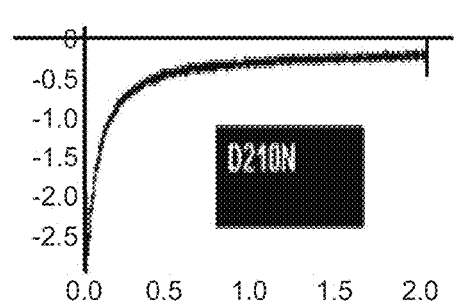
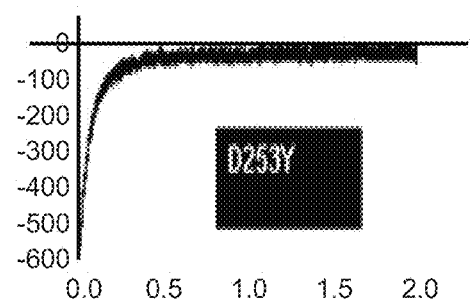
Figure 8

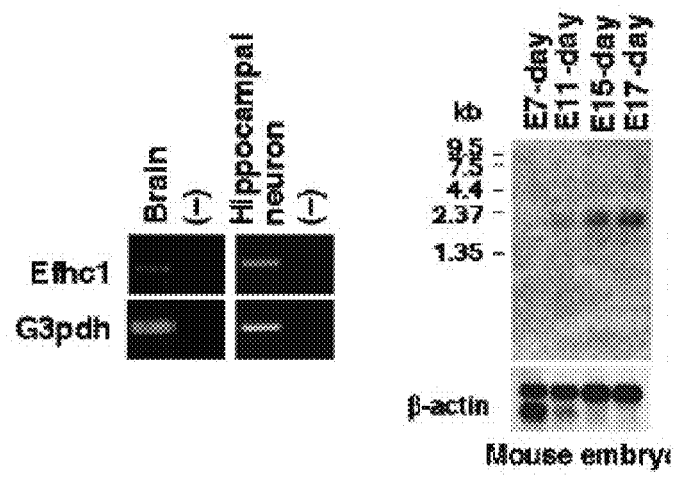
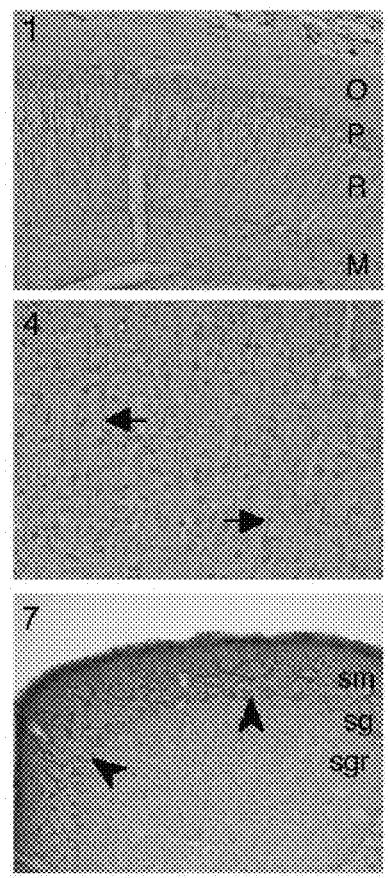
Figure 13

```
   1 gggggccaaa caacacggcc gggaggcggc cgctgcctgc cgggccctct cttctgggac
  61 cctggatttt cggacactga gcgccatggc cctgcctctg ctgccgggca acagcttcaa
 121 ccgcaacgtg ggaaggaga agtttcacaa atcccaacat tggggctttt gcaacaatgt
 181 tatgatgttg gtgagtgatg aaaagcctgg aataggtgga gaaccacttc tggggcaaaa
 241 gataaagcct aaatgtagca tatatcctaa aggagatgga agtgatgtac catcatgggt
 301 agcctttgat aaacaggtat tatcttttga tgcctatttg gaagaggaag tacttgataa
 361 aagccaaacc aactacagaa taagatacta taaaatctac ttctaccctg aagatgacac
 421 aattcaagta aatgaacaag aggtgaaaaa tagtggatta cttcaaggga cttctatccg
 481 ggtcatcgg attactcttc cgcctcctga tgaggatcag ttttatactg tgtatcattt
 541 taatgtcggc acagaggttg tcttctatgg ccggacattc aagatttatg actgtgatgc
 601 attcaccaga aactttttga ggaaaatagg ggtcaaagtg aatccccag tgcaatgtcc
 661 agaagatcct tacatgaaga ttcggagaa ggttgtagaa cacgtagagc ccttacgtcc
 721 ctacgaatcc ctcgacaccc tgaaacagtt cctccagtat catggcaaga ttttgtgttt
 781 cttctgcctg tgggatgact cagtctcaat gtttggagac cgtagagaac tcatcctgca
 841 ttacttcttg tgtgatgata ctattgaaat caaagaattg cttccacaca gtcaggccg
 901 agatgctcta aaaatgttcc tccggaggag taagctaccc aagaattgcc cacctagagt
 961 ctatcaaccca ggccagataa cagatcgagc agttctcaat tcatatgctg acttatataa
1021 gaaccaagcg gatggctacc tgttcgatag atataagcta ggaaaagtag accaagagtt
1081 ttacaaagat agtgaccctg ccctaggagt cacccatcaa gtgtggggaa gaaaagtgct
1141 cctttatgac tgtgatgaat ttacgaagtc ttattataag tctaaatatg gaattgagaa
1201 cttcacctca gtttcatgca agcctccttc tcctcctcca aaaatagaaa ggaaatttcc
1261 accttacaac ggttttggtt ctgaagagga ttctctccgt aactgcatag acctcaagcc
1321 cacacctcat cggaggaact tcagaagtt tatggaaaaa gacagctatg gtccaaaag
1381 caatatacct cgttttttg caaaactagt cacagacaaa tgtgttgact tggacaggat
1441 gtttgttatc tcatattatc tcggtcgatga caccattcca gtgtttgaac ctatagagag
1501 gaattcagga attgctggtg ggatgttctt gaaaagaagt cgcgttaaga agcctggaca
1561 agaagtcttt aaaagtgaac tatctcaata tatcaaggcc gaggagctgt acattggagt
1621 cacggtgaat gtgaatggtt acctatttcg ttgctcaat gctgatgagt atacttaaa
1681 ctacatggag caaaatacag ataagtatcc tttcagtaac ctcaaacttg ccctacaaaa
1741 gctgaagcaa gaagaggaa aatccagaga gctcaagcag gtatttaaag ctgatgactc
1801 taagcacaca aatatggtgg attataatac attcagacac atattgatgt ctttgactgt
1861 tggaaacctt gtgagcaag aatttgtaac cattgcacgt cactaccgtg tgcctgaggg
1921 cacatgttca gatatggatt tcttaatcgc actggcccac gaaaagttca agaaaaatat
1981 gtttgagaat ttcgacactt tcatttattc ctgtgtgtat gaagatcgag aaaaaaaaa
2041 tgtattaccc accaaagaca ttaaaggct gtgcaaatcc tccagattac ctttgagtga
2101 tgatcttcta gaatcctat tgtcaaggct tgaagacagt gaaaaacaaa tagattataa
2161 gtcatttttc tctgccctga actggagaaa gaatccagtg cctgaattgc aaccagcatc
2221 atacctaaa gagagatgt aagatgtttg gcttggtatg ccatcaccta ttcctgcgaa
2281 atacattgac tactggacct ttttgaagga cgcgtttggc ttagaggagg aataaccatg
2341 ccagttttgg tcaattctct atgatttact tctctcattt tgccacattt acttttagtag
2401 atataatttc attaaaaaca aaaagaaac aaggtttata ttaaatggaa atccataaac
2461 cacaaaaaaa aaaaaaaaa aaaaaaaaa aaaaaaaaa aaaaaaaaa a
```

Human cDNA (FLJ22843); NCBI accession number NM_025184

Human cDNA (FLJ22843): SEQ ID NO: 1

Figure 16

```
  1 malpllpqns fnrnvgkekf hksqhwgfcn nvmmlvsdek pgiggepllg qklkpkcsly
 61 pkgdgsdvps wvafdkqvls fdaylseevl dksqtnyrlr yyklyfyped dtlqvnepev
121 knsqllqgts irrhritlpp pdedqfytvy hfnvgtevvf ygrtfklydc dsftrnflrk
181 lgvkvnppvq cpedpymklr revvebvepl rpyesldtlk qflqyhgkll cffclwddsv
241 smfgdrreli lhyflcsdti elkellphss grdalkmflr rsklpkncpp rvyqpgqltd
301 ravlnsygdf lknqedgylf drykiqkvdq sfykdsdlsl gvtlnvwgrk vllydcdeft
361 ksyykakygl snftsvsckp psppplkierk fppyngfgse sdslrncldl kptphrrnfk
421 kfmekdsygs ksnllrffak lvtdkcvdld rmfvlsyylg ddtlsvfepi ernsqlaggm
481 flkrsrvkkp gqqvfksels eyikaeelyl qvtvnvngyl frllnsdeyt lnymeqntdk
541 ypfsniklel qklkqssegks relkqvfkas dskhtnmvdy ntfrdllmsl tvgnlseqsf
601 vtlarhyrvp egtcsdmdfl lalahekfkk nmfenfdtfl ysevyedrek knvlptkdlk
661 rlckssrlpl sddlleslls rfedsekqld yksffsalnw rknpvpelqp asylkerced
721 vwlgmpspip akyldywtfl kdafglese
```

Human polypeptide (FLJ22843); NCBI accession number NP_079460

Human polypeptide (FLJ22843); SEQ ID NO: 2

Figure 17

```
Mouse   (AK006489) MGTNPVHGLPFLPGSSFTDST-KTAPHRSQTLNYRN-GYAVVRRPTMGIGGDRLHYNQLS 58
HuEFHC1 (AK001328) MVSNPVHGLPFLPGTSPKDST-KTAPHRSQTLSYRN-GYAIVRRPTVGIGGDRLQFNQLS 58
Human   (FLJ22843) ------MALPLLPGNSFNRRVGKEKPHKSQHWGFCNNVMMLVSDEKPGIGGEPLLG---- 50
                         .**;***.**.  .. * **;*** ;:  *   ;*   . ****;: *

Mouse              QAELDKLANKAPILTYGPLKQAPLAKFVPAHVAFDKKVLKFSAYFQEDVPISMEEHYRIR 118
HuEFHC1            QAELDKLASKAPVLTYGQPKQAPPADFIPAHVAFDKKVLKFDAYFQEDVPMSTEEQYRIR 118
FLJ22843           ----QKIKPKCSIYPKGD------GSDVPSWVAFDKQVLSPDAYLEEEVLDKSQTNYRIR 106
                       *,.:. *      ..  *;  *****:**.*.**::*:*   . : :****

Mouse              HVNIYYLEDDSMSVIEPVVENSGIPQGKLIKRQRFTKN--DMGDHYHWKDLNEGINLTV 176
HuEFHC1            QVNIYYLEDDSMSVIEPVVENSGILQGKLIKRQRLAKN--DRGDHYHWKDLNEGINITI 176
FLJ22843           YYKIYFYPEDDTIQVNEPEVKNSGLLQGTSIRRHRITLPPPDEDQFYTVYHFNVGTEVVF 160
                    ;**:* ***:;;.**  *;**** **. *::*: :   *  .:.*  :*  * :;.

Mouse              YGKTFRIVDCDRPTQDFLESQGIELNPSEKIPLDPYTQLRKEPVRKYVTP---SDFDQLK 233
HuEFHC1            YGKTFRVVDCDQPTQVFLESQGIELNPPEKMALDPYTELRKQPLRKYVTP---SDFDQLK 233
FLJ22843           YGRTFKIYDCDAFTRNFLRKIGVKVNPFVQCPEDPYMKIRREVVSRVEPLRPYESLDFLK 220
                   **;**;:: ***  **;. *;:**.   **  :*::  ;.;        ..:* **

Mouse              QFLTFDKQVLRPYAIWDDTDSLFGECRHYIIHYYLMDDTVRIREVHKRMNGRDPPPLLMN 293
HuEFHC1            QFLTFDKQVLRPYAIWDDTDSMYGECRTYIIHYYLMDDTVRIREVHERNDGRDPPPLLMN 293
FLJ22843           QFLQYRGKILCPFCLWDDSVSMFGDPRELILHYFLCDDTIRIKELLPHSSGRDALKMFLR 280
                   ***  :. ::*  * *;:****; *;;*; * ; *;**;* ***;***;*   ,.***.; *::

Mouse              RQRMPKVLVENAKN-----------PPKCVLEISD---------QEVLEWYTAKDFIV 331
HuEFHC1            RQRVPKVLVENAKN-----------FPQCVLEISD---------QEVLEWYTAKDFIV 331
FLJ22843           RSKLPRNCPPRVYQPGQITDRAVLNSYGDFIKNQADGYLFDRYKLGRVDQEFYRDSDLSL 340
                   *.;:**    , ;  :       ;  .  : :  *      ;     *;:* .**  :

Mouse              GKPLTILGRTFPIYDCDPFTRQFYKDKPGMPDLPPVDVTKKEPPP-VKQELPPYNGYGLI 390
HuEFHC1            GKSLTILGRTFPIYDCDPFTRRYYKEKPGITDLPRIDVSKREPPP-VKQELPPYNGFGLV 390
FLJ22843           GVTINVWGRKVLLYDCDSFTKSYYKSKYGIERFTSVGCKPPSPPPKIERKPPPYNGFGSE 400
                   *  ;.;; **,.:;.:****  **; :**,*::*; ::      ;.*** :::;:*****;*

Mouse              EDSAQNCFALIPKAPRKDVVKMLMND----NKVLRYLAALESPIPEDKDRRFVFSYFLA 445
HuEFHC1            EDSAQNCFTLIPKAPRKDVIRMLVND----NKVLRYLAVLESPIPEDKDRRFVFSYFLA 445
FLJ22843           EDSLRNCIDLKPTPHRRNFKRFMEKDSYGSKSNILRPFAKLVTDKCVDLDRMFVISYYLG 460
                   ***  :***;  * *..  :;::.  **:; :*         .;;:**;;* *  ;   * ** **;**;*.

Mouse              TDMISIFEPPVRNSGIIGGKFLGRTKVVKSFSPVDN---PIYYSPSDFPIGAVIEVPGHR 502
HuEFHC1            TDMISIFEPPVRNSGIIGGKYLGRTKVVKPYSTVDN---PVYYGPSDFPIGAVIEVPGHR 502
FLJ22843           DDTISVFEPIERNSGIAGGMFLKRSRVKKPGQEVFKSELSEYIKAEELYIGVTVNVNGYL 520
                   *  **;***  ***** ** ;* *;;:* *,.  *  .  *  ..;;**..;;* *;

Mouse              FVILDTDEYVLKYMESNASQYSPRALASIQNRIQKPELPAPELESKQATGEPMVQ----- 557
HuEFHC1            FILLDTDEYTLKYMESNAAQYSPRALASIQMHVREKREAPAPEAESKQTE---------- 551
FLJ22843           FRLLWADEYTLNYMSQNTDKYPFSNLKLALQGRLKQESGKSRELKQVFKAADSKHTNMVDY 580
                   *  ;*;;*** **;*** *;  ;  ,  *       :::;; *  ; * *

Mouse              ---------------------------GTEESKVQDLDALIDQIRMHLRNYSYR--BNLR 588
HuEFHC1            ---------------------------KDPGVQELEALIDTIQKQLRDHSCX--DNIR 580
FLJ22843           NTFRDILMSLTVGMLAEQEFVTIARHYRVPSGTCSDMDFLIALAHEKFKKMMFENPDTFI 640
                                              ;  .;;:**    *   ; ;:*   :   ;   ; .:
```

Figure 18A

```
Mouse      STFQMYDKDESGYVDRETFFKICETLNVPVDDSLIKELTRLCTHGEGRIBYYNFVRAFSN 648
HuEFHC1    RAFQIYDKEASGYVDRDMFFKICESLNVPVDDSLVKELIRMCSHGEGKINYYNFVRAFSN 640
FLJ22843   YSCVYEDREKKNVLPTKDIKRLCKSSRLPLSDDLLESLLSRFEDSEKQIDYKSFFSALNW 700
              *::  :  :  :  ::*::  :*:*.*:*:.*:     .* :*:* .*. *:.

Mouse      ------------------------------------------------------------
HuEFHC1    -----------------------------------------------------------
FLJ22843   RNNPVPELQPASYLKERCEDVWLGMPSPIEAKYIDYWTPLKDAFGLEEE 749
```

Mouse (AK006489): SEQ ID NO: 5

Human EFHC1 polypeptide (AK001328; NM_018100): SEQ ID NO: 4

Human (FLJ22843): SEQ ID NO: 2

Figure 18B

```
Dros CG8959     MLRIPGMFLLPGTLFRD-VSKGHYPKPQSLANVQGLSMLSDRQQPAPVESGSVTVDISCP  59
Dros CG11048    MMRLPGMFMLPGAQFYD-RGKRSHPRQQTLSSYQGIQMLSDRRSPELVEPNGIVADPKCP  59
Human (FLJ22843) -----MALPLLPGNSFNRNVGKEKFHKSQRMGFCNNVMMLVSDEKP-------GIGGEPLLG  50
                       :*:***  *  :  :  *     :: ** *    :*:      :  :

CG8959      PVGAS--SIYPPRSGPRMPPWLAYDKKVLCFHAYFKQTLQEVYHAPYLVRKVKIYYYLED  117
CG11048     PVPAQLNSLMAPKATTKLPPWLAYDKQVLCFNAYFKENLTEIYHAPYQVRKVKIFFYLED  119
FLJ22843    QKIKFKCSIYFRGDGSOVPSHVAFDRQVLSFDAYLEEEVLDKSQTHYRIRYYKIYFYPED  110
                 *:: : :* *:*:;**:.*:**::: : :: *  :* :* **;:**  **

CG8959      GTLEIYEPRVDNSGIVQGCVVHRQRVQKAPPCDNEFMSLIDLNVDQTVQIFDRQYHITDC  177
CG11048     GTMQVTEPKVENSGIPQGCLVHRQRIPKAPPTOREFISIFDLNVDTDVQIFDRVYHISGC  179
FLJ22843    DTIQVNEPEVKNSGLLQGTSIRRSHRITLPPPDEDQFYTVVRFNVGTEVVFYGRTFKIEDC  170
             .*::: **.*.***: ** :;*:*::. .**:   *  *:.* ::* .*

CG8959      DPFTRTFLEKRGITVPOPVKSPCDPTEEQRKRESQPRSGN----LIPKNHPFAQFLKYDR  233
CG11048     QVPFRQEFLNPAGIFVPEAQQEPCDPTTEIRKRSGLKQTGNTATSALPKHHAFAQFLEFDR  239
FLJ22843    DAFTRNELRKIGVRVNPPVQCPEDFYMRIRREVVEHVEPLR---PYESLDTLKQFLQYHG  227
              * *** **.:. *: *  :  * **  : *::         . ..:  ***::.

CG8959      QILKFQAYWED-RTEFGDVRKLELCYYLSDDTIEIKEQHIRNSGRDSPTVFLKRGRLARE  292
CG11048     RVLKFQGYWND-RSEFGDVRKLEVCYYLADDTIDIKEKFPRNSGREGPTTYFLKRGKLFKE  298
FLJ22843    KILCFFCLWDDSVSMFGDRRELILHYFLCDDTIEIKELLPRSSGRDALKMFLRRSKLPKN  287
             :;*  *  :*;  * *** :**:*:***:** :.***:: . **:*:*.::

CG8959      FEG-LQLPGQMTPMTLLNVLGTNMRNVR--YCVDPLNTGNKEIHYYREKDLQIGSVINVY  349
CG11048     FSG-LPLPGQQTAMTLLNVLGNSMRDVR--YVADPLNTGQKEVQHYTDQDLQIGAVLNVF  355
FLJ22843    CPPRVYQPFGQITDRAVLNSYGDFIKNQADGYLFDRYKLGSKVDQEFYKDSDLSLGVTINVM  347
               :   ***   *  :***  *  ::: *    *  *: :   .:.**:.* ..:**:

CG8959      GRAVVITELDPFTQNYYRQRYGIQDFTPLPIPARSODCADERS---ERQLPFYNGWGSYE  406
CG11048     GRSVVLTSCDQFTQSYYREKYGIQEFSPQPIPERSSIRPYTQGGMGSRRLPFYNGWGSHE  415
FLJ22843    GRKVLLYDCDEFTKSYYKSKYGISENFTSVSCKPPS------PPFKIERKFPFYNGFGSEK  401
            ** *;:   *  **:;**;:***;:*;.       *       ,*:;*****:*  *

CG8959      GSVGNCISVEPKPPKSDFKKFIKYDRY-----VLRFGAKMLSYIKANCERIFVSYYLCD  461
CG11048     DSEGNCITVEPKPPQADFXKLFKYDGC-----ILSFGAKLISAIRDNGERDFVISYFLAD  470
FLJ22843    DSLRNCIDLRPTPRRNFXKFMEKDSYGSXSNILRFFAKLVTDKCVDLDRMFVSSYYLGD  461
             *   ***  :*:.*  :  *****:;   *      .:**  :       :** ***::*  *

CG8959      DTLQIQEIAVRNSGFLGGEFMKRTRLELPGQERFSCKQPQYYMPWNFFVGSTMSLKDFIF  521
CG11048     DTLQIYETSRRNSGFLGGEFLKRARVPLPGQDMYSSSRPEYYRANDFYIGRTMTLKDHIF  530
FLJ22843    DTISVFEPIERNSGIAGGMFLKRSRVKKFGQEVFKSELSSYIKAEELYIGVTVNVNGTLF  521
            **:.:  *  ****;: **   **; .*::*;**:. ..: *   ::;;;*  ;:::*

CG8959      HIVSADEYTLMYMERHPEIFFFRANVGVIMEKVKSALQNRMAEFVGSCVPDCTDLEKRBDV  581
CG11048     HIVSADEFTLMYMEQHPSEFFPVADIQKIMQKIREAVRPDYKQFVLRCKPDG-DLG--DYT  587
FLJ22843    RLLNADEYTLNYMEQNTDKYPFSNLKLALQKLKQEEGKSRELKQVFKACRSKHTN-----  576
             :::.****:**  ***;:.:*         ::.    :     ::.  ;:  .*

CG8959      FVSFESFKGALISIMG-NQISDHEIISLCRHFSAEKSQPNACDRSTVRAAAHLELKRTLN  640
CG11048     AVSFEILRSTLLSYLSKDCLLNHEIVTVCRFFSAEQAMPPSCDRNVRAAAQLELKRALN  647
FLJ22843    MVDYNTFR-DILMSLTVGNLAEQEFVIARHYRVPEG---TCSDMDFLIALAHEKFKNMF  633
                 *:::: : ::   :  *  *:  **:   :        . .  * *: :: *  ::

CG8959      NARDDLMEHFHHINPTNQPFLPEVKVRSALRGCRLPFSLELIDNILSILNRNECDDIEYC  700
CG11048     NGMDQLNDRLSHINPACKPYISEGQVRSTLRGCRLPFSLELVEDILMVLQRNGQNEIEVR  707
FLJ22843    ENFOTFIYSCVYEDREKKNVLPTKDIKRLCKSSRRLPLSDDLLESLLSRFEDSE~KQIDYK  692
             :  *  :  : : :   :  *: ,***::* .*;:*::*  ::  .  .*:
```

Figure 19A

```
CG8959     DLMNFIDVSCGKGCDMLPVNHAFELCPKIPF-LNKGRVVNFTCPLRELNLPLNLPAGGEK  759
CG11048    DFLAFPNMRNDQVPDIAPLNIAFELCPKLPF-LHKGRLVDFTWFLDYLGIEEELKR---A  763
FLJ22843   SFFSALNWRKNPVPELQPASYLKERCEDVWLGMPSPIPAKYIDYWTFLKDAPGLEEE---  749
             .::   ::   .    ::  * .  * * .: : :  ..:   :    *        *

CG8959     NNDAIAEGGRIMPPSAMPDTDAHKANEDDAQHMA  793
CG11048    NN-------------------------------  765
FLJ22843   ---------------------------------
```

*Drosophila* (CG8959): SEQ ID NO: 6

*Drosophila* (CG11048): SEQ ID NO: 7

Human (FLJ22843): SEQ ID NO: 2

Figure 19B

```
   1 aaaaccatg gatcctggag gtgcccgcga acactgcttg tcgcctgggc aaccggagag
  61 gacgaagcag gacctaggtg gcggcggtgg tacggctgc aatggtgtcc aatcccgtgc
 121 atggcttgcc ctttcttccg ggcacgtcct ttaaggactc tacgaaaaca gccttccaca
 181 gaagtcagac gctgagctac aggaacggct atgcaattgt tcgacgtcca acagttggga
 241 taggcggaga ccggctccag ttcaaccagc tgtcccaggc tgagctggat gagttggcca
 301 gtaaggcacc agtcttaact tatggccaac ctaaacaagc cccacctgcg gattttattc
 361 ctgcgcatgt ggcctttgac aaaaaggtac tgaaatttga tgcctatttc caagaagatg
 421 ttcctatgtc aactgaggaa cagtatagga tcgtcaggt gaacatttac tattatctag
 481 aagatgacag catgtctgtc atagagcctg ttgtagaaaa ttctggaatc cttcaaggca
 541 agttaataaa acgccagcgg ctagccaaga atgaccgggg tgaccattac cattggaaag
 601 acctaaatcg aggaataaac atcacaattt atggcaaaac tttccgcgtt gttgactgtg
 661 accaattcac acaggtattt ttagaaagcc aaggaattga gttaaatcca ccagagaaga
 721 tggctcttga tccttacact gaactccgaa aacagcctct tcgtaagtat gtcaccccat
 781 cagactttga tcaactcaag caatttctca ccttttgacaa acaggtcctt cgattctatg
 841 caatctggga tgatacagac agcatgtatg gtgaatgtcg gacctacatc attcattact
 901 atcttatgga tgatacggtg gaaattcgag aggtccacga acggaatgat gggagagatc
 961 ctttccactc cctaatgaac cgccagcgtg tgcccaaagt tttggtgaaa aatgcaaaga
1021 acttcccctca gtgtgtgcta gaatctctg accagaagt gttggaatgc tatactgcta
1081 aagacttcat tgttgggaag tcactcacta tccttgggga aacttttctc attatgatt
1141 gtgatccatt tactgacgg tattacaaag agaagtttgg aatcactgat ttaccacgta
1201 ttgatgtgag caagcgggaa ccacctccag taaaacagga gttgcctcct tataacggtt
1261 ttggactagt ggaagattct gctcagaatt gttttactct cattccaaaa gtccaaaaaa
1321 aagacgttat taaatgctg gtgaatgata acaaggtgct tgttatttg gctgtactgg
1381 aatccccat cccagaagac aaagaccgca gatttgtctc tcttacttc ctagctaccg
1441 acatgatcag tatctttgag cctcctgttc gcaattctgg tatcattggg ggcaagtacc
1501 ttggcaggac taaagttgtt aaaccatact ctacagtgga caacctgtc tactatggcc
1561 ccagtgactt cttcattggt gtgtgattg aagtgtttgg tcaccggttc atcatccttg
1621 atacagacga gtatgttttg aaatcatgg agagcaacgc tgcccagtat tcaccagaag
1681 cactcggtc aattcagaac catgtccgaa agcgagaagc gcctgctcca gaagcagaaa
1741 gcaagcaaca tgaaaaggat ccaggcgtgc aggaattgaa agcattaata gacacaattc
1801 agaagcaact gaaagatcac tcatcgcaaaag acaacattcg tgagccattt caaatttatg
1861 acaaggaagc ttcaggatat gtggacagag acatgttctt taaaatctgt gaatgctta
1921 acgtccagt ggatgactcc ttggttaagg agtaatcag gatgtgctct catggagaag
1981 gcaaaattaa ctactataac tttgttcgtg cttctcaaa ctgacctgct gatgagaaaa
2041 tgcaagacaa ttttgatac tggaactatg ctttgaaata caccttacac tcttcatagt
2101 ggc
```

NCBI Accession: AK001328; NM_018100

Human EFHC1 cDNA (AK001328; NM_018100): SEQ ID NO: 3

Figure 20

Transcript A

MVSNPVHGLPFLPGTSFKDSTKTAFHRSQTLSYRNGYAIVRRPT
VGIGGDRLQFNQLSQAELDELASKAPVLTYGQPKQAPPADFIPAHVAFDKKVLKFDAY
FQEDVPMSTEEQYRIRQVNIYYYLEDDSMSVIEPVVENSGILQGKLIKRQRLAKNDRG
DHYHWKDLNRGINITIYGKTFRVVDCDQFTQVFLESQGIELNPPEKMALDPYTELRKQ
PLFKYVTPSDFDQLKQFLTFDKQVLRFYAIWDDTDSMYGECRTYIIHYYLMDDTVEIR
EVHERNDGRDPFPLLMNRQRVPKVLVENAKNFPQCVLEISDQEVLEWYTAKDFIVGKS
LTILGRTFFIYDCDPFTRRYYKEKFGITELPRIDVSKREPPPVKQELPPYNGFGLVED
SAQNCFTLIPKAPKKDVIKMLVNDNKVLRYLAVLESPIPEDKDRRFVFSYFLATDMIS
IFEPPVRNSGIIGGKYLGRTKVVKPYSTVDNPVYYGPSDFFIGAVIEVPGHRFIILDT
DEYVLKYMESNAAQYSPEALASIQRHVRFREAPAPEAESKQTEKDPGVQELEALIDTT
QKQLKDHSCKDNIREAFQIYDKEASGYVDRDMFFKICESLNVPVDDSLVKELIRMCSH
GEGKINYYNFVRAFSN

NCBI Accession: AK001328; NM_018100.

Human EFHC1 polypeptide (AK001328; NM_018100): SEQ ID NO: 4

Figure 21

```
   1 agcgttacca tgatcctgga ggtgccgtg aacactgctt gtcgcctggg caaccggaga
  61 ggacgaagca ggacctaggt ggcgcgctg gtaccggctg caatggtgtc caatcccgtg
 121 catggcttgc cctttcttcc gggaacgtcc tttaaggact ctacgaaaac agccttccac
 181 agaagtcaga cgctgagcta caggaaggc tatgcaattg ttcgagctcc aacagttggg
 243 ataggcggag accggctcca gttcaacgaa gttgcccagg ctgagctgga tgagttggcc
 301 agtaaggcac cagtcttaac ttatgcccaa cctaaacaag ccccacctgc ggatttttatt
 361 cctgcgcatg tggcctttga caaaaaggta ctgaaattg atgcctattt ccaagaagat
 421 gttcctatgt caactgagga acagtatagg atccgtcagg tgaacattta ctattatcta
 481 gaagatgaca gcatgtctgt catagagcct gttgtagaaa attctggaat ccttcaaggc
 541 aagttaataa aacgccagcg gctagccaag aatgacgggg gtgaccatta ccattggaaa
 603 gacctaaatc gaggaataaa catcacaatt tatgcaaaa cttccgcgt tgttgactgt
 661 gaccaattca cacaggtatt ttagaaagc caaggaattg agttaaatcc accagagaag
 721 atggctcttg atccttacac tgaactccga aaccagcctc ttcgtaagta tgtcaccca
 781 tcagacttttg atcaactcaa gtaatttctc acctttgaca aacaggtaag tgacatagga
 841 accacaatag gcttacttat ttccaaatgt gacctacatt tattggcaaa aggtttgggt
 901 agctgtattg gtaactattt tgaaacatta cagctataat tgaactgttt ggacacagta
 961 ctgtctttct gttttcatca agggttacag gtacaggaat gcctacattt catatggaga
1021 tccaaagaag atcgtggagt tgccggagttg ttttgtgaac ctcaccaaac atttaaatct
1081 caaagcaatt cctgagctac atctgcttcc cacttacgt ttccaattga caattctttt
1141 ccttaaaat gagctaattt catagactcc tttgtgaaac cataaatcga ttattaggaa
1201 atttcacaaa tatgcataca tgtaggttgt aatgttaaaa tgttttaattt cacagaagcc
1261 ccactacaga tgcttcctg ttaaatgtta tattaatatt ggagtccaga atgttctgag
1321 catttttccaa ctctgttcca aacttactaa tcctctcct tgtgagctga tgtgtataag
1381 cagatttaaa tccttccctt tctgtactaa agggagaag aaaaggaaga gatcaccctc
1441 agtgcttctt tgctgtccct tttcttctaga catttaaccc ctttagttc agaaaatgta
1501 aactagcact agcatggtct tttaaggatt ttgttcatat cagtcatata tctgttatta
1561 ttatgtattt aaagattgtg tttattccca cgatttgaag aagcctagcc aaaaaaaaa
1621 aaaaaagat tgtgtttata ttattgctag aagatatgtg ttgatgggac caaaaaaga
1681 ctggttaata aataaaaatt ttttctacac taattatata taaaccatat tcacatgtac
1741 ctttattaat atatatatac cactatgtaa agaacttcat tgctctttta attagcttc
1801 tctttcactg actaatattt tggatcaaag tgagctcttc tttttggca caaacttata
1861 atcctattat ttaattctt ccagtgctgt acatatagta cataattcca gatgtttag
1921 tatgtttgat gaatatttct tttttttcaa tttacccat ctgaaattac ttcatagtct
1981 ttccagctag tcttttccatc gttgataoat aattgccaaa gtagccaagt tgaactccct
2041 actttaggga ttcttgagtc actactttgg attcttcaaa ggtccttcga ttctatgcaa
2101 tctgggatga tacagacagc atgtatgtg aatgtggac ctacatcatt cattactatc
2161 ttatggaacg tacggtggaa attcgagagg gaatgatggg agagatcatt
2221 tcccactcct aatgaaccga cagcgtgtgc ccaaagtttt gctggaaaat gcaaagaact
2281 tccctcagtg tgtgctagaa atctctgacc aagaagtgtt ggaatggtat actgctaaag
2341 acttcattgt tggaagtca ctcactatcc ttgggagaac tttcttcatt tatgattgtg
2401 atccatttac tcgacggtat tacaaagaga agtttggaat cactgattta ccacgtattg
2461 atgtgagcaa ggggaacca cctccagtaa aacaggagtt gctcctat aacggttttg
2521 gactagtgga agattctgct cagaatttgt ttgtctcat tccaaaagct ccaaaaaag
2581 aacgttatta aatgctggtg aatgataaca aggtgcttcg ttatttgct gtactggaat
2641 ccccatccc agaagacaaa gacgcagat ttgtcttcto ttactttcta gctacgaca
2701 tgatcagtat ctttgagcct cctgttgca attctggtat cattggggc aagtaccttg
2761 gcaggactaa agtgttaaa ccatactcta cagtgacaaa ccctgtctac tatggcccca
2821 gtgacttctt cattggtgct gtgattgaag tgtttggtca cggttcatc atccttgata
2881 cagacgagta tgtttgaaa tacatggaga gcaagctgc ccagtattca ccagaagcac
2941 tcgcgtcaat tcagaacat gtccgaaagc gagaggagg tgctccagaa gcagaaagca
3001 agcaaactga aaaggatcca ggcgtgcagg aattggaagc attaatagac acaattcaga
3061 agcaactgaa agatcactca tgcaagaca acattcgtga ggcatttcaa attttatgca
3121 aggaagcttc aggatatgtg gacagagaca tgttcttaa aatctgtgaa tcgcttaacg
3181 tccagtgga tgactcttg gttaaggagt tactcaggat gtgtctcat ggagaaggca
3241 aaattaacta ctataacttt gttcgtgctt tctcaaactg acctgctgat gagaaatgc
3301 aagacaatt ttgaactgg aactatgtt tgaaatacac cttacactct tcatagaggc
3361 atttacaggg ttcctgaagt ttatttctg tttggttct tatttcactc ctactgaagt
3421 cgaaactaaa ttggatcaaa aaaaaaa
```

NCBI Accession: AL122084;

Human EFHC1 polypeptide, alternatively spliced variant (AL122084): SEQ ID NO: 8

Figure 22

Transcript B c-terminus

Position 243-278

SDIGTTIGLLISKCDLHLLAKGLGSCIGNYFETLQ

SEQ ID NO: 9

Supplementary Table 1: Modulation of activation and inactivation properties of $Ca_v2.3$ by EFHC1 proteins

| | Activation | | | Inactivation | | |
|---|---|---|---|---|---|---|
| | n | $V_{0.5}$ (mV) | $k$ (mV) | n | $V_{0.5}$ (mV) | $k$ (mV) |
| GFP vector | 7 | 5.1 ± 6.1 | 15.7 ± 2.8 | 7 | -51.2 ± 4.0 | 11.8 ± 2.8 |
| WT EFHC1 | 9 | 12.6 ± 3.0 | 14.4 ± 1.1 | 15 | -54.6 ± 1.9 | 8.6 ± 0.34 |
| Iso | 4 | 10.3 ± 4.8 | 14.1 ± 1.6 | 4 | -56.4 ± 1.3 | 10.3 ± 1.8 |
| P77T | 9 | 6.7 ± 3.0 | 14.4 ± 1.9 | 9 | -58.4 ± 1.8 | 7.9 ± 0.36 |
| D210N | 7 | 7.2 ± 2.1 | 12.6 ± 1.1 | 6 | -56.7 ± 2.6 | 8.3 ± 0.31 |
| R221H | 8 | 7.0 ± 1.8 | 14.9 ± 1.6 | 8 | -60.0 ± 1.1 | 9.2 ± 0.87 |
| P77T / R221H | 4 | 8.0 ± 2.9 | 11.3 ± 2.8 | 4 | -58.4 ± 1.1 | 8.5 ± 1.1 |
| F229L | 16 | 3.0 ± 2.0 * | 13.4 ± 1.4 | 16 | -60.6 ± 1.3 ** | 8.7 ± 0.60 |
| D253Y | 6 | 10.0 ± 1.3 | 16.8 ± 1.4 | 6 | -55.8 ± 1.7 | 8.9 ± 0.84 | n, Number of cells recorded; $V_{0.5}$, half-maximal voltage of activation or inactivation; $k$, slope factor. Data points are mean ± SEM. *$p<0.05$, **$p<0.01$ (compared with WT EFHC1). P values are the result of Student's t-test.

Figure 25 a (Transcript A)

```
MVSNPVHGLPFLRGTSEKDSTKTAFHRSQT          30
LSYRNGYAIVRRPTVGIGGDRLQFNQLSQA          60
ELDELASKAPVLTYGQPKQAPPADFIPAHV          90
APDKKVLKFDAYFQEDVPMSTEEQYRIRQV         120
NIYYLEDDSMSVIEPVVENSGILQGKLIK          150
RQRLAKNDRGDHYHWKDLNRGINITIYGKT         180
FRVYDCDQFTQVFLESQGIEINPEKMALD          210
PYTELRKQPLRKYVTPSDFDQLKQFLTEDK         240
QVLRFYAIWDDJDSMYGECRTYIIHYLMD          270
DFVEIREVHERNDGRDPFPLIMNRQRVPKV         300
LVENAKNFPQCVLEISDQEVLEWYTAKDFI         330
VGKSLTILGRTFFIYDCDPFTRRYKEKFG          360
ITDLPRIDVSKREPPPVKQELPPYNGFGLV         390
EDSAQMCFTLIPKAPKKDVIKMLVNDNKVL         420
RYLAVLESPIPEDKDRRFVFSYFLATDMIS         450
IFRPPVRNSGIIGGKYLGRTKVVKPYSTVD         480
NFVYGPSDPFIGAVIEVFGHRFILDTDE           510
YVLKYMESNAAQYSPEALASIQNHVRKREA         540
PAPEAESKQTEKDPCVQELEALIDTIQKQL         570
KDHSCKDNIREAFQIYDKEASGYVDRDMFF         600
KICESLNVPVDDSLVKELIRMCSHGEGKIN         630
YYNFVRAFSN                             640
```

(Transcript B C terminus)

```
SDIGTTIGLLLISKCDLHLLAKGLGSCIGNY        272
FETLQL                                 278
``` b

Mutations

|  | 77 | 210 | 221 | 229 | 253 |
|---|---|---|---|---|---|
| Human | M | N | H | H | V |
| Mouse | ..YGQPKQA.. | ..MALPPYT.. | ..QPLRKYV.. | ..PSLPDQL.. | ..DDTDSMY.. |
| Pig | ..YGPHKQA.. | ..IPLPPYT.. | ..EPVRKYV.. | ..PSLPDQL.. | ..DDTDSLF.. |
| Cow | ..YGQRQA..  | ..MALPPYT.. | ..QPLRKYV.. | ..PTTPDQL.. | ..DDTDSMF.. |
|  | ..YGQRQA..  | ..MALPPYT.. | ..QPLRKYV.. | ..PTTPDQL.. | ..GWTDIMF.. |

Polymorphisms

|  | 159 | 182 | 619 |
|---|---|---|---|
| Human | M | H | H |
| Mouse | ..KNDRGDH.. | ..KTFPVVD.. | ..KELIRMC.. |
| Pig | ..KNDMGDH.. | ..KTFRIVD.. | ..KELIRLC.. |
| Cow | ..KNDRGDH.. | ..RTFRIVD.. | .......... |
|  | ..KNDRGDH.. | ..KTFRIVD.. | ..KELIRMC.. |

COMPOSITIONS AND METHODS FOR DIAGNOSIS AND TREATMENT OF EPILEPSY

CROSS-REFERENCE TO RELATED APPLICATIONS

This application is a continuation of U.S. patent application Ser. No. 11/572,201, filed on Jul. 15, 2005, which claims benefit of U.S. Provisional Patent Application No. 60/588,769, filed Jul. 16, 2004, the entire disclosures of which are incorporated herein by reference.

STATEMENT OF GOVERNMENT SUPPORT

This invention was made with Government support under Grant No. NS21908 and NS42376 awarded by the National Institutes of Health. The Government has certain rights in the invention. This work was supported by the U.S. Department of Veterans Affairs, and the Federal Government has certain rights in the invention.

SEQUENCE LISTING

This application contains a Sequence Listing which was filed in U.S. patent application Ser. No. 11/572,201, filed on Jul. 15, 2005, which was submitted via EFS-Web and is hereby incorporated by reference in its entirety. Said ASCII copy, created on Mar. 25, 2010, is named 26744US_CRF_sequencelisting.txt and is 47,925 bytes in size.

FIELD

The invention generally relates to compositions and methods for diagnosis and treatment of epilepsy disease with EFHC1, EFHC1 agonists, or EFHC1 analogs. The invention further relates to compositions and methods for diagnosis and treatment of epilepsy disease with EFHC1a, EFHC1a agonists, or EFHC1a analogs.

BACKGROUND

Juvenile myoclonic epilepsy (JME) is the most frequent cause of hereditary grand mal seizures. A JME region has been previously mapped and recently narrowed on chromosome 6p12-p11 (EJM1). Janz, *J. Neurol.*, 176: 344-386, 1957; Delgado-Escueta, et al., *Adv. Neurol.*, 79: 351-374, 1999; Liu, et al., *Am. J. Hum. Genet.*, 57: 368-381, 1995; Liu, et al., *Am. J. Med. Genet.*, 63: 438-446, 1996; et al., *Am. J. Med. Genet.*, 133: 268-274, 2002.

Two separate loci on the short arm of chromosome 6, 6p21.3 and 6p12-p11, have been proposed as JME regions. In the 6p21.3-HLA region, two SNP variants in BRD2 were in linkage disequilibrium with JME although no causative coding mutations were found. In contrast, JME families from Belize, Los Angeles, and Mexico, showed significantly high lod scores at the 6p12-p11 locus but exclusionary lod scores at 6p21.3. Recently, an independent study of Dutch JME families confirmed 6p12-p11 as a susceptibility locus for JME. Sander, et al., *Neurology*, 49: 842-847, 1997; Greenberg, et al., *Am. J. Hum. Genet.*, 66: 508-516, 2000; Pal, et al., *Am. J. Hum. Genet.*, 73: 261-270, 2003; Liu, et al., *Am. J. Hum. Genet.*, 57: 368-381, 1995; Liu, et al., *Am. J. Med. Genet.*, 63: 438-446, 1996; Bai, et al., *Am. J. Med. Genet.*, 133: 268-274, 2002; Pinto, et al., *Epilepsia*, 45: 211-217, 2004.

SUMMARY

The invention generally relates to compositions and methods for diagnosis and treatment of epilepsy disease with EFHC1, EFHC1 agonists, or EFHC1 analogs, or with EFHC1a, EFHC1a agonists, or EFHC1a analogs, or compositions and methods that regulate expression or activity of EFHC1 or EFHC1a polynucleotides or polypeptides. Benefits of the present invention can be obtained from the discovery of compositions and methods that include novel genes, EFHC1, in the EJM1 region on chromosome 6p12-p11, and EFHC1a, located on chromosome Xp11.4. The EFHC1a gene encodes myoclonin 2. The EFHC1 gene encodes myoclonin 1, a protein with an EF-hand motif. Mutation analyses revealed five missense mutations in EFHC1 co-segregating with epilepsy or EEG polyspike wave-affected members of six unrelated juvenile myoclonic epilepsy (JME) families that did not appear in 382 control individuals. EFHC1 overexpression in mouse hippocampal primary culture neurons induced apoptosis that was significantly lowered by the mutations at the JME locus. The apoptosis in the mouse hippocampal primary culture neurons was specifically suppressed by SNX-482, an antagonist of R-type voltage-dependent $Ca^{2+}$ channel ($Ca_v2.3$). EFHC1 and $Ca_v2.3$ immunomaterials overlapped in mouse brain, and EFHC1 co-immunoprecipitated with $Ca_v2.3$ C-terminus. In patch-clamp analysis, EFHC1 specifically increased R-type calcium currents that were reversed by JME mutations. These observations strongly favor EFHC1 as the EJM1 gene.

Mutations in EFHC1/myoclonin1 can produce the full disease phenotype and are found in 20 percent of Spanish Amerinds with JME. Variants of EFHC1/myoclonin 1 are susceptibility factors in 38 percent of JME patients. EFHC1a/Myoclonin 2, a homologue of myoclonin 1, is located in chromosome Xp11.4, and is being analyzed for mutations and function. EFHC1/myoclonin 1 and EFHC1a/myoclonin 2 can serve as diagnostic markers for JME. One may expect that 6 or more, or 8 or more genes may be associated with the onset of epilepsy, for example, juvenile myoclonic epilepsy found in families in Belize, Los Angeles, Mexico, Brazil, Holland, and Japan. Segregation of EFHC1 mutations in epilepsy or polyspike wave-affected persons of JME families, together with reversal of the EFHC1-induced neuronal cell death and EFHC1-dependent increase of R-type $Ca^{2+}$ current by JME mutations, strongly support EFHC1 as a JME gene on chromosome 6p12, and and support EFHC1a as a JME gene on chromosome Xp11.4. Most genes incriminated as the cause of idiopathic generalized epilepsy encode ion channels. Identification of a gene encoding a non-ion channel protein containing an EF-hand motif, modulating and interacting with R-type VDCC, and showing apoptotic activity, provides a new approach to the molecular pathology of idiopathic epilepsy.

In one embodiment of the invention, a method for inhibiting growth of a neuronal cell comprises contacting the cell with EFHC1, EFHC1 agonist, or EFHC1 analog. In a further embodiment, the method comprises contacting the cell with an anti-epileptic drug. In a further embodiment, the anti-epileptic drug comprises carbamazepine, ethosuximide, CBZ epoxide, lamotrigine, oxcarbazepine, sodium valproate, acetazolamide, clobazam, clonazepam, gabapentin, levetiracetam, phenobarbitone, phenyloin, piracetam, primidone, tiagabine, topiramate, zonisamide, or vigabatrin.

In yet another embodiment of the invention, a method for potentiating an epilepsy therapy in a patient are provided which comprise (a) administering EFHC1, EFHC1 agonist, or EFHC1 analog to the patient; and (b) administering anti-epileptic drug to the patient. In another embodiment, the anti-epileptic drug comprises carbamazepine, ethosuximide, CBZ epoxide, lamotrigine, oxcarbazepine, sodium valproate, acetazolamide, clobazam, clonazepam, gabapentin, levetiracetam, phenobarbitone, phenyloin, piracetam, primidone, tiagabine, topiramate, zonisamide, or vigabatrin. In a further embodiment, the EFHC1, the EFHC1 agonist, or the EFHC1 analog, is an agonist of R-type voltage-dependent $Ca^{2+}$ channel ($Ca_v2.3$). The epilepsy therapy is preferably for juvenile myoclonic epilepsy (JMC).

Methods for identifying agents that promote cell death in a mammalian cell in accordance with this invention comprise (a) providing a mammalian cell engineered to overexpress EFHC1 or EFHC1a; (b) contacting the cell with a test agent; and (c) assaying for the effect of the test agent on death of the cell. The methods preferably comprise contacting the cell with an anti-epileptic drug. In one embodiment, the anti-epileptic drug promotes apoptosis. In a further embodiment, the anti-epileptic drug comprises carbamazepine, ethosuximide, CBZ epoxide, lamotrigine, oxcarbazepine, sodium valproate, acetazolamide, clobazam, clonazepam, gabapentin, levetiracetam, phenobarbitone, phenyloin, piracetam, primidone, tiagabine, topiramate, zonisamide, or vigabatrin.

In one embodiment, the effect of the test agent on cell death is assayed by measuring the incidence of apoptosis. In a further embodiment, the effect of the test agent on death of the cell is assayed by measuring the activity of p53. The cell is preferably transfected with a nucleic acid construct encoding EFHC1 or EFHC1a. The cell may be either in vitro or in vivo, and may be in a rodent, especially a mouse.

Methods for identifying agents that modulate activity of an EFHC1 polypeptide are provided which comprise (a) contacting the EFHC1 polypeptide with the compound, wherein the EFHC1 polypeptide comprises at least 85% amino acid sequence identity to the amino acid sequence of SEQ ID NO: 4; and (b) determining the functional effect of the compound on the EFHC1 polypeptide. In one embodiment, the compound increases activity of the EFHC1 polypeptide. In a further embodiment, the polypeptide is linked to a solid phase, or further can be covalently linked to the solid phase. In a further aspect, the polypeptide is expressed in a cell. The polypeptide can be amplified in the cell compared to normal. In a further embodiment, the polypeptide has an amino acid sequence of SEQ ID NO: 4.

Methods for identifying agents that modulate activity of an apoptotic drug are provided which comprise (a) providing a mammalian cell engineered to overexpress EFHC1 or EFHC1a; (b) contacting the cell with a test agent and an apoptotic drug; and (c) assaying for the effect of the test agent on the activity of the apoptotic drug. In a further embodiment, the test agent potentiates the activity of the apoptotic drug. In a further embodiment, the apoptotic drug is a chemotherapeutic drug that induces apoptotic pathways.

Methods for monitoring the efficacy of an epilepsy treatment, are provided which comprise (a) providing a biological sample from a mammal undergoing the therapeutic treatment; and (b) detecting a level of an EFHC1 polypeptide comprising at least 70% amino acid identity to SEQ ID NO: 4 or an EFHC1 polynucleotide comprising at least 70% nucleotide identity to SEQ ID NO: 3 or detecting copy number of a gene encoding the EFHC1 polypeptide in a biological sample from a patient undergoing treatment for epilepsy, wherein an increased level of the EFHC1 polypeptide or EFHC1 polynucleotide or gene copy number in the biological sample compared to the level or copy number in a biological sample from the patient prior to, or earlier in, the treatment is indicative of efficacious treatment. In one embodiment, the EHC1 polypeptide has an amino acid sequence of SEQ ID NO: 4 or the EHC1 polynucleotide has a nucleotide sequence of SEQ ID NO: 3. In one aspect, the epilepsy is juvenile myoclonic epilepsy (JMC). In a further aspect, the patient is a human.

In yet another embodiment of the invention, methods of diagnosing epilepsy in a mammalian subject are provided which comprise (a) providing a biological sample from the mammalian subject; (b) detecting expression of EFHC1 polypeptide comprising at least 85% amino acid sequence identity to the amino acid sequence of SEQ ID NO: 4; and (c) correlating expression of EFHC1 polypeptide with the presence or absence of epilepsy in the subject. In a further embodiment, underexpression of EFHC1 polypeptide correlates with the presence of epilepsy in the subject.

Methods of diagnosing epilepsy in a mammalian subject in accordance with this invention comprise (a) providing a biological sample from the mammalian subject; (b) detecting a copy number of EFHC1 polynucleotide sequence comprising at least 85% nucleic acid sequence identity to the nucleic acid sequence of SEQ ID NO: 3; and (c) correlating the copy number of EFHC1 polynucleotide sequence with the presence or absence of epilepsy in the subject. In a further embodiment, a decrease in the copy number of EFHC1 polynucleotide sequence correlates with the presence of epilepsy in the subject.

Methods of diagnosing epilepsy in a mammalian subject are provided which comprise (a) providing a biological sample from the mammalian subject; (b) detecting a mutation in an EFHC1 gene comprising at least 85% nucleic acid sequence identity to the nucleic acid sequence of SEQ ID NO: 3; and (c) correlating the presence or absence of a mutation in an EFHC1 gene with the presence or absence of epilepsy in the subject. In a further embodiment, the presence of a mutation in an EFHC1 gene correlates with the presence of epilepsy in the subject. The mutation may comprise a missense mutation or a nonsense mutation in the EFHC1 gene.

In yet another embodiment of the invention, an isolated nucleic acid encodes an EFHC1 polypeptide, wherein the EFHC1 polypeptide comprises at least 95% amino acid sequence identity to SEQ ID NO: 4. In a further aspect, the nucleic acid encodes an EFHC1 polypeptide comprising an amino acid sequence of SEQ ID NO: 4. In a further aspect, the nucleic acid comprises a nucleotide sequence of SEQ ID NO: 3. In a further embodiment, an expression vector comprises the nucleic acid encoding an EFHC1 polypeptide comprising an amino acid sequence of SEQ ID NO: 4. An isolated host cell may comprise the expression vector.

Methods for producing an EFHC1 protein are provided which comprise the steps of: a) culturing the isolated host cell comprising the expression vector under conditions suitable for the expression of the polypeptide; and b) recovering the polypeptide from the host cell culture. In one aspect, the host cell is a eukaryotic cell. The host cell can be a prokaryotic cell.

In yet another embodiment of the invention, an isolated EFHC1 polypeptide comprises at least 95% amino acid identity to SEQ ID NO: 4. In one aspect, the polypeptide comprises an amino acid sequence of SEQ ID NO: 4. In a further aspect, the polypeptide specifically binds to antibodies generated against a polypeptide comprising an amino acid sequence of SEQ ID NO: 4. In a further aspect, antibodies specifically binds to the EFHC1 polypeptide.

Diagnostic kits in accordance with this invention comprise (a) one or more antibodies that specifically bind to the EFHC1 polypeptide; and (b) a detection reagent comprising a reporter group. In one embodiment, the antibodies are immobilized on a solid support. The solid support may comprise nitrocellulose, latex or a plastic material. In one aspect, the detection reagent comprises an anti-immunoglobulin, protein G, protein A or lectin. In a further aspect, the reporter group is selected from the group consisting of radioisotopes, fluorescent groups, luminescent groups, enzymes, biotin and dye particles.

In yet another embodiment of the invention, an oligonucleotide comprises 10 to 40 nucleotides that hybridize under stringent conditions to a polynucleotide that encodes a EHC1 protein, wherein the EHC1 protein comprises an amino acid sequence that is encoded by a polynucleotide sequence of SEQ ID NO: 3 or a complement of any of the foregoing polynucleotides. In a further embodiment, the oligonucleotide comprises 10-40 nucleotides recited in SEQ ID NO: 3. Diagnostic kits in accordance with the invention comprise (a) the oligonucleotide comprising 10 to 40 nucleotides that hybridize under stringent conditions to a polynucleotide that encodes a EHC1 protein; and (b) a diagnostic reagent for use in a polymerase chain reaction or hybridization assay.

Methods for monitoring the efficacy of an epilepsy treatment are provided which comprise (a) providing a biological sample from a mammal undergoing the therapeutic treatment; and (b) detecting a level of an EFHC1a polypeptide or an EFHC1a polynucleotide or detecting copy number of a gene encoding the EFHC1a polypeptide in a biological sample from a patient undergoing treatment for epilepsy, wherein an increased level of the EFHC1a polypeptide or EFHC1a polynucleotide or gene copy number in the biological sample compared to the level or copy number in a biological sample from the patient prior to, or earlier in, the treatment is indicative of efficacious treatment. The epilepsy treatment is preferably for juvenile myoclonic epilepsy (JMC). In a further aspect, the patient is a human.

Methods of diagnosing epilepsy in a mammalian subject in accordance with this invention comprise (a) providing a biological sample from the mammalian subject; (b) detecting expression of EFHC1a polypeptide; and (c) correlating expression of EFHC1a polypeptide with the presence or absence of epilepsy in the subject. In a further embodiment, underexpression of EFHC1a polypeptide correlates with the presence of epilepsy in the subject.

Methods of diagnosing epilepsy in a mammalian subject are provided which comprise (a) providing a biological sample from the mammalian subject; (b) detecting a copy number of EFHC1a polynucleotide sequence; and (c) correlating the copy number of EFHC1a polynucleotide sequence with the presence or absence of epilepsy in the subject. In a further embodiment, a decrease in the copy number of EFHC1a polynucleotide sequence correlates with the presence of epilepsy in the subject.

Methods of diagnosing epilepsy in a mammalian subject in accordance with this invention comprise (a) providing a biological sample from the mammalian subject; (b) detecting presence or absence of a mutation in an EFHC1a gene; and (c) correlating the presence or absence of a mutation in an EFHC1a gene with the presence or absence of epilepsy in the subject. In one aspect, the presence of a mutation in an EFHC1a gene correlates with the presence of epilepsy in the subject. The mutation may comprise a missense mutation or a nonsense mutation in the EFHC1a gene.

BRIEF DESCRIPTION OF THE DRAWINGS

FIG. 8 shows EFHC1 decelerates PQ type VDCC inactivation.

FIG. 13 shows (a) RT-PCR analyses of mRNA from mouse whole brain tissue and hippocampal primary culture neurons. (b) Northern-blot analyses of mouse Efhc1 from mouse tissues. (c) Western blot analyses with anti-EFHC1 antibody.

FIG. 16 shows the deduced human cDNA sequence (FLJ22843; SEQ ID NO: 1); NCBI accession number NM_025184.

FIG. 17 shows the deduced human polypeptide sequence (FLJ22843; SEQ ID NO: 2); NCBI accession number NP_079460.

FIGS. 18A and 18B show a comparison of EFHC1 polypeptide sequence (NCBI accession number AK001328; NM_018100; SEQ ID NO: 4), with mouse polypeptide (NCBI accession number AK006489; SEQ ID NO: 5), and human polypeptide (FLJ22843; SEQ ID NO: 2)

FIGS. 19A and 19B show a comparison of human polypeptide (FLJ22843; SEQ ID NO: 2), with *Drosophila* polypeptide (NCBI accession number CG8959; SEQ ID NO: 6), and *Drosophila* polypeptide (NCBI accession number CG11048; SEQ ID NO: 7)

FIG. 20 shows the deduced human EFHC1 cDNA sequence (NCBI Accession: AK001328; NM_018100; SEQ ID NO: 3).

FIG. 21 shows the deduced human EFHC1 polypeptide sequence, transcript A (NCBI Accession: AK001328; NM_018100; SEQ ID NO: 4).

FIG. 22 shows the deduced human EFHC1 cDNA sequence (NCBI Accession: AL122084; SEQ ID NO: 8) which is an alternatively spliced variant.

FIG. 23 shows the deduced human EFHC1 polypeptide, positions 243-278 of transcript B, c-terminus, (SEQ ID NO: 9) which is an alternatively spliced variant.

FIG. 24 shows modulation and inactivation properties of $Ca_v2.3$ by EFHC1 proteins.

FIG. 25 shows the predicted amino acid sequence of the protein encoded by human EFHC1 gene transcript A (SEQ ID NO: 4), and amino acid sequence alignment of putative EFHC1 orthologs from mouse, pig, and cow. FIG. 25*a* discloses the "Transcript B C terminus" sequence as SEQ ID NO: 10. FIG. 25*b* discloses the "Mutations" sequences as SEQ ID NOS 11, 28-31, 12, 32-35, 13, 36-38, 14 and 39-42, respectively, in order of appearance. FIG. 25*b* discloses the "Polymorphisms" sequences as SEQ ID NOS 15, 43-44, 16, 45-46, 17-18 and 47-48, respectively, in order of appearance.

DETAILED DESCRIPTION

Figure 1:
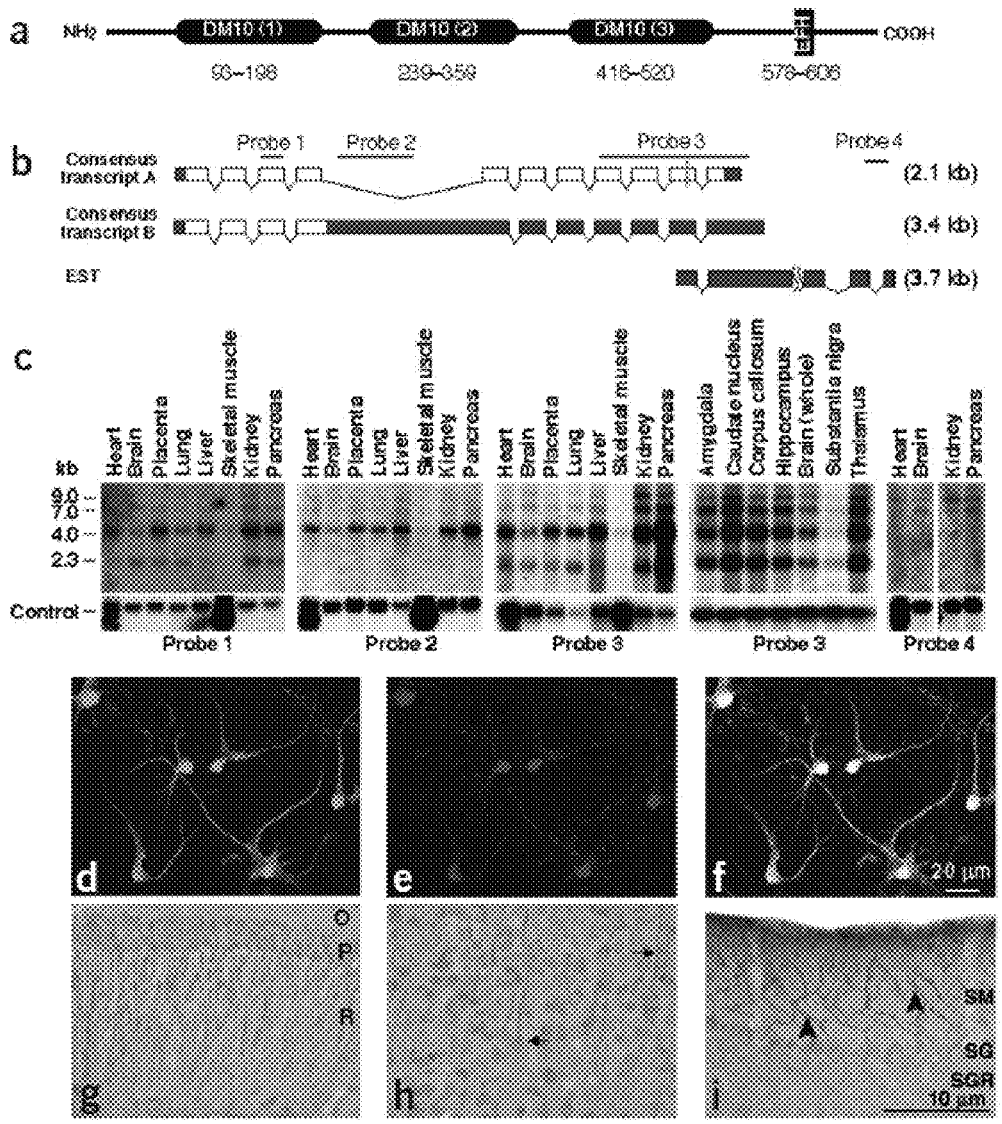
FIG. 1 shows the structure and expression of EFHC1.

The present invention provides methods of production of EFHC1/myoclonin 1 or EFHC1a/myoclonin 2 polynucleotide or polypeptide. The sequences can be used for the identification of molecules that associate with and/or modulate the activity of EFHC1 or EFHC1a, or for the diagnosis of epilepsy or other diseases or conditions associated with EFHC1 or EFHC1a amplification or EFHC1 or EFHC1a activity or expression. In one aspect, the invention is based upon the discovery that the EFHC1 or EFHC1a gene is mutated and/or underexpressed in neuronal cells, particularly hippocampal cells. Accordingly, the present methods can be used to monitor the efficacy of a epilepsy treatment, for example, juvenile myoclonic epilepsy (JME) and to treat epilepsy, e.g., by inhibiting the expression and/or activity of EFHC1 or EFHC1a in a neuronal cell.

The invention also provides methods of screening for modulators, e.g., activators, inhibitors, stimulators, enhancers, and the like, of EFHC1 or EFHC1a nucleic acids and proteins. Such modulators can affect EFHC1 or EFHC1a activity, e.g., by modulating EFHC1 or EFHC1a transcription, translation, mRNA or protein stability; by altering the interaction of EFHC1 or EFHC1a with other molecules (e.g., EFHC1 or EFHC1a regulated genes); or by affecting EFHC1 or EFHC1a protein activity. In one embodiment, compounds are screened, e.g., using high throughput screening (HTS), to identify those compounds that can bind to and/or modulate the activity of an isolated EFHC1 or EFHC1a polypeptide or fragment thereof. In another embodiment, EFHC1 or EFHC1a proteins are recombinantly expressed in cells, and the modulation of EFHC1 or EFHC1a is assayed by using any measure of EFHC1 or EFHC1a function.

In numerous embodiments, an EFHC1 or EFHC1a polynucleotide or polypeptide is introduced into a cell, in vivo or ex vivo, and the EFHC1 or EFHC1a activity in the cell is thereby modulated. For example, a polynucleotide encoding a full length EFHC1 or EFHC1a polypeptide can be introduced into a population of cells.

In certain embodiments, monoclonal or polyclonal antibodies directed to EFHC1 or EFHC1a, or subfragment or domain of EFHC1 or EFHC1a, will be administered to a patient to inhibit the activity of EFHC1 or EFHC1a in cells. Such embodiments are useful, e.g., in the treatment of a disease or disorder associated with EFHC1 or EFHC1a activity.

The present invention also provides methods for detecting EFHC1 or EFHC1a nucleic acid and protein expression. EFHC1 or EFHC1a polypeptides can also be used to generate monoclonal and polyclonal antibodies useful for the detection of EFHC1- or EFHC1a-expressing cells or for the potentiation of EFHC1 or EFHC1a activity. Cells that express EFHC1 or EFHC1a can also be identified using techniques such as reverse transcription and amplification of mRNA, isolation of total RNA or poly A+ RNA, northern blotting, dot blotting, in situ hybridization, RNase protection, S1 digestion, probing DNA microchip arrays, western blots, and the like.

Nucleotide and amino acid sequence information for EFHC1 or EFHC1a are also used to construct models of EFHC1 or EFHC1a proteins. These models are subsequently used to identify compounds that can activate or inhibit EFHC1 or EFHC1a proteins. Such compounds that modulate the activity of EFHC1 or EFHC1a genes or proteins can be used to investigate the physiological role of EFHC1 or EFHC1a genes.

The present invention also provides assays, preferably high throughput screening (HTS) assays, to identify compounds or other molecules that interact with and/or modulate EFHC1 or EFHC1a. In certain assays, a particular domain of EFHC1 or EFHC1a is used, e.g., a conserved domain.

The present invention also provides methods to treat diseases or conditions associated with EFHC1 or EFHC1a activity. For example, EFHC1 or EFHC1a activity and/or expression can be altered in cells of a patient with an EFHC1- or EFHC1a-associated disease. In particular, the invention provides for methods of treating epilepsy.

Methods of the invention directed to treating epilepsy typically involve detecting the presence of EFHC1 or EFHC1a in a biological sample taken from a patient. In certain embodiments, a level of EFHC1 or EFHC1a in a biological sample will be compared with a control sample taken from a epilepsy-free patient or, preferably, with a value expected for a sample taken from a epilepsy-free patient. A control sample can also be obtained from normal tissue from the same patient that is suspected of having epilepsy.

The ability to detect neuronal cells by virtue of an increased level of EFHC1 or EFHC1a is useful for any of a large number of applications. For example, an increased level of EFHC1 or EFHC1a in cells of a patient can be used, alone or in combination with other diagnostic methods, to diagnose epilepsy in the patient or to determine the propensity of a patient to develop epilepsy over time. The detection of EFHC1 or EFHC1a can also be used to monitor the efficacy of a epilepsy treatment. For example, a level of an EFHC1 or EFHC1a polypeptide or polynucleotide after an anti-epilepsy treatment is compared to the level in the patient before the treatment. An increase in the level of the EFHC1 or EFHC1a polypeptide or polynucleotide after the treatment indicates efficacious treatment.

A decreased level or diagnostic presence of EFHC1 or EFHC1a can also be used to influence the choice of anti-epilepsy treatment in a patient, where, for example, the level of EFHC1 or EFHC1a decrease directly correlates with the aggressiveness of the anti-epilepsy therapy. For example, an increased level of EFHC1 or EFHC1a in tumor cells can indicate that the use of an agent that increases proliferation would be effective in treating the epilepsy.

In addition, the ability to detect epilepsy in neuronal cells can be used to monitor the number or location of neuronal cells in a patient, in vitro or in vivo, for example, to monitor the progression of epilepsy over time. In addition, the level or presence or absence of EFHC1 or EFHC1a can be statistically correlated with the efficacy of particular anti-epilepsy therapies or with observed prognostic outcomes, thereby allowing for the development of databases based on a statistically-based prognosis, or a selection of the most efficacious treatment, can be made in view of a particular level or diagnostic presence of EFHC1 or EFHC1a.

The present invention also provides methods for treating epilepsy. In certain embodiments, the proliferation of a cell with a reduced level of EFHC1 or EFHC1a polynucleotides, polypeptides, or polypeptide activity is inhibited. In other embodiments, EFHC1 or EFHC1a expression is not decreased compared to normal, but EFHC1 or EFHC1a activity, for example, functions at the cell surface membrane, can be stimulated to prevent neuronal cell growth or migration. Cell growth and/or migration is decreased by, for example, contacting the cell with an activator of EFHC1 or EFHC1a transcription or translation, or an activator of the activity of an EFHC1 or EFHC1a polypeptide. Such activator include, but are not limited to, antisense polynucleotides, ribozymes, antibodies that can stimulate EFHC1 or EFHC1a activity, or agonists of EFHC1 or EFHC1a polypeptides, or small molecule activator of EFHC1 or EFHC1a activity.

The present methods can be used to diagnose, determine the prognosis for, or treat, any of a number of types of epilepsy disease, e.g., juvenile myoclonal epilepsy (JME).

The methods of this invention can be used in animals including, for example, primates, canines, felines, murines, bovines, equines, ovines, porcines, lagomorphs, etc, as well as in humans. In a preferred embodiment, the mammal is a human.

Kits are also provided for carrying out the herein-disclosed therapeutic methods.

As used herein, the following terms have the meanings ascribed to them unless specified otherwise.

"Potentiate" refers to making effective or active or more effective or more active; or augmenting the activity of a drug synergistically to improve treatment of a disease, e.g., an epilepsy therapy, or juvenile myoclonic epilepsy (JME) therapy.

"Patient" or "subject" are used interchangeably and refer to mammals such as human patients and non-human primates, as well as experimental animals such as rabbits, rats, and mice, and other animals.

"Biological sample" refers to a sample of biological tissue, fluid, or cells that contains EFHC1 or EFHC1a or nucleic acid encoding EFHC1 or EFHC1a protein. Such samples include, but are not limited to, tissue isolated from humans. Biological samples can also include sections of tissues such as frozen sections taken for histologic purposes. A biological sample is typically obtained from a eukaryotic organism, preferably eukaryotes such as fungi, plants, insects, protozoa, birds, fish, reptiles, and preferably a mammal such as rat, mice, cow, dog, guinea pig, or rabbit, and most preferably a primate such as chimpanzees or humans.

"Treating" includes the administration of the compounds or agents of the present invention to prevent or delay the onset of the symptoms, complications, or biochemical indicia of a disease, alleviating the symptoms or arresting or inhibiting further development of the disease, condition, or disorder (e.g., epilepsy or juvenile myoclonic epilepsy). Treatment can be prophylactic (to prevent or delay the onset of the disease, or to prevent the manifestation of clinical or subclinical symptoms thereof) or therapeutic suppression or alleviation of symptoms after the manifestation of the disease.

"Epilepsy" refers to any of a number of diseases that are characterized by a neurological condition that makes people susceptible to seizures. A seizure is a change in sensation, awareness, or behavior brought about by a brief electrical disturbance in the brain. Seizures vary from a momentary disruption of the senses, to short periods of unconsciousness or staring spells, to convulsions. Some people have just one type of seizure. Others have more than one type.

"Juvenile myoclonic epilepsy (JME)" (also called Janz's syndrome, impulsive petit mal, myoclonic epilepsy of adolescence and jerk epilepsy) was first described in 1956 by Dr. Dieter Janz, who called it impulsive petit mal because of the sudden jerking (myoclonic) seizures that are a prominent part of the syndrome. The syndrome is characterized by myoclonic seizures (sudden jerks of arms and legs), especially on awakening. Juvenile myoclonic epilepsy generally appears at puberty, but may have existed prior to that time and it is usually not outgrown; it is also associated with generalized tonic-clonic seizures. Seizures may be precipitated by sleep deprivation; early awakening; alcohol and drug use; stress; strong emotion, photic stimulation, and menstruation.

"Apoptosis" and "programmed cell death (PCD)" are used as synonymous terms and describe the molecular and morphological processes leading to controlled cellular self-destruction. Apoptotic cell death can be induced by a variety of stimuli, such as ligation of cell surface receptors, starvation, growth factor/survival factor deprivation, heat shock, hypoxia, DNA damage, viral infection, and cytotoxic/chemotherapeutical agents. The apoptotic process is involved in embryogenesis, differentiation, proliferation/homoeostasis, removal of defect and therefore harmful cells, and especially in the regulation and function of the immune system. Thus, dysfunction or disregulation of the apoptotic program is implicated in a variety of pathological conditions, such as immunodeficiency, autoimmune diseases, neurodegenerative diseases, epilepsy and cancer. Apoptotic cells can be recognized by stereotypical morphological changes: the cell shrinks, shows deformation and looses contact to its neighboring cells. Its chromatin condenses, and finally the cell is fragmented into compact membrane-enclosed structures, called "apoptotic bodies" which contain cytosol, the condensed chromatin, and organelles. The apoptotic bodies are engulfed by macrophages and thus are removed from the tissue without causing an inflammatory response. This is in contrast to the necrotic mode of cell death in which case the cells suffer a major insult, resulting in loss of membrane integrity, swelling and disrupture of the cells. During necrosis, the cell contents are released uncontrolled into the cell's environment what results in damage of surrounding cells and a strong inflammatory response in the corresponding tissue. See, e.g., Tomei L. D. and Cope F. O., eds., 1991, APOPTOSIS: THE MOLECULAR BASIS OF CELL DEATH, Plainville, N.Y.: Cold Spring Harbor Laboratory Press; Isaacs J. T., 1993, Environ Health Perspect. 101(suppl 5):27-33; each of which is herein incorporated by reference in its entirety for all purposes. A variety of apoptosis assays are well known to one of skill in the art (e.g., DNA fragmentation assays, radioactive proliferation assays, DNA laddering assays for treated cells, Fluorescence microscopy of 4'-6-Diamidino-2-phenylindole (DAPI) stained cells assays, and the like). Kerr, et al., *Br. J. Cancer,* 26: 239-257, 1972.

"EFHC1 or EFHC1a" refers to EFHC1 or EFHC1a nucleic acid and polypeptide polymorphic variants, alleles, mutants, and interspecies homologs that: (1) have an amino acid sequence that has greater than about 60% amino acid sequence identity, preferably 65%, 70%, 75%, 80%, 85%, 90%, preferably 86%, 87%, 88%, 89%, 90%, 91%, 92%, 93%, 94%, 95%, 96%, 97%, 98% or 99% or greater amino acid sequence identity, preferably over a region of over a region of at least about 50, 100, 200, 500, 1000, or more amino acids, corresponding to the sequence of the naturally occurring EFHC1 gene as, e.g., provided in SEQ ID NO: 2; (2) bind to antibodies, e.g., polyclonal antibodies, raised against an immunogen comprising an amino acid sequence corresponding to the sequence of the naturally occurring EFHC1 or EFHC1a gene, and conservatively modified variants thereof; (3) specifically hybridize under stringent hybridization conditions to the sequence of the naturally occurring EFHC1 or EFHC1a gene and conservatively modified variants thereof; (4) have a nucleic acid sequence that has greater than about 80%, preferably about 85% or 90%, preferably greater than about 96%, 97%, 98%, 99%, or higher nucleotide sequence identity, preferably over a region of over a region of at least about 50, 100, 200, 500, 1000, or more nucleotides, corresponding to the sequence of the naturally occurring EFHC1 gene as, e.g., provided in SEQ ID NO: 1. An EFHC1 or EFHC1a polynucleotide or polypeptide sequence is typically from a mammal including, but not limited to, human, rat, mouse, hamster, cow, pig, horse, sheep, or any mammal An "EFHC1 or EFHC1a polynucleotide" and an "EFHC1 or EFHC1a polypeptide" are both either naturally occurring or recombinant. An "EFHC1 or EFHC1a protein" or "polypeptide" can comprise naturally occurring or synthetic amino acids, e.g., labeled or otherwise modified amino acids or amino acid analogs. An "EFHC1 or EFHC1a protein" will typically contain one or more characteristic protein motifs, any of which can be used independently of other elements normally present in a full-length EFHC1 or EFHC1a protein, and will have one or more characteristic activities or properties, e.g., An "EFHC1 or EFHC1a protein" can refer to any naturally occurring or synthetic EFHC1 or EFHC1a polypeptide as described above. The naturally occurring human EFHC1 is located at chromosome 20q13.2 based on the Human Genome Project draft sequence data, listed at National Center for Biotechnology Information (NCBI) in LOCUSLINK at LOCUSID7764. The naturally occurring EFHC1a gene is located at chromosome Xp11.4, based on the Human Genome Project draft sequence data. EFHC1 gene encodes a polypeptide, myoclonin 1. EFHC1a gene encodes a polypeptide, myoclonin 2.

A "full length" EFHC1 or EFHC1a protein or nucleic acid refers to an EFHC1 or EFHC1a polypeptide or polynucleotide sequence, or a variant thereof, that contains all of the elements normally contained in one or more naturally occurring, wild type EFHC1 or EFHC1a polynucleotide or polypeptide sequences.

"Nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid (e.g., EFHC1 or EFHC1a) and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues. The term nucleic acid is used interchangeably with gene, cDNA, and mRNA encoded by a gene. Batzer, et al., *Nucleic Acid Res.,* 19: 5081, 1991; Ohtsuka, et al., *J. Biol. Chem.,* 260: 2605-2608, 1985; Cassol, et al., 1992; Rossolini, et al., *Mol. Cell. Probes,* 8: 91-98, 1994.

"Nucleic acid probe" is defined as a nucleic acid capable of binding to a target nucleic acid (e.g., a nucleic acid associated with epilepsy) of complementary sequence through one or more types of chemical bonds, usually through complementary base pairing, usually through hydrogen bond formation. As used herein, a probe can include natural (i.e., A, G, C, or T) or modified bases (7-deazaguanosine, inosine, and the like). In addition, the bases in a probe can be joined by a linkage other than a phosphodiester bond, so long as it does not interfere with hybridization. Thus, for example, probes can be peptide nucleic acids in which the constituent bases are joined by peptide bonds rather than phosphodiester linkages. It will be understood by one of skill in the art that probes can bind target sequences lacking complete complementarity with the probe sequence depending upon the stringency of the hybridization conditions.

Nucleic acid probes can be DNA or RNA fragments. DNA fragments can be prepared, for example, by digesting plasmid DNA, or by use of PCR, or synthesized by either the phosphoramidite method described by Beaucage and Carruthers, 1981, Tetrahedron Lett. 22:1859-1862, or by the triester method according to Matteucci, et al., 1981, J. Am. Chem. Soc., 103:3185, both incorporated herein by reference. A double stranded fragment can then be obtained, if desired, by annealing the chemically synthesized single strands together under appropriate conditions, or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid.

"Labeled nucleic acid probe" is a nucleic acid probe that is bound, either covalently, through a linker, or through ionic, van der Waals or hydrogen bonds to a label such that the presence of the probe can be detected by detecting the presence of the label bound to the probe.

"A nucleic acid sequence encoding" refers to a nucleic acid which contains sequence information for a structural RNA such as rRNA, a tRNA, or the primary amino acid sequence of a specific protein or peptide, or a binding site for a trans-acting regulatory agent. This phrase specifically encompasses degenerate codons (i.e., different codons which encode a single amino acid) of the native sequence or sequences which can be introduced to conform with codon preference in a specific host cell.

"Recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or, in the case of cells, to progeny of a cell so modified. Thus, for example, recombinant cells express genes that are not found within the native (non-recombinant) form of the cell or express native genes that are otherwise abnormally expressed, under expressed or not expressed at all.

"Heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent substitutions" or "silent variations," which are one species of "conservatively modified variations." Every polynucleotide sequence described herein which encodes a polypeptide also describes every possible silent variation, except where otherwise noted. Thus, silent substitutions are an implied feature of every nucleic acid sequence which encodes an amino acid. One of skill will recognize that each codon in a nucleic acid (except AUG, which is ordinarily the only codon for methionine) can be modified to yield a functionally identical molecule by standard techniques. In some embodiments, the nucleotide sequences that encode the enzymes are preferably optimized for expression in a particular host cell (e.g., yeast, mammalian, plant, fungal, and the like) used to produce the enzymes.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, 1984, PROTEINS).

Macromolecular structures such as polypeptide structures can be described in terms of various levels of organization. For a general discussion of this organization, see, e.g., Alberts et al., 1994, MOLECULAR BIOLOGY OF THE CELL, 3$^{rd}$ Ed., and Cantor and Schimmel, 1980, BIOPHYSICAL CHEMISTRY Part I: THE CONFORMATION OF BIOLOGICAL MACROMOLECULES. "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript can be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

"Biological sample" refers to a sample of cells, biological tissue or fluid that contains one or more EFHC1 or EFHC1a nucleic acids encoding one or more EFHC1 or EFHC1a proteins. Most often, the sample has been removed from a patient or subject, but the term "biological sample" can also refer to cells or tissue analyzed in vivo, i.e., without removal from the patient or subject. Typically, a "biological sample" will contain cells from the patient or subject, but the term can also refer to noncellular biological material, such as noncellular fractions of blood, saliva, or urine, that can be used to measure EFHC1 or EFHC1a levels. Numerous types of biological samples can be used in the present invention, including, but not limited to, a tissue biopsy, a blood sample, a buccal scrape, a saliva sample, or a nipple discharge. Such samples include, but are not limited to, tissue isolated from humans, mice, and rats, in particular, breast and lung tissue as well as blood, lymphatic tissue, liver, brain, heart, spleen, testis, ovary, thymus, kidney, and embryonic tissues. Biological samples can also include sections of tissues such as frozen sections taken for histological purposes. A biological sample is typically obtained from a mammal such as rat, mouse, cow, dog, cat, guinea pig, or rabbit, and most preferably a primate such as a chimpanzee or a human.

"Providing a biological sample" means to obtain a biological sample for use in the methods described in this invention. Most often, this will be done by removing a sample of cells from a patient or subject, but can also be accomplished by using previously isolated cells (e.g., isolated by another person, at another time, and/or for another purpose), or by performing the methods of the invention in vivo.

"Tissue biopsy" refers to an amount of tissue removed from a patient or subject for diagnostic analysis. In a patient with epilepsy, tissue can be removed from a tumor, allowing the analysis of cells within the tumor. "Tissue biopsy" can refer to any type of biopsy, such as needle biopsy, fine needle biopsy, surgical biopsy, and the like.

"Control sample" refers to a sample of biological material representative of healthy, epilepsy-free patients. The level of EFHC1 or EFHC1a in a control sample is desirably typical of the general population of normal, epilepsy-free patients. This sample can be removed from a patient expressly for use in the methods described in this invention, or can be any biological material representative of normal, epilepsy-free patients. A control sample can also be obtained from normal tissue from the patient that has epilepsy or is suspected of having epilepsy. A control sample can also refer to an established level of EFHC1 or EFHC1a, representative of the epilepsy-free population, that has been previously established based on measurements from normal, epilepsy-free patients. If a detection method is used that only detects EFHC1 or EFHC1a when a level higher than that typical of a normal, epilepsy-free patient is present, i.e., an immunohistochemical assay giving a simple positive or negative result, this is considered to be assessing the EFHC1 or EFHC1a level in comparison to the control level, as the control level is inherent in the assay.

The "level of EFHC1 or EFHC1a mRNA" in a biological sample refers to the amount of mRNA transcribed from an EFHC1 or EFHC1a gene that is present in a cell or a biological sample. The mRNA generally encodes a functional EFHC1 or EFHC1a protein, although mutations or microdeletions can be present that alter or eliminate the function of the encoded protein. A "level of EFHC1 or EFHC1a mRNA" need not be quantified, but can simply be detected, e.g., a subjective, visual detection by a human, with or without comparison to a level from a control sample or a level expected of a control sample.

The "level of EFHC1 or EFHC1a protein or polypeptide" in a biological sample refers to the amount of polypeptide translated from an EFHC1 or EFHC1a mRNA that is present in a cell or biological sample. The polypeptide can or can not have EFHC1 or EFHC1a protein activity. A "level of EFHC1 or EFHC1a protein" need not be quantified, but can simply be detected, e.g., a subjective, visual detection by a human, with or without comparison to a level from a control sample or a level expected of a control sample.

An "increased" or "elevated" level of EFHC1 or EFHC1a refers to a level of EFHC1 or EFHC1a polynucleotide, e.g., genomic DNA, or mRNA, or polypeptide, that, in comparison with a control level of EFHC1 or EFHC1a, is detectably higher. The method of comparison can be statistical, using quantified values for the level of EFHC1 or EFHC1a, or can be compared using nonstatistical means, such as by a visual, subjective assessment by a human.

For diagnostic and prognostic applications in epilepsy, a level of EFHC1 or EFHC1a polypeptide or polynucleotide that is "expected" in a control sample refers to a level that represents a typical, epilepsy-free sample, and from which an elevated, or diagnostic, presence of EFHC1 or EFHC1a polypeptide or polynucleotide can be distinguished. Preferably, an "expected" level will be controlled for such factors as the age, sex, and medical history, of the patient or subject, as well as for the particular biological sample being tested.

"Functional effects" in the context of assays for testing compounds that modulate EFHC1 or EFHC1a activity includes the determination of any parameter that is indirectly or directly under the influence of EFHC1 or EFHC1a, e.g., a functional, physical, or chemical effect. These effects include gene amplification, or expression in neuronal cells. "Functional effects" include in vitro, in vivo, and ex vivo activities.

"Determining the functional effect" refers to assaying for a compound that increases or decreases a parameter that is indirectly or directly under the influence of EFHC1 or EFHC1a, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties for the protein, measuring inducible markers or transcriptional activation of EFHC1 or EFHC1a; or binding assays, e.g., measuring the association of EFHC1 or EFHC1a with other proteins.

"Inhibitors" and "modulators" of EFHC1 or EFHC1a refers to inhibitory or modulating molecules identified using in vitro and in vivo assays of EFHC1 or EFHC1a, e.g., EFHC1 or EFHC1a expression in cell membranes. Inhibitors are compounds that, e.g., bind to, partially or totally block activity, decrease, prevent, delay activation, inactivate, desensitize, or down regulate the activity of EFHC1 or EFHC1a, e.g., antagonists. Activators are compounds that, e.g., increase EFHC1 or EFHC1a activity, or increase EFHC1 or EFHC1a expression or stability. Activators of EFHC1 or EFHC1a activity can be EFHC1 agonists or EFHC1a agonists. Modulators of EFHC1 or EFHC1a also include genetically modified versions of EFHC1 or EFHC1a, e.g., versions with altered activity, as well as naturally occurring and synthetic ligands, antagonists, agonists, antibodies, small chemical molecules and the like. Assays for inhibitors and activators of EFHC1 or EFHC1a include, e.g., expressing EFHC1 or EFHC1a in vitro, in cells, or cell membranes, applying putative modulator compounds, and then determining the functional effects on EFHC1 or EFHC1a activity, as described above.

"Inhibiting cell growth" refers to a decrease in cell growth in the presence of an EFHC1 or EFHC1a polypeptide, relative to the cell growth in the absence of the EFHC1 or EFHC1a polypeptide. Alternatively, if a cell has a basal level of EFHC1 or EFHC1a polypeptide expression, it refers to a decrease in cell growth in the presence of increased levels of EFHC1 or EFHC1a polypeptide, relative to cell growth in the presence of the basal level of EFHC1 or EFHC1a polypeptide. Cell growth can be measured using conventional assays, such as a colony-forming assay.

"Modulate" refers to the suppression, enhancement or induction of a function or condition. For example, the EFHC1, EFHC1 agonists, or EFHC1 analogs of the invention or the EFHC1a, EFHC1a agonists, or EFHC1a analogs of the invention may modulate epilepsy by activation or inhibition of calcium ($Ca^{2+}$) channel activity. For example, EFHC1, EFHC1 agonists, or EFHC1 analogs can activate or inhibit calcium ($Ca^{2+}$) channel activity in neuronal cells thereby alleviating epilepsy by inhibiting or reducing growth of neuronal cells.

"Neuronal cell" refers to cells of the central-nervous system, including neurons, astrocytes, oligodendrocytes and the like. In one embodiment, the neuronal cells of the present invention are cells derived from the soma and dendrites of pyramidal neurons of hippocampus CA1 region, pyramidal neurons of cerebral cortex, or purkinje cells of cerebellum.

"Contacting" refers to the addition of a compound to an in vitro culture or the administration to a subject in vivo, such that the compound will taken up by a cell, for example, a nerve cell.

Samples or assays comprising EFHC1 or EFHC1a polypeptides that are treated with a potential activator, inhibitor, or modulator are compared to control samples without the inhibitor, activator, or modulator to examine the effect of the candidate compound. Control samples (untreated with the compound) are assigned a relative EFHC1 or EFHC1a activity value of 100% Inhibition of an EFHC1 or EFHC1a polypeptide is achieved when the activity value relative to the control is about 80%, optionally about 50% or 25-0%. Activation of an EFHC1 or EFHC1a polypeptide is achieved when the activity value relative to the control is about 110%, optionally about 150%, optionally about 200-500%, or about 1000-3000% higher.

"Isolated", "purified", or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated EFHC1 or EFHC1a nucleic acid is separated from open reading frames that flank the EFHC1 or EFHC1a gene and encode proteins other than EFHC1 or EFHC1a. The term "purified" denotes that a nucleic acid or protein gives rise to essentially one band in an electrophoretic gel. Particularly, it means that the nucleic acid or protein is at least 85% pure, optionally at least 95% pure, and optionally at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions can be achieved by generating sequences in which the third position of one or more selected (or all) codons is substituted with mixed-base and/or deoxyinosine residues. The term nucleic acid is used interchangeably with gene, cDNA, mRNA, oligonucleotide, and polynucleotide. Batzer, et al., *Nucleic Acid Res.*, 19: 5081, 1991; Ohtsuka, et al., *J. Biol. Chem.*, 260: 2605-2608, 1985; Rossolini, et al., *Mol. Cell. Probes*, 8: 91-98, 1994.

"Polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

A "label" or a "detectable moiety" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe can be detected by detecting the presence of the label bound to the probe.

"Nucleic acid probe or oligonucleotide" refers to a nucleic acid capable of binding to a target nucleic acid of complementary sequence through one or more types of chemical bonds, usually through complementary base pairing, usually through hydrogen bond formation. As used herein, a probe can include natural (i.e., A, G, C, or T) or modified bases (7-deazaguanosine, inosine, and the like). In addition, the bases in a probe can be joined by a linkage other than a phosphodiester bond, so long as it does not interfere with hybridization. Thus, for example, probes can be peptide nucleic acids in which the constituent bases are joined by peptide bonds rather than phosphodiester linkages. It will be understood by one of skill in the art that probes can bind target sequences lacking complete complementarity with the probe sequence depending upon the stringency of the hybridization conditions. The probes are optionally directly labeled as with isotopes, chromophores, lumiphores, chromogens, or indirectly labeled such as with biotin to which a streptavidin complex can later bind. By assaying for the presence or absence of the probe, one can detect the presence or absence of the select sequence or subsequence.

"Promoter" refers to an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

"Expression vector" refers to a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

"Identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 86%, 87%, 88%, 89%, 90%, 91%, 92%, 93%, 94%, 95%, 96%, 97%, 98%, 99%, or higher identity over a specified region (e.g., the sequence of the naturally occurring EFHC1 or EFHC1a gene), when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This definition also refers to the compliment of a test sequence. The definition also includes sequences that have deletions and/or additions, as well as those that have substitutions. As described below, the preferred algorithms can account for gaps and the like. Preferably, the identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

"Comparison window" refers to a segment of any one of the number of contiguous positions selected from the group consisting of from 20 to 600, usually about 50 to about 200, more usually about 100 to about 150 in which a sequence can be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith, et al., *Adv. Appl. Math.,* 2: 482, 1991 by the homology alignment algorithm of Needleman, et al., *J. Mol. Biol.,* 48: 443, 1970, by the search for similarity method of Pearson, et al., *Proc. Nat'l. Acad. Sci. USA,* 85: 2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., CURRENT PROTOCOLS IN MOLECULAR BIOLOGY. Ausubel, et al., eds., supplement, 1995.

Another example of algorithm that is suitable for determining percent sequence identity and sequence similarity are the BLAST and BLAST 2.0 algorithms, which are described in Altschul, et al., *Nuc. Acids Res.,* 25: 3389-3402, 1977; Altschul, et al., *J. Mol. Biol.,* 215: 403-410, 1990, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA,* 89: 10915, 1989) alignments (B) of 50, expectation (E) of 10, M=5, N=−4, and a comparison of both strands. Altschul, et al., supra.

The BLAST algorithm also performs a statistical analysis of the similarity between two sequences (see, e.g., Karlin & Altschul, *Proc. Natl. Acad. Sci. USA,* 90: 5873-5787, 1993. One measure of similarity provided by the BLAST algorithm is the smallest sum probability (P(N)), which provides an indication of the probability by which a match between two nucleotide or amino acid sequences would occur by chance.

For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

"Selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

"Stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, 1993, "Overview of principles of hybridization and the strategy of nucleic acid assays" in TECHNIQUES IN BIOCHEMISTRY AND MOLECULAR BIOLOGY—HYBRIDIZATION WITH NUCLEIC PROBES. Generally, stringent conditions are selected to be about 5-10° C. lower than the thermal melting point ($T_M$) for the specific sequence at a defined ionic strength pH. The $T_M$ is the temperature (under defined ionic strength, pH, and nucleic concentration) at which 50% of the probes complementary to the target hybridize to the target sequence at equilibrium (as the target sequences are present in excess, at $T_M$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Such washes can be performed for 5, 15, 30, 60, 120, or more minutes. For PCR, a temperature of about 36° C. is typical for low stringency amplification, although annealing temperatures can vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min, an annealing phase lasting 30 sec.-2 min, and an extension phase of about 72° C. for 1-2 min.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such washes can be performed for 5, 15, 30, 60, 120, or more minutes. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to $V_H$-$C_{H1}$ by a disulfide bond. The F(ab)'2 can be reduced under mild conditions to break the disulfide linkage in the hinge region, thereby converting the F(ab)'2 dimer into an Fab' monomer. The Fab' monomer is essentially Fab with part of the hinge region (see FUNDAMENTAL IMMUNOLOGY (Paul Ed., 3$^{rd}$ Ed. 1993). While various antibody fragments are defined in terms of the digestion of an intact antibody, one of skill will appreciate that such fragments can be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty, et al., Nature, 348: 552-554, 1990).

For preparation of monoclonal or polyclonal antibodies, any technique known in the art can be used (see, e.g., Kohler & Milstein, Nature, 256: 495-497, 1975; Kozbor, et al., Immunology Today, 4: 72, 1983; Cole, et al., Monoclonal Antibodies and Cancer Therapy, pp. 77-96, 1985). Techniques for the production of single chain antibodies (U.S. Pat. No. 4,946,778) can be adapted to produce antibodies to polypeptides of this invention. Also, transgenic mice, or other organisms such as other mammals, can be used to express humanized antibodies. Alternatively, phage display technology can be used to identify antibodies and heteromeric Fab fragments that specifically bind to selected antigens (see, e.g., McCafferty, et al., Nature, 348: 552-554, 1990; Marks, et al., Biotechnology, 10: 779-783, 1992).

"Chimeric antibody" refers to an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

"Anti-EFHC1 or anti-EFHC1a" antibody refers to an antibody or antibody fragment that specifically binds a polypeptide encoded by an EFHC1 or EFHC1a gene, cDNA, or a subsequence thereof, e.g., the C-terminal domain.

"Immunoassay" refers to an assay that uses an antibody to specifically bind an antigen. The immunoassay is characterized by the use of specific binding properties of a particular antibody to isolate, target, and/or quantify the antigen.

"Specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions can require an antibody that is selected for its specificity for a particular protein. For example, polyclonal antibodies raised to an EFHC1 or EFHC1a polypeptide from specific species such as rat, mouse, or human can be selected to obtain only those polyclonal antibodies that are specifically immunoreactive with the EFHC1 or EFHC1a protein and not with other proteins, except for polymorphic variants and alleles of the EFHC1 or EFHC1a protein. This selection can be achieved by subtracting out antibodies that cross-react with EFHC1 or EFHC1a molecules from other species. A variety of immunoassay formats can be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual, 1998, for a description of immunoassay formats and conditions that can be used to determine specific immunoreactivity). Typically a specific or selective reaction will be at least twice background signal or noise and more typically more than 10 to 100 times background.

"Selectively associates with" refers to the ability of a nucleic acid to "selectively hybridize" with another as defined above, or the ability of an antibody to "selectively (or specifically) bind" to a protein, as defined above.

"Host cell" refers to a cell that contains an expression vector and supports the replication or expression of the expression vector. Host cells can be prokaryotic cells such as E. coli, or eukaryotic cells such as yeast, insect, amphibian, or mammalian cells such as CHO, HeLa and the like, e.g., cultured cells, explants, and cells in vivo.

"Detecting epilepsy" or "diagnosing epilepsy" refers to the ascertainment of the presence or absence of epilepsy in patient. "Detecting epilepsy" or "diagnosing epilepsy" can also refer to obtaining indirect evidence regarding the likelihood of the presence of cells in the patient that can cause epilepsy. Detecting epilepsy can be accomplished using the methods of this invention alone, in combination with other methods, or in light of other information regarding the state of health of the patient or subject.

"Therapeutically effective dose" refers to a dose that produces effects for which it is administered. The exact dose will depend on the purpose of the treatment, and will be ascertainable by one skilled in the art using known techniques (see, e.g., Lieberman, *Pharmaceutical Dosage Forms*, Vols. 1-3, 1992; Lloyd, *The Art, Science and Technology of Pharmaceutical Compounding*, 1999; Pickar, Dosage Calculations, 1999).

Detection of EFHC1 or EFHC1a Nucleic Acids

In numerous embodiments of the present invention, nucleic acids encoding an EFHC1 or EFHC1a polypeptide, including a full-length EFHC1 protein, myoclonin 1, or EFHC1a protein, myoclonin 2, or any derivative, variant, homolog, or fragment thereof, will be used. Such nucleic acids are useful for any of a number of applications, including for the production of EFHC1 or EFHC1a protein, for diagnostic assays, for therapeutic applications, for EFHC1 or EFHC1a-specific probes, for assays for EFHC1 or EFHC1a binding and/or modulating compounds, to identify and/or isolate EFHC1 or EFHC1a homologs from other species or from mice, and other applications.

General Recombinant DNA Methods

Numerous applications of the present invention involve the cloning, synthesis, maintenance, mutagenesis, and other manipulations of nucleic acid sequences that can be performed using routine techniques in the field of recombinant genetics. Basic texts disclosing the general methods of use in this invention include Sambrook et al., MOLECULAR CLONING, A LABORATORY MANUAL ($2^{nd}$ Ed. 1989); Kriegler, 1990, GENE TRANSFER AND EXPRESSION: A LABORATORY MANUAL; and CURRENT PROTOCOLS IN MOLECULAR BIOLOGY, 1995, (Ausubel et al., eds.).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage, et al., *Tetrahedron Letts.*, 22: 1859-1862, 1981, using an automated synthesizer, as described in Van Devanter, et al., *Nucleic Acids Res.*, 12: 6159-6168, 1984. Purification of oligonucleotides is by either native acrylamide gel electrophoresis or by anion-exchange HPLC as described in Pearson, et al., *J. Chrom.*, 255: 137-149, 1983.

The sequence of the cloned genes and synthetic oligonucleotides can be verified after cloning using, e.g., the chain termination method for sequencing double-stranded templates of Wallace, et al., *Gene*, 16: 21-26, 1981.

Isolating and Detecting EFHC1 or EFHC1a Nucleotide Sequences

In numerous embodiments of the present invention, EFHC1 or EFHC1a nucleic acids will be isolated and cloned using recombinant methods. Such embodiments are used, e.g., to isolate EFHC1 or EFHC1a polynucleotides for protein expression or during the generation of variants, derivatives, expression cassettes, or other sequences derived from EFHC1 or EFHC1a, to monitor EFHC1 or EFHC1a gene expression, for the determination of EFHC1 or EFHC1a sequences in various species, for diagnostic purposes in a patient, i.e., to detect mutations in EFHC1 or EFHC1a, or for genotyping and/or forensic applications.

Polymorphic variants, alleles, and interspecies homologs and nucleic acids that are substantially identical to the EFHC1 or EFHC1a gene can be isolated using EFHC1 or EFHC1a nucleic acid probes, and oligonucleotides by screening libraries under stringent hybridization conditions. Alternatively, expression libraries can be used to clone EFHC1 or EFHC1a protein, polymorphic variants, alleles, and interspecies homologs, by detecting expressed homologs immunologically with antisera or purified antibodies made against an EFHC1 or EFHC1a polypeptide, which also recognize and selectively bind to the EFHC1 or EFHC1a homolog.

To make a cDNA library, one should choose a source that is rich in ZFN217 RNA. The mRNA is then made into cDNA using reverse transcriptase, ligated into a recombinant vector, and transfected into a recombinant host for propagation, screening and cloning. Methods for making and screening cDNA libraries are well known (see, e.g., Gubler, et al., *Gene*, 25: 263-269, 1983; Sambrook, et al., supra, 1983; Ausubel, et al., supra, 1983.

For a genomic library, the DNA is extracted from the tissue and either mechanically sheared or enzymatically digested to yield fragments of about 12-20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton, et al., *Science*, 196: 180-182, 1977. Colony hybridization is carried out as generally described in Grunstein, et al., *Proc. Natl. Acad. Sci. USA.*, 72: 3961-3965, 1975.

More distantly related EFHC1 or EFHC1a homologs can be identified using any of a number of well known techniques, including by hybridizing an EFHC1 or EFHC1a probe with a genomic or cDNA library using moderately stringent conditions, or under low stringency conditions using probes from regions which are selective for EFHC1 or EFHC1a, e.g., specific probes generated to the C-terminal domain. Also, a distant homolog can be amplified from a nucleic acid library using degenerate primer sets, i.e., primers that incorporate all possible codons encoding a given amino acid sequence, in particular based on a highly conserved amino acid stretch. Such primers are well known to those of skill, and numerous programs are available, e.g., on the internet, for degenerate primer design.

In certain embodiments, EFHC1 or EFHC1a polynucleotides will be detected using hybridization-based methods to determine, e.g., EFHC1 or EFHC1a RNA levels or to detect particular DNA sequences, e.g., for diagnostic purposes. For example, gene expression of EFHC1 or EFHC1a can be analyzed by techniques known in the art, e.g., Northern blotting, reverse transcription and PCR amplification of mRNA, including quantitative PCR analysis of mRNA levels with real-time PCR procedures (e.g., reverse transcriptase-TAQ-MAN™ amplification), dot blotting, in situ hybridization, RNase protection, probing DNA microchip arrays, and the like.

In one embodiment, high density oligonucleotide analysis technology (e.g., GeneChip™) is used to identify orthologs, alleles, conservatively modified variants, and polymorphic variants of EFHC1 or EFHC1a, or to monitor levels of EFHC1 or EFHC1a mRNA. In the case where a homologs is linked to a known disease, they can be used with GeneChip™ as a diagnostic tool in detecting the disease in a biological sample, see, e.g., Gunthand, et al., *AIDS Res. Hum. Retroviruses*, 14: 869-876, 1998; Kozal, et al., *Nat. Med.*, 2: 753-759, 1996; Matson, et al., *Anal. Biochem.,* 224: 110-106, 1995; Lockhart, et al., *Nat. Biotechnol.,* 14: 1675-1680, 1996; Gingeras, et al., *Genome Res.,* 8: 435-448, 1998; Hacia, et al., *Nucleic Acids Res.,* 26: 3865-3866, 1998.

Detection of EFHC1 or EFHC1a polynucleotides and polypeptides can involve quantitative or qualitative detection of the polypeptide or polynucleotide, and can involve an actual comparison with a control value or, alternatively, can be performed so that the detection itself inherently indicates an increased level of EFHC1 or EFHC1a. The ZFN217 nucleic acids, polymorphic variants, orthologs, and alleles can modulate the expression, stability or activity of the naturally occurring EFHC1 or EFHC1a gene or other EFHC1 or EFHC1a family members, such that women with increased levels of protein have an increased risk of epilepsy, e.g., juvenile myoclonic epilepsy, discussed infra.

In certain embodiments, for example, diagnosis of epilepsy, the level of EFHC1 or EFHC1a polynucleotide, polypeptide, or protein activity will be quantified. In such embodiments, the difference between an elevated level of EFHC1 or EFHC1a and a normal, control level will preferably be statistically significant. Typically, a diagnostic presence, i.e., overexpression or an increase of EFHC1 or EFHC1a polypeptide or nucleic acid, represents at least about a 1.5, 2, 3, 5, 10, or greater fold increase in the level of EFHC1 or EFHC1a polypeptide or polynucleotide in the biological sample compared to a level expected in a non-epileptic sample. Detection of EFHC1 or EFHC1a can be performed in vitro, i.e., in cells within a biological sample taken from the patient, or in vivo. In one embodiment an increased level of EFHC1 or EFHC1a is used as a diagnostic marker of EFHC1 or EFHC1a. As used herein, a "diagnostic presence" indicates any level of EFHC1 or EFHC1a that is greater than that expected in a non-epileptic sample. In a one embodiment, assays for an EFHC1 or EFHC1a polypeptide or polynucleotide in a biological sample are conducted under conditions wherein a normal level of EFHC1 or EFHC1a polypeptide or polynucleotide, i.e., a level typical of a non-epileptic sample, i.e., epilepsy-free, would not be detected. In such assays, therefore, the detection of any EFHC1 or EFHC1a polypeptide or nucleic acid in the biological sample indicates a diagnostic presence, or increased level.

As described below, any of a number of methods to detect EFHC1 or EFHC1a can be used. A EFHC1 or EFHC1a polynucleotide level can be detected by detecting any EFHC1 or EFHC1a DNA or RNA, including EFHC1 or EFHC1a genomic DNA, mRNA, and cDNA. A EFHC1 or EFHC1a polypeptide can be detected by detecting an EFHC1 or EFHC1a polypeptide itself, or by detecting EFHC1 or EFHC1a protein activity. Detection can involve quantification of the level of EFHC1 or EFHC1a (e.g., genomic DNA, cDNA, mRNA, or protein level, or protein activity) or, alternatively, can be a qualitative assessment of the level, or of the presence or absence, of EFHC1 or EFHC1a, in particular in comparison with a control level. Any of a number of methods to detect any of the above can be used, as described infra. Such methods include, for example, hybridization, amplification, and other assays.

In certain embodiments, the ability to detect an increased level, or diagnostic presence, in a cell is used as a marker for neuronal cells in epileptic patients, i.e., to monitor the number or localization of neuronal cells in a patient, as detected in vivo or in vitro.

Typically, the EFHC1 or EFHC1a polynucleotides or polypeptides detected herein will be at least about 70% identical, and preferably 75%, 80%, 85%, 86%, 87%, 88%, 89%, 90%, 91%, 92%, 93%, 94%, 95%, 96%, 97%, 98%, 99% or more identical, over a region of at least about 50, 100, 200, or more nucleotides, or 20, 50, 100, or more amino acids, to the naturally occurring EFHC1 or EFHC1a gene. Such polynucleotides or polypeptides can represent functional or non-functional forms of EFHC1 or EFHC1a, or any variant, derivative, or fragment thereof.

Detection of Copy Number

In one embodiment, e.g., for the diagnosis or presence of epilepsy, the copy number, i.e., the number of EFHC1 or EFHC1a genes in a cell, is evaluated. Generally, for a given autosomal gene, an animal has two copies of each gene. The copy number can be increased, however, by gene amplification or duplication, e.g., in neuronal cells, or reduced by deletion. Methods of evaluating the copy number of a particular gene are well known to those of skill in the art, and include, inter alia, hybridization- and amplification-based assays.

Hybridization-based Assays: Any of a number of hybridization-based assays can be used to detect the EFHC1 or EFHC1a gene or the copy number of EFHC1 or EFHC1a genes in the cells of a biological sample. One such method is by Southern blot. In a Southern blot, genomic DNA is typically fragmented, separated electrophoretically, transferred to a membrane, and subsequently hybridized to an EFHC1 or EFHC1a-specific probe. For copy number determination, comparison of the intensity of the hybridization signal from the probe for the target region with a signal from a control probe for a region of normal genomic DNA (e.g., a nonamplified portion of the same or related cell, tissue, organ, and the like) provides an estimate of the relative EFHC1 or EFHC1a copy number. Southern blot methodology is well known in the art and is described, e.g., in Ausubel et al., or Sambrook et al., supra.

An alternative means for determining the copy number of EFHC1 or EFHC1a genes in a sample is by in situ hybridization, e.g., fluorescence in situ hybridization, or FISH. In situ hybridization assays are well known (e.g., Angerer, *Meth. Enzymol,* 152: 649, 1987). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization; and (5) detection of the hybridized nucleic acid fragments.

The probes used in such applications are typically labeled, e.g., with radioisotopes or fluorescent reporters. Preferred probes are sufficiently long, e.g., from about 50, 100, or 200 nucleotides to about 1000 or more nucleotides, so as to specifically hybridize with the target nucleic acid(s) under stringent conditions.

In numerous embodiments "comparative probe" methods, such as comparative genomic hybridization (CGH), are used to detect EFHC1 or EFHC1a gene amplification. In comparative genomic hybridization methods, a "test" collection of nucleic acids is labeled with a first label, while a second collection (e.g., from a healthy cell or tissue) is labeled with a second label. The ratio of hybridization of the nucleic acids is determined by the ratio of the first and second labels binding to each fiber in an array. Differences in the ratio of the signals from the two labels, e.g., due to gene amplification in the test collection, is detected and the ratio provides a measure of the EFHC1 or EFHC1a gene copy number.

Hybridization protocols suitable for use with the methods of the invention are described, e.g., in Albertson, *EMBO J.,* 3:

1227-1234, 1984; Pinkel, *Proc. Natl. Acad. Sci. U.S.A.,* 85: 9138-9142, 1988; EPO Pub. No. 430,402; METHODS IN MOLECULAR BIOLOGY, VOL. 33: In Situ Hybridization Protocols, Choo, Ed., 1994, Humana Press, Totowa, N.J., and the like.

Amplification-based Assays: In another embodiment, amplification-based assays are used to detect EFHC1 or EFHC1a or to measure the copy number of EFHC1 or EFHC1a genes. In such assays, the EFHC1 or EFHC1a nucleic acid sequences act as a template in an amplification reaction (e.g., Polymerase Chain Reaction, or PCR). In a quantitative amplification, the amount of amplification product will be proportional to the amount of template in the original sample. Comparison to appropriate controls provides a measure of the copy number of the EFHC1 or EFHC1a gene. Methods of quantitative amplification are well known to those of skill in the art. Detailed protocols for quantitative PCR are provided, e.g., in Innis, et al., *PCR Protocols: A Guide to Methods and Applications*, Academic Press, Inc. N.Y., 1990). The nucleic acid sequence for EFHC1 or EFHC1a is sufficient to enable one of skill to routinely select primers to amplify any portion of the gene.

In some embodiments, a TaqMan based assay is used to quantify EFHC1 or EFHC1a polynucleotides. TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, e.g., AmpliTaq, results in the cleavage of the TaqMan probe. This cleavage separates the 5' fluorescent dye and the 3' quenching agent, thereby resulting in an increase in fluorescence as a function of amplification (see, for example, literature provided by Perkin-Elmer, e.g., www.perkin-elmer.com).

Other suitable amplification methods include, but are not limited to, ligase chain reaction (LCR), transcription amplification, self-sustained sequence replication, dot PCR, and linker adapter PCR, etc. Wu, et al., *Genomics,* 4: 560, 1989; Landegren, et al., *Science,* 241: 1077, 1988; Barringer, et al., *Gene,* 89: 117, 1990; Kwoh, et al., *Proc. Natl. Acad. Sci. U.S.A.,* 86: 1173, 1989; Guatelli, et al., *Proc. Nat. Acad. Sci. U.S.A.,* 87: 1874, 1990.

Detection of EFHC1 or EFHC1a Expression

Direct hybridization-based assays: Methods of detecting and/or quantifying the level of EFHC1 or EFHC1a gene transcripts (mRNA or cDNA made therefrom) using nucleic acid hybridization techniques are known to those of skill in the art. Sambrook, et al., *Molecular Cloning: A Laboratory Manual,* 2D ED., VOLS 1-3, Cold Spring Harbor Press, New York, 1989.

For example, one method for evaluating the presence, absence, or quantity of EFHC1 or EFHC1a cDNA involves a Northern blot. In brief, in a typical embodiment, mRNA is isolated from a given biological sample, electrophoresed to separate the mRNA species, and transferred from the gel to a nitrocellulose membrane. Labeled EFHC1 or EFHC1a probes are then hybridized to the membrane to identify and/or quantify the mRNA.

Amplification-based assays: In another embodiment, an EFHC1 or EFHC1a transcript (e.g., EFHC1 or EFHC1a mRNA) is detected using amplification-based methods (e.g., RT-PCR). RT-PCR methods are well known to those of skill (see, e.g., Ausubel, et al., supra). Preferably, quantitative RT-PCR is used, thereby allowing the comparison of the level of mRNA in a sample with a control sample or value.

Detection of EFHC1 or EFHC1a Polypeptide Expression: In addition to the detection of EFHC1 or EFHC1a genes and gene expression using nucleic acid hybridization technology, EFHC1 or EFHC1a levels can also be detected and/or quantified by detecting or quantifying the polypeptide. EFHC1 or EFHC1a polypeptides are detected and quantified by any of a number of means well known to those of skill in the art. These include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like. EFHC1 or EFHC1a polypeptide detection is discussed in Section VI, infra.

Expression in Prokaryotes and Eukaryotes

In some embodiments, it is desirable to produce EFHC1 or EFHC1a polypeptides using recombinant technology. To obtain high level expression of a cloned gene or nucleic acid, such as a cDNA encoding an EFHC1 or EFHC1a polypeptide, an EFHC1 or EFHC1a sequence is typically subcloned into an expression vector that contains a strong promoter to direct transcription, a transcription/translation terminator, and if for a nucleic acid encoding a protein, a ribosome binding site for translational initiation. Suitable bacterial promoters are well known in the art and are described, e.g., in Sambrook, et al. and Ausubel, et al. Bacterial expression systems for expressing the EFHC1 or EFHC1a protein are available in, e.g., *E. coli, Bacillus* sp., and *Salmonella*. Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector. Palva, et al., *Gene,* 22: 229-235, 1983; Mosbach, et al., *Nature,* 302: 543-545, 1983.

For therapeutic applications, EFHC1 or EFHC1a nucleic acids are introduced into a cell, in vitro, in vivo, or ex vivo, using any of a large number of methods including, but not limited to, infection with viral vectors, liposome-based methods, biolistic particle acceleration (the gene gun), and naked DNA injection. Such therapeutically useful nucleic acids include, but are not limited to, coding sequences for full-length EFHC1 or EFHC1a, coding sequences for an EFHC1 or EFHC1a fragment, domain, derivative, or variant, EFHC1 or EFHC1a antisense sequences, and EFHC1 or EFHC1a ribozymes. Typically, such sequences will be operably linked to a promoter, but in numerous applications a nucleic acid will be administered to a cell that is itself directly therapeutically effective, e.g., certain antisense or ribozyme molecules.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the EFHC1- or EFHC1a-encoding nucleic acid in host cells. A typical expression cassette thus contains a promoter operably linked to the nucleic acid sequence encoding an EFHC1 or EFHC1a polypeptide, and signals required for efficient polyadenylation of the transcript, ribosome binding sites, and translation termination. The nucleic acid sequence encoding an EFHC1 or EFHC1a polypeptide can be linked to a cleavable signal peptide sequence to promote secretion of the encoded protein by the transfected cell. Such signal peptides would include, among others, the signal peptides from tissue plasminogen activator, insulin, and neuron growth factor, and juvenile hormone esterase of *Heliothis virescens*. Additional elements of the cassette can include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region can be obtained from the same gene as the promoter sequence or can be obtained from different genes.

The particular expression vector used to transport the genetic information into the cell is not particularly critical. Any of the conventional vectors used for expression in eukaryotic or prokaryotic cells can be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc, HA-tag, 6-His tag (SEQ ID NO: 21), maltose binding protein, VSV-G tag, anti-DYKDDDDK tag (SEQ ID NO: 22), or any such tag, a large number of which are well known to those of skill in the art.

Expression vectors containing regulatory elements from eukaryotic viruses are typically used in eukaryotic expression vectors, e.g., SV40 vectors, papilloma virus vectors, and vectors derived from Epstein-Ban virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification, such as neomycin, thymidine kinase, hygromycin B phosphotransferase, and dihydrofolate reductase. Alternatively, high yield expression systems not involving gene amplification are also suitable, such as using a baculovirus vector in insect cells, with a sequence encoding an EFHC1 or EFHC1a polypeptide under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary.

Standard transfection methods are used to produce bacterial, mammalian, yeast or insect cell lines that express large quantities of an EFHC1 or EFHC1a protein, which are then purified using standard techniques. Transformation of eukaryotic and prokaryotic cells are performed according to standard techniques. Colley, et al., *J. Biol. Chem.*, 264: 17619-17622, 1989; Deutscher, Ed, "Guide to Protein Purification," in METHODS IN ENZYMOLOGY, Vol. 182, 1990; Morrison, *J. Bact.*, 132: 349-351, 1977; Clark-Curtiss, et al., *Methods in Enzymology*, 101: 347-362, 1983; Wu, et al., eds.

Any of the well known procedures for introducing foreign nucleotide sequences into host cells can be used. These include the use of reagents such as Superfect (Qiagen), liposomes, calcium phosphate transfection, polybrene, protoplast fusion, electroporation, microinjection, plasmid vectors, viral vectors, biolistic particle acceleration (the gene gun), or any of the other well known methods for introducing cloned genomic DNA, cDNA, synthetic DNA or other foreign genetic material into a host cell. It is only necessary that the particular genetic engineering procedure used be capable of successfully introducing at least one gene into the host cell capable of expressing an EFHC1 or EFHC1a gene. Sambrook, et al., supra.

After the expression vector is introduced into the cells, the transfected cells are cultured under conditions favoring expression of the EFHC1 or EFHC1a polypeptide, which is recovered from the culture using standard techniques identified below. Methods of culturing prokaryotic or eukaryotic cells are well known and are taught, e.g., in Ausubel, et al., Sambrook, et al., and in Freshney, 1993, CULTURE OF ANIMAL CELLS, 3$^{rd}$ Ed., A Wiley-Liss Publication.

Any of the well known procedures for introducing foreign nucleotide sequences into host cells can be used to introduce a vector, e.g., a targeting vector, into cells. These include the use of reagents such as Superfect (Qiagen), liposomes, calcium phosphate transfection, polybrene, protoplast fusion, electroporation, microinjection, plasmid vectors, viral vectors, biolistic particle acceleration (the gene gun), or any of the other well known methods for introducing cloned genomic DNA, cDNA, synthetic DNA or other foreign genetic material into a host cell (see, e.g., Sambrook, et al., supra). For the generation of a transgenic cell, it is only necessary that the particular genetic engineering procedure used be capable of successfully introducing at least one transgene into at least one host cell, which can then be selected using standard methods. Methods of culturing prokaryotic or eukaryotic cells are well known and are taught, e.g., in Ausubel, et al., Sambrook, et al., 1993, and in Freshney, CULTURE OF ANIMAL CELLS, 3$^{rd}$ Ed., A Wiley-Liss Publication.

EFHC1 or EFHC1a Transgenic Animals

The present invention provides transgenic and chimeric nonhuman mammals comprising one or more functionally and structurally disrupted EFHC1 or EFHC1a alleles. Alternatively, extra gene copies of EFHC1 or EFHC1a in a transgenic animal can increase levels of EFHC1 or EFHC1a polynucleotides or EFHC1 or EFHC1a polypeptides in the transgenic animal. A "chimeric animal" includes some cells that lack the functional EFHC1 or EFHC1a gene of interest and other cells that do not have the inactivated gene. A "transgenic animal," in contrast, is made up of cells that have all incorporated the specific modification which renders the EFHC1 or EFHC1a gene inactive or otherwise altered.

While a transgenic animal is typically always capable of transmitting the mutant EFHC1 or EFHC1a gene to its progeny, the ability of a chimeric animal to transmit the mutation depends upon whether the inactivated gene is present in the animal's germ cells. The modifications that inactivate or otherwise alter the EFHC1 or EFHC1a gene can include, for example, insertions, deletions, or substitutions of one or more nucleotides. The modifications can interfere with transcription of the gene itself, with translation and/or stability of the resulting mRNA, or can cause the gene to encode an inactive or otherwise altered EFHC1 or EFHC1a polypeptide, e.g., an EFHC1 or EFHC1a polypeptide with modified binding properties. In particular, the present transgenic and chimeric animals can lack coding sequences for one or more components of an EFHC1 or EFHC1a polypeptide, such as the one or more zinc finger binding domains, heterologous protein binding domains. Such transgenes can thus eliminate any one or more codons within an endogenous EFHC1 or EFHC1a allele. In a preferred embodiment, a transgenic animal has an allele that lacks at least 10, 20, 30, or more codons of the full-length protein. Further, a transgenic animal can lack non-coding sequences that are required for EFHC1 or EFHC1a expression or function, such as 5' or 3' regulatory sequences.

Transgenic animals and cells derived from these animals can be used to test compounds as modulators of an EFHC1 or EFHC1a protein screening and testing assays described below. In this regard, transgenic animals and cells lines capable of expressing wildtype or mutant EFHC1 or EFHC1a can be exposed to test agents. These test agents can be screened for the ability to reduce overexpression of wildtype EFHC1 or EFHC1a or impair the expression or function of mutant EFHC1 or EFHC1a.

Methods of obtaining transgenic animals are described in, for example, PCT Publication No. WO 01/30798, Puhler, A., Ed., 1993, GENETIC ENGINEERING OF ANIMALS, VCH Publ.; Murphy and Carter, eds., 1993, TRANSGENESIS TECHNIQUES: PRINCIPLES AND PROTOCOLS (Methods in Molecular Biology, Vol. 18); and Pinkert, CA, Ed., TRANSGENIC ANIMAL TECHNOLOGY: A LABORATORY HANDBOOK, 1994, Academic Press.

Typically, a modified EFHC1 or EFHC1a gene is introduced, e.g., by homologous recombination, into embryonic stem cells (ES), which are obtained from preimplantation embryos and cultured in vitro. See, e.g., Hooper, M L, 1993, EMBRYONAL STEM CELLS: INTRODUCING PLANNED CHANGES INTO THE ANIMAL GERMLINE (Modern Genetics, Vol. 1), Int'l. Pub. Distrib., Inc.; Bradley, et al., *Nature*, 309: 255-258, 1984. Subsequently, the transformed ES cell is combined with a blastocyst from a nonhuman animal, e.g., a mouse. The ES cells colonize the embryo and in some embryos form the germ line of the resulting chimeric animal. Alternatively, ES cells or somatic cells that can reconstitute an organism ("somatic repopulating cells") can be used as a source of nuclei for transplantation into an enucleated fertilized oocyte giving rise to a transgenic mammal. Jaenisch, *Science*, 240: 1468-1474, 1988; Wilmut, et al., *Nature*, 385: 810-813, 1997.

Other methods for obtaining a transgenic or chimeric animal having a mutant EFHC1 or EFHC1a gene in its genome is to contact fertilized oocytes with a vector that includes a polynucleotide that encodes a modified, e.g., inactive, EFHC1 or EFHC1a polypeptide. In some animals, such as mice, fertilization is typically performed in vivo and fertilized ova are surgically removed. In other animals, particularly bovines, it is preferable to remove ova from live or slaughterhouse animals and fertilize the ova in vitro. See, DeBoer, et al., WO 91/08216. In vitro fertilization permits the modifications to be introduced into substantially synchronous cells.

Fertilized oocytes are typically cultured in vitro until a pre-implantation embryo is obtained containing about 16-150 cells. The 16-32 cell stage of an embryo is described as a morula, whereas pre-implantation embryos containing more than 32 cells are termed blastocysts. These embryos show the development of a blastocoel cavity, typically at the 64 cell stage. The presence of a desired EFHC1 or EFHC1a mutation in the cells of the embryo can be detected by methods known to those of skill in the art, e.g., Southern blotting, PCR, DNA sequencing, or other standard methods. Methods for culturing fertilized oocytes to the pre-implantation stage are described, e.g., by Gordon, et al., *Methods Enzymol.*, 101: 414, 1984; Hogan, et al., MANIPULATION OF THE MOUSE EMBRYO: A LABORATORY MANUAL, C.S.H.L. N.Y. (mouse embryo), 1986; Hammer, et al., *Nature*, 315: 680, 1985 (rabbit and porcine embryos); Gandolfi, et al., *J. Reprod. Fert.*, 81: 23-28, 1987; Rexroad, et al., *J. Anim. Sci.*, 66: 947-953 (ovine embryos), 1988; Eyestone, et al., *J. Reprod. Fert.*, 85: 715-720, 1989; Camous, et al., *J. Reprod. Fert.*, 72: 779-785, 1984; Heyman, et al., *Theriogenology*, 27: 5968 (bovine embryos), 1987. Pre-implantation embryos can also be stored frozen for a period pending implantation.

Pre-implantation embryos are transferred to an appropriate female resulting in the birth of a transgenic or chimeric animal, depending upon the stage of development when the transgene is integrated Chimeric mammals can be bred to form true germline transgenic animals Chimeric mice and germline transgenic mice can also be ordered from commercial sources (e.g., Deltagen, San Carlos, Calif.).

Other methods for introducing mutations into mammalian cells or animals include recombinase systems, which can be employed to delete all or a portion of a locus of interest. Examples of recombinase systems include, the cre/lox system of bacteriophage P1 (see, e.g., Gu, et al., *Science*, 265: 103-106, 1994; Terry, et al., *Transgenic Res.*, 6: 349-356, 1997) and the FLP/FRT site specific integration system (see, e.g., Dymecki, *Proc. Natl. Acad. Sci. U.S.A.*, 93: 6191-6196, 1996). In these systems, sites recognized by the particular recombinase are typically introduced into the genome at a position flanking the portion of the gene that is to be deleted. Introduction of the recombinase into the cells then catalyzes recombination which deletes from the genome the polynucleotide sequence that is flanked by the recombination sites. If desired, one can obtain animals in which only certain cell types lack the EFHC1 or EFHC1a gene of interest, e.g., by using a tissue specific promoter to drive the expression of the recombinase. Tsien, et al., *Cell*, 87: 1317-26, 1996; Brocard, et al., *Proc. Natl. Acad. Sci. U.S.A.*, 93: 10887-10890, 1996; Wang, et al., *Proc. Natl. Acad. Sci. U.S.A.*, 93: 3932-6, 1996; Meyers, et al., *Nat. Genet.*, 18: 136-41, 1998.

The presence of any mutation in an EFHC1 or EFHC1a gene in a cell or animal can be detected using any method described herein, e.g., Southern blot, PCR, DNA sequencing, or using assays based on any EFHC1 or EFHC1a-dependent cell or organismal property or behavior. See, e.g., Ausubel et al., supra.

Purification of EFHC1 or EFHC1a Polypeptides

Either naturally occurring or recombinant EFHC1 polypeptide, myoclonin1, or EFHC1a polypeptide, myoclonin 2, can be purified for use in functional assays, binding assays, diagnostic assays, and other applications. Naturally occurring EFHC1 or EFHC1a polypeptides are purified, e.g., from mammalian tissue such as blood, lymphatic tissue, or any other source of an EFHC1 or EFHC1a homolog. Recombinant EFHC1 or EFHC1a polypeptides are purified from any suitable bacterial or eukaryotic expression system, e.g., CHO cells or insect cells.

EFHC1 or EFHC1a proteins can be purified to substantial purity by standard techniques, including, but not limited to selective precipitation with such substances as ammonium sulfate; column chromatography, immunopurification methods, and others (see, e.g., Scopes, 1993, PROTEIN PURIFICATION: PRINCIPLES AND PRACTICE; U.S. Pat. No. 4,673,641; Ausubel et al., supra; and Sambrook et al., supra).

A number of procedures can be employed when recombinant EFHC1 or EFHC1a polypeptide is being purified. For example, proteins having established molecular adhesion properties can be reversibly fused to the EFHC1 or EFHC1a polypeptide. With the appropriate ligand, an EFHC1 or EFHC1a polypeptide can be selectively adsorbed to a purification column and then freed from the column in a relatively pure form. The fused protein is then removed by enzymatic activity. EFHC1 or EFHC1a proteins can also be purified using immunoaffinity columns.

Purification of Recombinant EFHC1 or EFHC1a Protein: Recombinant proteins are expressed by transformed bacteria or eukaryotic cells such as CHO cells or insect cells in large amounts, typically after promoter induction but expression can be constitutive. Promoter induction with IPTG is one example of an inducible promoter system. Cells are grown according to standard procedures in the art. Fresh or frozen cells are used for isolation of protein.

Proteins expressed in bacteria can form insoluble aggregates ("inclusion bodies"). Several protocols are suitable for purification of EFHC1 or EFHC1a inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies can be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate) and 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation can occur upon removal (by dialysis, for example) or dilution of the denaturant, allowing re-formation of immunologically and/or biologically active protein. Other suitable buffers are known to those skilled in the art. EFHC1 or EFHC1a polypeptides are separated from other bacterial proteins by standard separation techniques, e.g., with Ni-NTA agarose resin.

Alternatively, it is possible to purify EFHC1 or EFHC1a polypeptides from bacteria periplasm. After lysis of the bacteria, when an EFHC1 or EFHC1a protein is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

Standard Protein Separation Techniques for Purifying EFHC1 or EFHC1a Polypeptides: Often as an initial step, particularly if the protein mixture is complex, an initial salt fractionation can separate many of the unwanted host cell proteins (or proteins derived from the cell culture media) from the recombinant protein of interest. The preferred salt is ammonium sulfate Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

The molecular weight of an EFHC1 or EFHC1a protein can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

EFHC1 or EFHC1a proteins can also be separated from other proteins on the basis of their size, net surface charge, hydrophobicity, and affinity for heterologous molecules. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Diagnosing Epilepsy

The present invention provides numerous methods for diagnosing any of a number of types of epilepsy, e.g., determining whether or not a patient has epilepsy, whether or not a biological sample contains neuronal cells prone to epilepsy, estimating the likelihood of a patient developing epilepsy, and monitoring the efficacy of anti-epileptic treatment in a patient with epilepsy. Such methods are based on the discovery that neuronal cells prone to epilepsy have a reduced level of EFHC1 or EFHC1a polynucleotide (i.e., gene copy number and/or mRNA) and polypeptide level. Accordingly, by determining whether or not a cell contains reduced levels of EFHC1 or EFHC1a polynucleotide or EFHC1 or EFHC1a polypeptide, e.g., myoclonin 1 or myoclonin 2, it is possible to determine whether or not the patient is prone to epilepsy. Further, the presence of such cells can be determined indirectly, i.e., in certain embodiments a biological sample that does not itself contain cells prone to epilepsy, but which has been taken from an animal with cells elsewhere in its body, can contain reduced levels of EFHC1 or EFHC1a reflecting the presence of the cells prone to epilepsy.

Detecting Epilepsy

In numerous embodiments of the present invention, the level and/or presence or EFHC1 or EFHC1a polynucleotide or polypeptide (or allelic variants thereof) will be detected in a biological sample, thereby detecting the presence or absence of neuronal cells prone to epilepsy in the biological sample, or, in certain embodiments, in the patient from which the biological sample was removed. In preferred embodiments, the biological sample will comprise a tissue sample from a tissue suspected of containing neuronal cells prone to epilepsy. For example, in a patient suspected of having epilepsy, neuronal tissue is removed. Often, such methods will be used in conjunction with additional diagnostic methods, e.g., detection of other epilepsy markers, mammography, and the like. In other embodiments, a tissue sample known to contain c neuronal cells prone to epilepsy, e.g., juvenile myoclonic epilepsy, will be detected for EFHC1 or EFHC1a levels to determine information about the epilepsy, e.g., the efficacy of certain treatments, the survival expectancy of the animal, and the like.

The amount of EFHC1 or EFHC1a polynucleotide or polypeptide that will indicate the presence of epilepsy will depend on numerous factors, including the type of epilepsy, the age, sex, medical history, and the like, of the patient, the cell type, the assay format, and the like In preferred embodiments, a level of EFHC1 or EFHC1a in a biological sample will not be quantified or directly compared with a control sample, but will rather be detected relative to a "diagnostic presence" of EFHC1 or EFHC1a, wherein a "diagnostic presence" refers to an amount of EFHC1 or EFHC1a polynucleotide or polypeptide that indicates the presence of epilepsy, or indicates a likelihood of epilepsy, in the patient from which the sample was taken. Preferably, a "diagnostic presence" will be detectable in a simple assay giving a positive or negative result, where a positive "detection" of a "diagnostic presence" of EFHC1 or EFHC1a polynucleotide or polypeptide indicates the presence of epilepsy in the patient.

The EFHC1 or EFHC1a level need not be quantified for a "diagnostic presence" to be detected, merely any method of determining whether EFHC1 or EFHC1a is present at levels higher than in a normal, epilepsy-free cell, sample, or mammal. In addition, a "diagnostic presence" does not refer to any absolute quantity of EFHC1 or EFHC1a, but rather on an amount that, depending on the biological sample, cell type, assay conditions, medical condition of the patient, and the like, is sufficient to distinguish the level in a epilepsy, or pre-epilepsy sample, from a normal, epilepsy-free sample.

Such methods can be practiced regardless of whether any EFHC1 or EFHC1a polynucleotide or polypeptide is normally present, or "expected" to be present, in a particular control sample. For example, EFHC1 or EFHC1a may not be expressed in certain cell types, resulting in a complete absence of EFHC1 or EFHC1a in a control biological sample consisting of such cell types. For such biological sample, a "diagnostic presence" refers to any detectable amount of EFHC1 or EFHC1a, using any assay. In other tissues, however, there may be a detectable level of EFHC1 or EFHC1a present in normal, epilepsy-free cells, and a "diagnostic presence" represents a level that is higher than the normal level, preferably representing a "statistically significant" increase over the normal level. Often, as discussed supra, a "diagnostic presence" of EFHC1 or EFHC1a polynucleotide, polypeptide, and/or protein activity in a biological sample will be at least about 1.5, 2, 5, 10, or more fold greater than a level expected in a sample taken from a normal, epilepsy-free patient.

Further, the present methods can be used to assess the efficacy of a course of treatment. For example, in a patient with epilepsy from which a biological sample has been found to contain an reduced amount of EFHC1 or EFHC1a polynucleotide or polypeptide, the efficacy of an anti-epilepsy treatment can be assessed by monitoring, over time, EFHC1 or EFHC1a levels. For example, a reduction in EFHC1 or EFHC1a polynucleotide or polypeptide levels in a biological sample taken from a patient following a treatment, compared to a level in a sample taken from the patient before, or earlier in, the treatment, indicates efficacious treatment.

In one embodiment, a cytotoxicity assay provides pre-calibrated ELISA reagents for the detection of IgG antibody to EFHC1 and EFHC1a antigens in human serum. Defined amounts of affinity-purified EFHC1 and EFHC1a antigens are presented in different wells of a Terasaki tray. The specific binding of antibody from the test sample with any of these antigens is detected by a subsequent incubation with alkaline phosphatase-conjugated antibody that recognizes only human IgG. A quantitative measure of the extent of reaction is obtained by spectrophotometric determination following the addition of the appropriate enzyme substrate for the development of color. Qualitative assessment of antibody specificity is performed by analysis of the cytotoxicity assay reactivity pattern using the appropriate standards and controls.

Determining a Prognosis

The level of EFHC1 or EFHC1a or allelic variants thereof can be used to determine the prognosis of a patient with epilepsy. For example, if epilepsy is detected using a technique other than by detecting EFHC1 or EFHC1a, e.g., tissue biopsy, then the presence or absence of EFHC1 or EFHC1a can be used to determine the prognosis for the patient, i.e., a reduced level of EFHC1 or EFHC1a will indicate a reduced survival expectancy in the patient compared to in a patient with epilepsy but with a normal level of EFHC1 or EFHC1a. As used herein, "survival expectancy" refers to a prediction regarding the severity, duration, or progress of a disease, condition, or any symptom thereof. In a preferred embodiment, an increased level, a diagnostic presence, or a quantified level, of EFHC1 or EFHC1a is statistically correlated with the observed progress of a disease, condition, or symptom in a large number of patients, thereby providing a database wherefrom a statistically-based prognosis can be made in view of any detected level or presence of EFHC1 or EFHC1a. For example, in a particular type of patient, i.e., a human of a particular age, gender, medical condition, medical history, and the like, a detection of a level of EFHC1 or EFHC1a that is, e.g., 2 fold higher than a control level may indicate, e.g., a 10% reduced survival expectancy in the human compared to in a similar human with a normal level of EFHC1 or EFHC1a, based on a previous study of the level of EFHC1 or EFHC1a in a large number of similar patients whose disease progression was observed and recorded.

Determining a Preferred Course of Treatment

The present methods can be used to determine the optimal course of treatment in a patient with epilepsy. For example, the presence of a reduced level of EFHC1 or EFHC1a can indicate a reduced survival expectancy of a patient with epilepsy, thereby indicating a more aggressive treatment for the patient. In addition, a correlation can be readily established between levels of EFHC1 or EFHC1a, or the presence or absence of a diagnostic presence of EFHC1 or EFHC1a, and the relative efficacy of one or another anti-epilepsy agent. Such analyses can be performed, e.g., retrospectively, i.e., by detecting EFHC1 or EFHC1a levels in samples taken previously from patients that have subsequently undergone one or more types of anti-epilepsy therapy, and correlating the EFHC1 or EFHC1a levels with the known efficacy of the treatment.

In numerous embodiments, levels of EFHC1 or EFHC1a polynucleotides or polypeptides in neuronal cells of a patient, e.g., as detected by immunoassay using anti-EFHC1 or EFHC1a antibodies, are used to guide the selection of an anti-epilepsy treatment based on the effects of the treatment EFHC1 or EFHC1a or its activity. In preferred embodiments, a detection of a reduced or diagnostic level of EFHC1 or EFHC1a indicates the beneficial use of a treatment that inhibits the activity of EFHC1 or EFHC1a allelic variants thereof.

Treatment Regimes

The invention provides pharmaceutical compositions comprising one or a combination of EFHC1, EFHC1 agonists, or EFHC1 analogs or EFHC1a, EFHC1a agonists, or EFHC1a analogs with anti-epilepsy activity, formulated together with a pharmaceutically acceptable carrier. Some compositions include a combination of multiple (e.g., two or more) EFHC1, EFHC1 agonists, or EFHC1 analogs or EFHC1a, EFHC1a agonists, or EFHC1a analogs of the invention.

In prophylactic applications, pharmaceutical compositions or medicaments of EFHC1, EFHC1 agonists, or EFHC1 analogs or EFHC1a, EFHC1a agonists, or EFHC1a analogs are administered to a patient susceptible to, or otherwise at risk of a disease or condition (e.g., epilepsy disease) in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. In therapeutic applications, EFHC1, EFHC1 agonist, or EFHC1 analog or EFHC1a, EFHC1a agonists, or EFHC1a analogs compositions or medicants are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease. An amount adequate to accomplish therapeutic or prophylactic treatment is defined as a therapeutically- or prophylactically-effective dose. In both prophylactic and therapeutic regimes, agents are usually administered in several dosages until a sufficient prophylactic or therapeutic response has been achieved. Typically, the prophylactic or therapeutic response is monitored and repeated dosages are given if the response starts to wane.

EFHC1, EFHC1 agonists, or EFHC1 analogs or EFHC1a, EFHC1a agonists, or EFHC1a analogs, useful in the present compositions and methods can be administered to a human patient per se, in the form of a prodrug, pharmaceutically acceptable salt, hydrate, solvate, acid salt hydrate, N-oxide or isomorphic crystalline form thereof, or in the form of a pharmaceutical composition where the compound is mixed with suitable carriers or excipient(s) in a therapeutically effective amount.

Pharmaceutically acceptable carriers are determined in part by the particular composition being administered, as well as by the particular method used to administer the composition. Accordingly, there is a wide variety of suitable formulations of pharmaceutical compositions for administering the EFHC1, EFHC1 agonist, or EFHC1 analog or EFHC1a, EFHC1a agonists, or EFHC1a analogs compositions (see, e.g., *Remington's Pharmaceutical Sciences*, Mack Publishing Co., Easton, Pa. 18$^{th}$ ed., 1990, incorporated herein by reference). The pharmaceutical compositions generally comprise an EFHC1, EFHC1 agonists, or EFHC1 analogs in a form suitable for administration to a patient. The pharmaceutical compositions are generally formulated as sterile, substantially isotonic and in full compliance with all Good Manufacturing Practice (GMP) regulations of the U.S. Food and Drug Administration.

Effective Dosages

Effective doses of the EFHC1, EFHC1 agonists, or EFHC1 analogs or EFHC1a, EFHC1a agonists, or EFHC1a analogs with anti-epilepsy activity described herein vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy.

For administration with a pharmaceutical composition comprising EFHC1, EFHC1 agonists, or EFHC1 analogs or EFHC1a, EFHC1a agonists, or EFHC1a analogs, the dosage ranges from about 0.0001 to 100 mg/kg, usually from about 0.01 to 40 mg/kg, and more usually from about 0.1 to about 20 mg/kg, of the host body weight. For example dosages can be 1 mg/kg body weight or 10 mg/kg body weight or within the range of 1-10 mg/kg. In some methods, two or more EFHC1, EFHC1 agonists, or EFHC1 analogs or EFHC1a, EFHC1a agonists, or EFHC1a analogs with different binding specificities are administered simultaneously, in which case the dosage of each EFHC1, EFHC1 agonist, or EFHC1 analog or EFHC1a, EFHC1a agonists, or EFHC1a analogs thereof administered falls within the ranges indicated. EFHC1, EFHC1 agonist, or EFHC1 analog or EFHC1a, EFHC1a agonists, or EFHC1a analogs compositions are usually administered on multiple occasions. Intervals can be irregular as indicated by measuring blood levels of EFHC1, EFHC1 agonists, or EFHC1 analogs or EFHC1a, EFHC1a agonists, or EFHC1a analogs thereof in the patient. In some methods, dosage is adjusted to achieve a plasman EFHC1, EFHC1 agonist, or EFHC1 analog or EFHC1a, EFHC1a agonists, or EFHC1a analogs concentration of 1-100 µg/ml. Alternatively, EFHC1, EFHC1 agonists, or EFHC1 analogs or EFHC1a, EFHC1a agonists, or EFHC1a analogs can be administered as a sustained release formulation, in which case less frequent administration is required. Dosage and frequency vary depending on the half-life of the EFHC1, EFHC1 agonists, or EFHC1 analogs or EFHC1a, EFHC1a agonists, or EFHC1a analogs in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime of effective doses of the pharmaceutical composition comprising EFHC1, EFHC1 agonists, or EFHC1 analogs or EFHC1a, EFHC1a agonists, or EFHC1a analogs.

Routes of Administration

EFHC1, EFHC1 agonists, or EFHC1 analogs or EFHC1a, EFHC1a agonists, or EFHC1a analogs with anti-epilepsy activity, formulated together with a pharmaceutically acceptable carrier, can be administered by parenteral, topical, intravenous, oral, subcutaneous, intraarterial, intracranial, intraperitoneal, intranasal, intramuscular means, or as inhalants. The most typical routes of administration of an EFHC1, EFHC1 agonists, or EFHC1 analogs or EFHC1a, EFHC1a agonists, or EFHC1a analogs is subcutaneous or intravenous, although other routes can be equally effective. The next most common route is parenteral. In some methods, agents are injected directly into a particular tissue where tumors have developed. In some methods, EFHC1, EFHC1 agonists, or EFHC1 analogs or EFHC1a, EFHC1a agonists, or EFHC1a analogs are administered as a sustained release composition or device, such as a Medipad™ device.

Agents of the invention can optionally be administered in combination with other agents that are at least partly effective in treating various diseases. For example, in the case of epilepsy, agents of the invention can also be administered in conjunction with other agents that increase passage of the agents of the invention across the blood-brain barrier (BBB). Another example would include treating patients with a known anti-epilepsy agent along with the agent of the invention (combination therapy).

Formulation

EFHC1, EFHC1 agonists, or EFHC1 analogs or EFHC1a, EFHC1a agonists, or EFHC1a analogs with anti-epilepsy activity, are often administered as pharmaceutical compositions comprising an active therapeutic agent, and a variety of other pharmaceutically acceptable components. See Remington's Pharmaceutical Science, 1990 supra. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation can also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, compositions of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

The agents of this invention can be administered in the form of a depot injection or implant preparation which can be formulated in such a manner as to permit a sustained or pulsatile release of the active ingredient.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990; and Hanes, Advanced Drug Delivery Reviews 28: 97-119, 1997.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins. Glenn et al., Nature 391: 851, 1998. Co-administration can be achieved by using the components as a mixture.

Alternatively, transdermal delivery can be achieved using a skin patch or using transferosomes. Paul et al., Eur. J. Immunol. 25: 3521-24, 1995; Cevc et al., Biochem. Biophys. Acta 1368: 201-15, 1998.

The pharmaceutical compositions are generally formulated as sterile, substantially isotonic and in full compliance with all Good Manufacturing Practice (GMP) regulations of the U.S. Food and Drug Administration.

Toxicity

A therapeutically effective dose of the EFHC1, EFHC1 agonists, or EFHC1 analogs or EFHC1a, EFHC1a agonists, or EFHC1a analogs described herein will provide therapeutic benefit without causing substantial toxicity.

Toxicity of the proteins described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the EFHC1, EFHC1 agonists, or EFHC1 analogs or EFHC1a, EFHC1a agonists, or EFHC1a analogs, described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, Ch. 1, Kits Also within the scope of the invention are kits comprising the compositions (e.g., EFHC1, EFHC1 agonists, or EFHC1 analogs, or EFHC1a, EFHC1a agonists, or EFHC1a analogs) of the invention and instructions for use. The kit can further contain a least one additional reagent, or one or more additional EFHC1, EFHC1 agonists, or EFHC1 analogs, or EFHC1a, EFHC1a agonists, or EFHC1a analogs of the invention. Kits typically include a label indicating the intended use of the contents of the kit. The term label includes any writing, or recorded material supplied on or with the kit, or which otherwise accompanies the kit.

EXEMPLARY EMBODIMENTS

Example 1

Structure and Expression of EFHC1

18 genes were identified in the narrowed 3.5 cM region at 6p12-p11, and all except EFHC1 were excluded as the JME gene by mutation analyses (ref. 10 and T. S. et al., unpublished data). EFHC1 is located between the markers D6S1960 and D6S1024, spans approximately 72 kb, and encodes a protein of 640 amino acids. A domain search revealed three DM10 domains, a motif with unknown function, and an EF-hand, a $Ca^{2+}$ binding motif (FIG. 1a). The EFHC1 transcripts undergo alternative splicing in exon 4, which result in a C-terminal truncated protein. Northern analysis confirmed that both transcripts were expressed and detected in various human tissues including brain (FIG. 1c), but not expressed in lymphocytes as confirmed by RT-PCR. A partial cDNA clone was also identified that corresponded to the 7 kb and 9 kb transcripts observed on northern blots. These longer transcripts could contain structures of transcript B with its extended 3'-UTR as they were detected by probes 2 and 4 (FIG. 1 b,c). A mouse orthologue of EFHC1, named Efhc1, was isolated and investigated for expression by RT-PCR and northern blot analyses. A 2.3 kb Efhc1 transcript appeared on northern blots, however the analyses hardly detected any larger transcripts that were observed in human. A polyclonal anti-EFHC1 antibody was raised that recognizes amino acid residues 522-533 of both human and murine EFHC1 proteins and their expression was investigated (FIG. 1d-i). Double-staining of mouse primary culture neurons with the anti-EFHC1 antibody and anti-MAP2 (dendrite marker) or anti-phosphorylated neurofilament (axon marker) antibodies showed that Efhc1 localized at soma and dendrites of neurons (FIG. 1d-f), but Efhc1 signal was not observed at axon Immunohistochemistry of mouse brain sections revealed Efhc1 signals in soma and dendrites of pyramidal neurons of hippocampus CA1 region (FIG. 1g), pyramidal neurons of cerebral cortex (FIG. 1h) and purkinje cells of cerebellum (FIG. 1i). Bai, et al., *Am. J. Med. Genet.*, 133: 268-274, 2002; Braunewell, et al., *Cell Tissue Res.*, 295: 1-12, 1999.

FIG. 1a shows a schematic diagram of EFHC1 protein (encoded by the transcript A). FIG. 1b shows a schematic diagrams of the EFHC1 isoforms, consensus transcript A (AK001328), transcript B (AL122084) and an EST clone (AY608689). Coding regions are shown in open boxes and presumptive untranslated regions are blackened. A vertical line in transcript A indicates the EF-hand domain. Relative positions of the probes used for the northern blot analyses are shown on the top. Note that the probe 2 is specific for transcript B. FIG. 1c shows Northern-blot analyses of EFHC1 on human adult tissues using probes 1, 2, 3, and 4. Signals obtained for control β-actin (for probe 1, 2, 4 panels) or G3PDH (for probe 3 panel) probes are shown in lower panels. FIG. 1d-f show hippocampal primary culture neurons (6 days in vitro) from E16 mouse were double-stained with anti-EFHC1 (d) and anti-MAP2 (e) antibodies. Signals of Efhc1 and MAP2 mostly overlap (f). FIG. 1g-i show adult mouse brain sections were stained with anti-EFHC1 antibody. (g) Hippocampal CA1 region. Soma and dendrites of pyramidal neurons show signals. O: stratum oriens, P: stratum pyramidal, R: stratum radiatum. FIG. 1h shows layer III of cerebral cortex. Soma and dendrites of neurons show signals (arrows). FIG. 1i shows cerebellum. Dendrites of Purkinje cells show intense signals (arrowheads). sg: stratum gangliosum, sgr: stratum granulosum, sm: stratum moleculare. Results of control stainings with pre-immune rabbit serum or serum pre-absorbed with EFHC1 peptide.

Example 2

EFHC1 Mutations Segregating with Epilepsy Traits in JME Families

Figure 2:
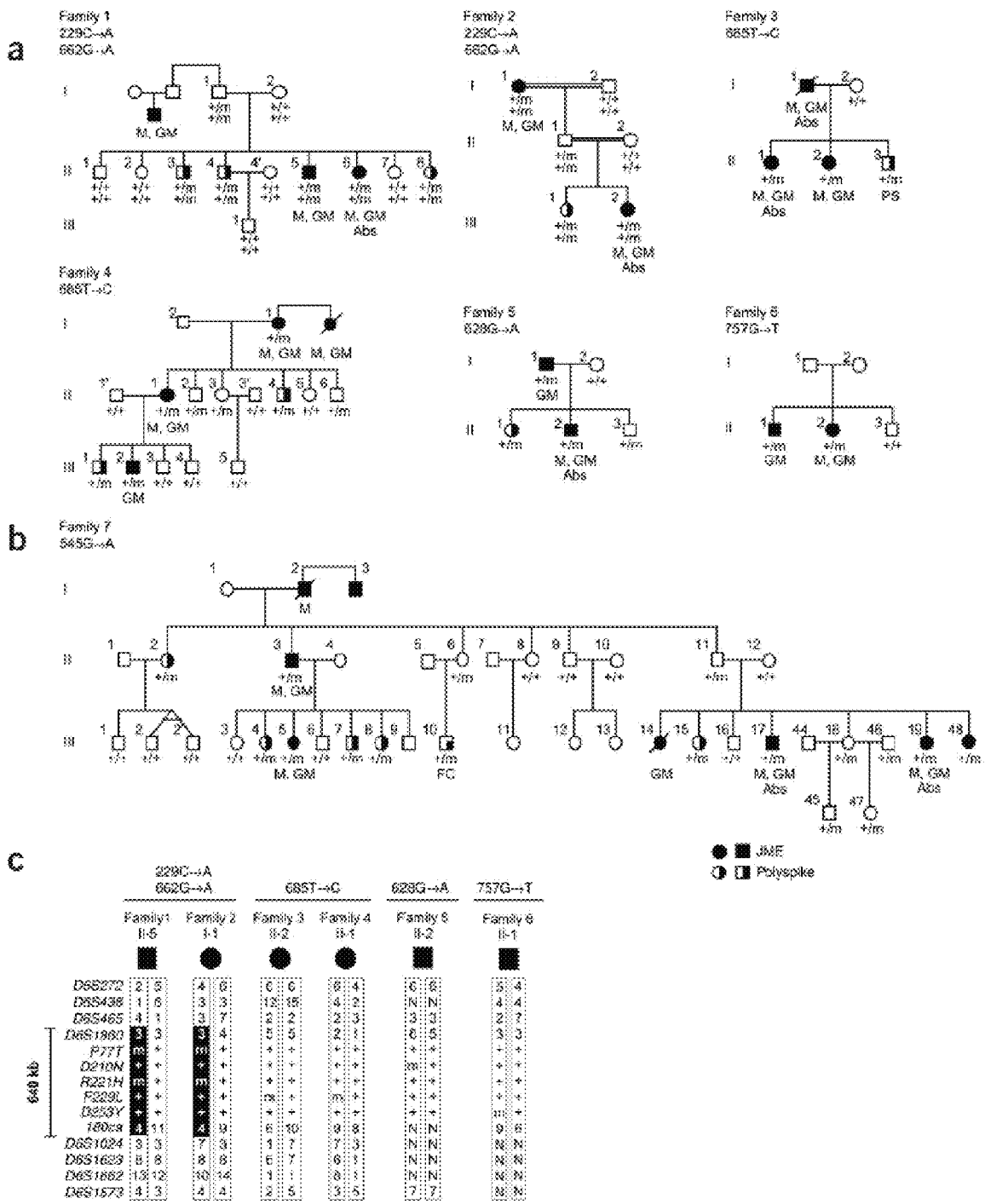
FIG. 2 shows EFHC1 mutations segregating with epilepsy traits in JME families.

Mutation analyses of EFHC1 was performed in 44 JME families (31 Mexican families, one from Belize, and 12 Caucasian families from Los Angeles) (FIG. 2a,b). The analyses revealed three heterozygous (F229L, D210N, D253Y) and one double heterozygous (P77T and R221H) mutations in all 21 affected members of six unrelated families (FIG. 2a). These mutations (named as JME mutations) were not observed in 382 unrelated healthy controls implying that they are not neutral polymorphisms. Haplotype analysis suggested a founder effect for a 640 kb region surrounding the doubly heterozygous mutations (FIG. 2c). Four of these mutations affected residues conserved among EFHC1 orthologs. Three coding (R159W, R182H, and I619L) and several non-coding polymorphisms were detected in both affected and control population. The frequencies of these coding polymorphisms in probands of the 31 Mexican JME families were 16% (5/31), 19% (6/31), 10% (3/31), respectively, and in the general population they were 14% (29/209), 11% (23/213), and 5% (10/208), respectively. The frequencies were high in patients but statistically not significant (p=0.78, 0.22, 0.38, respectively). A large three-generation family from Belize showed the variant R182H co-segregating with 11 affected members (FIG. 2b). The variant I619L segregated with affecteds of three other families. The families were regrouped into those with and without EFHC1 mutations, and LOD scores were recalculated separately. No significant differences were found between scores of the two groups. Bai, et al., *Am. J. Med. Genet.*, 133: 268-274, 2002; Liu, et al., *Am. J. Hum. Genet.*, 57: 368-381, 1995; Liu, et al., *Am. J. Med. Genet.*, 63: 438-446, 1996.

FIG. 2a shows one doubly heterozygous (P77T & R221H) and three heterozygous missense mutations (F229L, D210N, D253Y) co-segregated with 13 epilepsy and 8 EEG polyspike wave-affected members of six Mexican JME families. Of 13 epilepsy-affected persons, 10 had JME, while 3 had grand mal only. Of 10 with JME, 3 also had rare absences and one had rare absences in clusters. Pyknoleptic absence appearing as the only phenotype was not observed in any affected member. Several family members with mutations (I-1 in family #1; II-1 in family #2; II-2, II-3, II-6 in family #4; and II-3 in family #5) did not show clinical epilepsy or EEG polyspike waves indicating 78% (21/27) penetrance. +: wild-type allele, m: mutant allele, blackened symbol: JME affected (M: myoclonic, GM: grand-mal tonic-clonic, Abs: absence seizures, PS: photosensitivity of EEG polyspike wave complexes), half-blackened symbol: clinically asymptomatic family members with EEG 3.5-6 Hz multispike and slow wave complexes. (b) The R182H amino acid change segregates with affected family members of a large JME Family from Belize (family 7) with 65% (11/17) penetrance. One quarter blackened symbol indicates febrile convulsion (FC). (c) Haplotypes of JME families surrounding the EFHC1 locus. Haplotype analysis revealed identical 640 kb series of alleles surrounding the doubly heterozygous mutations in apparently unrelated families #1 and #2, suggesting a founder effect. No common alleles surrounding the mutations were found in families #3, #4, #5 and #6 suggesting that the identical mutations found in families #3 and #4 were generated by recurrent mutational events. m: mutant allele, +: wild-type allele, N: not done. Liu, et al., Am. J. Hum. Genet., 57: 368-381, 1995; Liu, et al., Am. J. Med. Genet., 63: 438-446, 1996.

Example 3

Activation of R-Type VDCC ($Ca_v2.3$)

To investigate the functional significance of EFHC1 and its mutants in neurons, mouse hippocampal primary culture neurons were transfected with EGFP-EFHC1 expression constructs (FIG. 3a-i). Sixteen hours post-transfection, EFHC1-positive neurons showed shorter neurites and lesser branches (FIG. 3b). Forty-eight hours post-transfection, all EFHC1-positive neurons exhibited signs of neurodegeneration and cell death including the shrinkage of cell body and fragmentation of processes (FIG. 3d), while control cultures appeared to be healthy (FIG. 3c). EFHC1-transfected cells were TUNEL positive indicating apoptosis (FIG. 3e-g). Next, the effects of EFHC1 mutations on cell survivability were investigated by counting GFP-positive surviving cells attached to the dishes at various time points, irrespective of cellular morphologies. The results revealed that cell-death effect of EFHC1 was significantly reduced by any of the five JME mutations or the double mutation P77T/R221H. In contrast, the three coding polymorphisms identified also in control population did not affect the cell death-effect significantly (FIG. 3h). Although the number of surviving cells for the JME mutants seemed close to that of vector-transfected cells, JME mutant-transfected cells showed unhealthy morphology at 48 hours post-transfection implying that JME mutations did not disrupt the EFHC1 function completely. The effects of EFHC1 isoform on cell survival were analyzed. Transcript B expression construct (named as Iso) produced moderate cell-death effects, and WT (wild-type)/Iso co-expression showed intermediate effects (FIG. 3i). The cellular functions of isoform protein encoded by Transcript B are presently unknown, but the fact that this isoform excludes the mutation D253Y from its ORF suggests that this isoform may not play a major role in the pathogenesis of JME.

Figure 15:
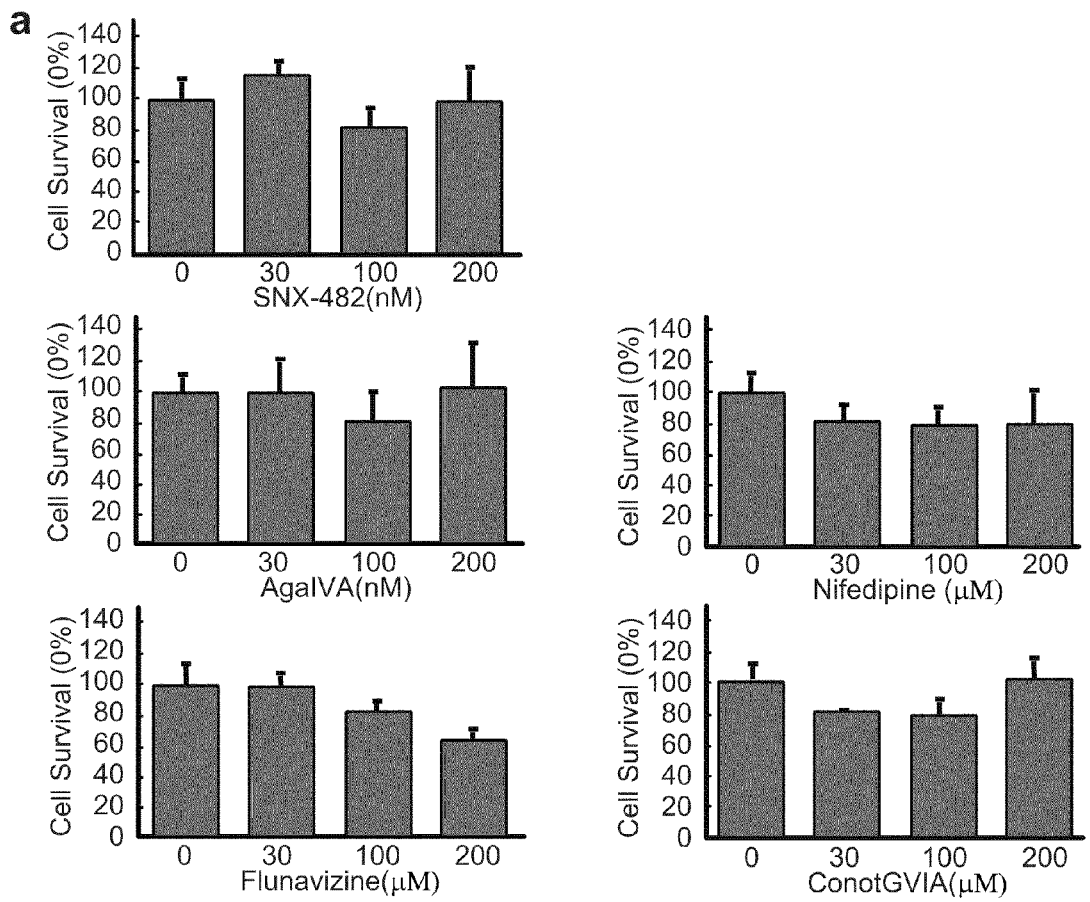
FIG. 15 shows effects of VDCC antagonists on hippocampal primary culture neurons transfected with EGFP vector control.

Since EFHC1 contains a Ca2+ sensing EF-hand motif and because abnormalities of voltage-dependent Ca2+ channels (VDCCs) have been described in human and mouse epilepsies, it was investigated whether observed cell death is due to modulations of any VDCCs. RT-PCR showed that most of the VDCC subtypes are expressed in mouse primary culture neuron albeit at varied levels (FIG. 3j). Treatments of EFHC1-transfected primary culture neurons with several antagonists of VDCC subtypes revealed that SNX-482, antagonist for Cav2.3 (ref. 17), specifically increased the survival rates of EFHC1-positive neurons (FIG. 3k and FIG. 15). Escayg, et al., Am. J. Hum. Genet., 66: 1531-1539, 2000; Jouvenceau, et al., Lancet, 358: 801-807, 2001; Fletcher, et al., Cell, 87: 607-617, 1996; Burgess, et al., Cell, 88: 385-392, 1997; Letts, et al., Nat. Genet., 19: 340-347, 1998.

Figure 3:
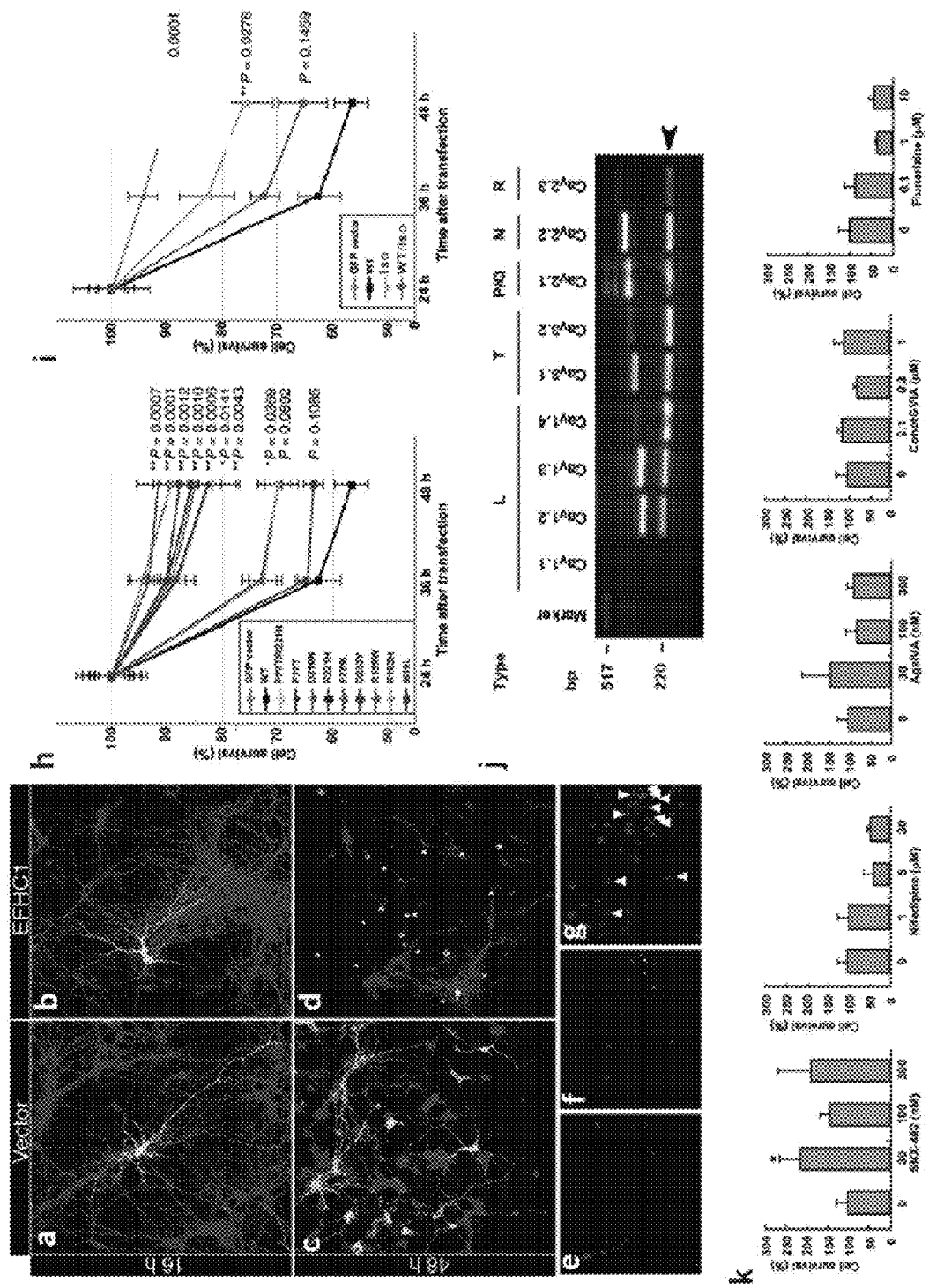
FIG. 3 shows activation of R-type VDCC ($Ca_v2.3$)-dependent apoptosis by EFHC1 and its reversal by JME mutations.

FIG. 3 shows hippocampal primary culture neurons were transiently transfected with expression constructs pEGFPC2-EFHC1 encoding GEF-EFHC1 (GFP attached at the N-terminus of EFHC1) fusion protein (b, d) or pEGFPC2 control vector encoding GFP only (a, c). The hippocampal neurons were stained with anti-MAP2 antibody (a-d). Sixteen hours after transfection, EFHC1-transfected cells showed shorter neurites and fewer branches (b). Forty-eight hours after transfection, EFHC1-transfected cells exhibited neurodegenerative morphologies including shrinkage of the cell body and fragmentation of processes (d). (e-g) TUNEL assay of EFHC1-transfected hippocampal primary culture. Neuronal cells were transiently transfected with expression constructs pcDNA3-Myc-EFHC1. (e) Staining with anti-myc antibody. (f) TUNEL positive cells. (g) Overlap of images e, f, and Hoechst staining of nuclear chromatin. Most of the EFHC1-transfected cells overlap with TUNEL positive cells (arrows). (h, i) Graphs of the GFP fluorescent-positive surviving cell numbers at 24, 36, and 48 hours after transfection of the EFHC1-expression constructs. The surviving cell numbers are expressed as percentage; 100% at 24 hours after transfection. Each data point represents the average±S.E.M. from seven culture wells (t-test as compared to wild-type EFHC1). (h) JME mutations (P77T/R221H, P77T, D210N, R221H, F229L, D253Y) appeared only in patients significantly reversed the cell death-effect of EFHC1 at 36 and 48 hours after transfection, while the constructs with polymorphisms appearing in both patients and controls (R159W, R182H, I619L) largely maintained the cell-death effects. (i) GFP-fusion constructs of transcript A (WT) and/or transcript B (iso) or GFP vector were transfected into neuron cells. Single transfection of iso showed a moderate cell-death effect, while WT and iso co-transfection (half amount of DNA for each) showed an intermediate effect. (j) Expression levels of calcium channel α-subunits in mouse primary hippocampal neurons investigated by RT-PCR. Neuron specific enolase was co-amplified as a control (Arrow head). (k) Effects of VDCCs' antagonists on EFHC1-transfected hippocampal primary culture neurons. The surviving cell numbers at 48 hours after transfections are expressed as percentage; 100% at no antagonists. t-test statistics was applied for significance. Values are mean±S.E.M. (n=4; control, n=8). *p<0.05 versus control (no antagonist). The results of control experiments with EGFP vectors are shown in FIG. 15. FIG. 15a shows effects of VDCC antagonists on hippocampal primary culture neurons transfected with EGFP vector control. Surviving GFP-positive neurons were counted and test statistics was applied for significance. Values are mean+/−S.E.M. (n=4; control, n=6). FIG. 15b shows immunoprecipitation assays of EFHC1 mutant proteins and $Ca_v2.3$ C-terminus fragment protein. Flag-tagged C terminus of $Ca_v2.3$ or Flag-tagged endophilin, and Myc-tagged EFHC1 wild type (WT) or EFHC1 mutants were coexpressed in HEK cells, and cell lysates were immunoprecipitated by anti-Flag antibody. Electrophoresed cell lysates or immunoprecipitants were blotted on membranes, and probed with anti-Flag or anti-Myc antibodies. WT and all mutants of EFHC1 were co-immunoprecipitated with $Ca_v2.3$ C-terminus Flag-tagged endophilin did not co-precipitate with Myc-tagged EFHC1-WT. Ab: antibody, IP: immunoprecipitateion, IB: immunobloting.

Example 4

Co-Localization of EFHC1 and $Ca_v2.3$ Proteins

Immunohistochemical analyses (FIG. 4a-k) revealed that Efhc1 protein is widely expressed in adult mouse brain including hippocampus (FIG. 4a,c), cerebellum (FIG. 4o, cerebral cortex (FIG. 4i), thalamus, hypothalamus, amygdala and upper brainstem and largely overlapped with signals for $Ca_v2.3$ FIG. 4b, d, g, j; merged images e, h, k). Yokoyama, et al., J. Neurosci. 15: 6419-6432, 1995. Double-staining of hippocampal primary culture neurons with anti-EFHC1 antibody and anti-$Ca_v2.3$ antibody showed signals at soma and dendrites (FIG. 4l-n).

Figure 4:
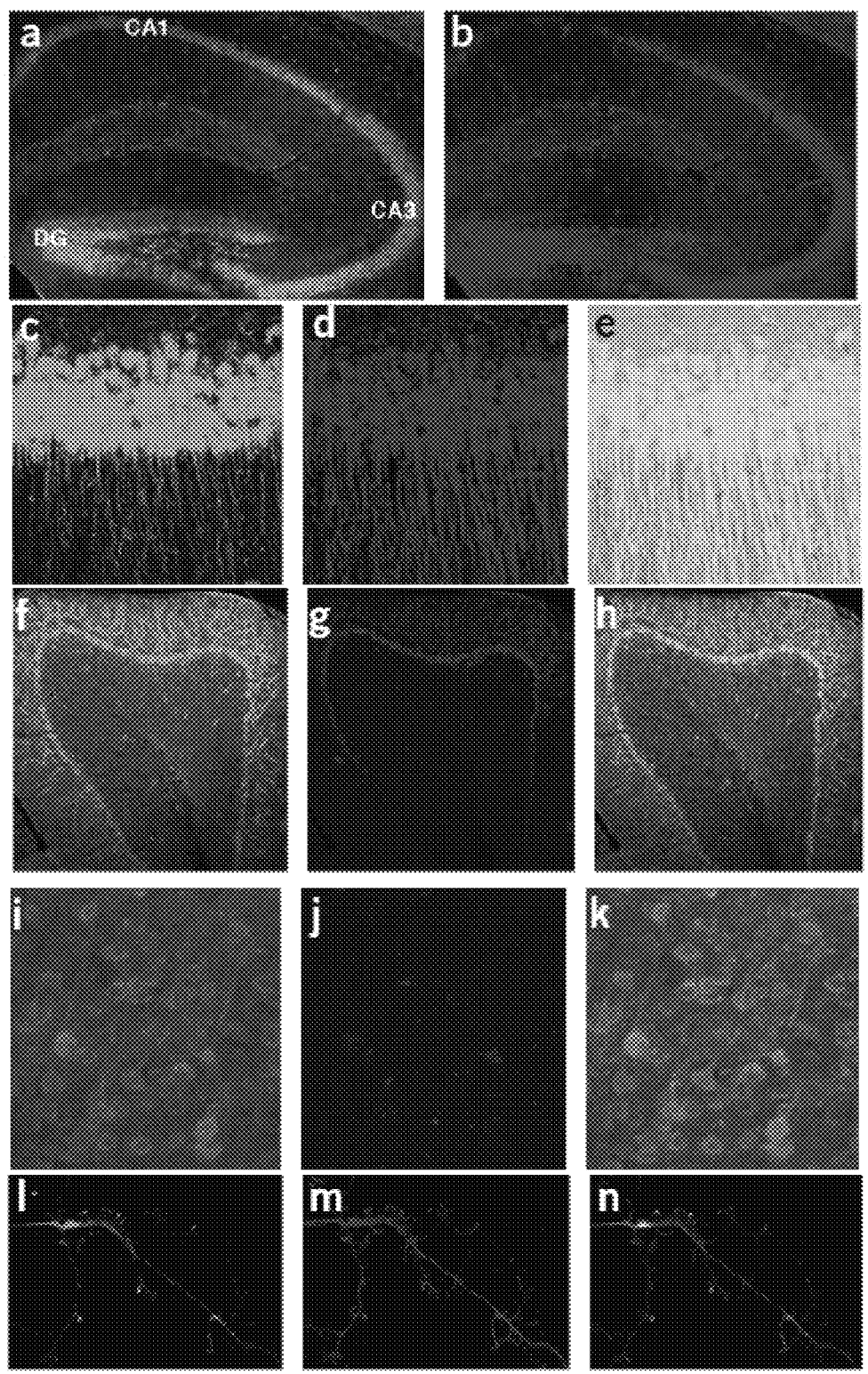
FIG. 4 shows co-localization of Efhc1 and $Ca_v2.3$ proteins.

FIG. 4 shows: (a-k) Mouse adult brain sections were double-stained with anti-EFHC1 antiserum visualized with Alexa-488 (a, c, f, i) and with anti-$Ca_v2.3$ antibody visualized with Alexa-594 (b, d, g, j). (e, h, k) Merged images. (a, b) Hippocampus. (c-e) Hippocampus CA1 region. (f-h) Cerebellum. (i-k) Cerebral cortex. (l-n) Hippocampal primary culture neurons (6 days in vitro) from E16 mouse were double-stained with anti-Efhc1 (green; 1) and anti-$Ca_v2.3$ antibody (red; m). Signals were merged in FIG. 4n.

Example 5

Potentiation of Voltage-Dependent R-Type $Ca^{2+}$ Channel ($Ca_v2.3$) Activity by EFHC1 and Mutants of EFHC1

Patch-clamp analyses of baby hamster kidney (BHK) cells stably expressing $Ca_v2.3$ and transiently transfected with EFHC1 expression constructs revealed that EFHC1 significantly increased the R-type $Ca^{2+}$ current generated by $Ca_v2.3$ (FIG. 5a-c). Cells co-transfected with P/Q-type VDCC ($Ca_v2.1$) and EFHC1 expression constructs did not show such increase of calcium currents. EFHC1's effects on $Ca_v2.3$ were extensive and unique, even when compared to effects of $Ca^{2+}$ channels' auxiliary subunits. These results suggest that EFHC1 enhances $Ca^{2+}$ influx through $Ca_v2.3$ and stimulates programmed cell death. JME mutations partly reversed the increase of R-type $Ca^{2+}$ currents by EFHC1 (FIG. 5b,c). Incomplete reversal of EFHC1-induced calcium influx through $Ca_v2.3$ may be responsible for the precarious state of calcium homoeostasis sensitive to the triggering effects of sleep deprivation, fatigue, and alcohol in JME patients. The three coding polymorphisms showed weaker or no reversal effects (FIG. 5b,c) implying that these polymorphisms could be functionally benign or less malignant. The Transcript B isoform (iso) showed a moderate level of current increase (FIG. 5b,c). These results are consistent with those of cell death analyses (FIG. 3h,i). Letts, et al., *Nat. Genet.*, 19: 340-347, 1998; Wakamori, et al., *J. Biol. Chem.*, 273: 34857-34867, 1998.

Figure 5:
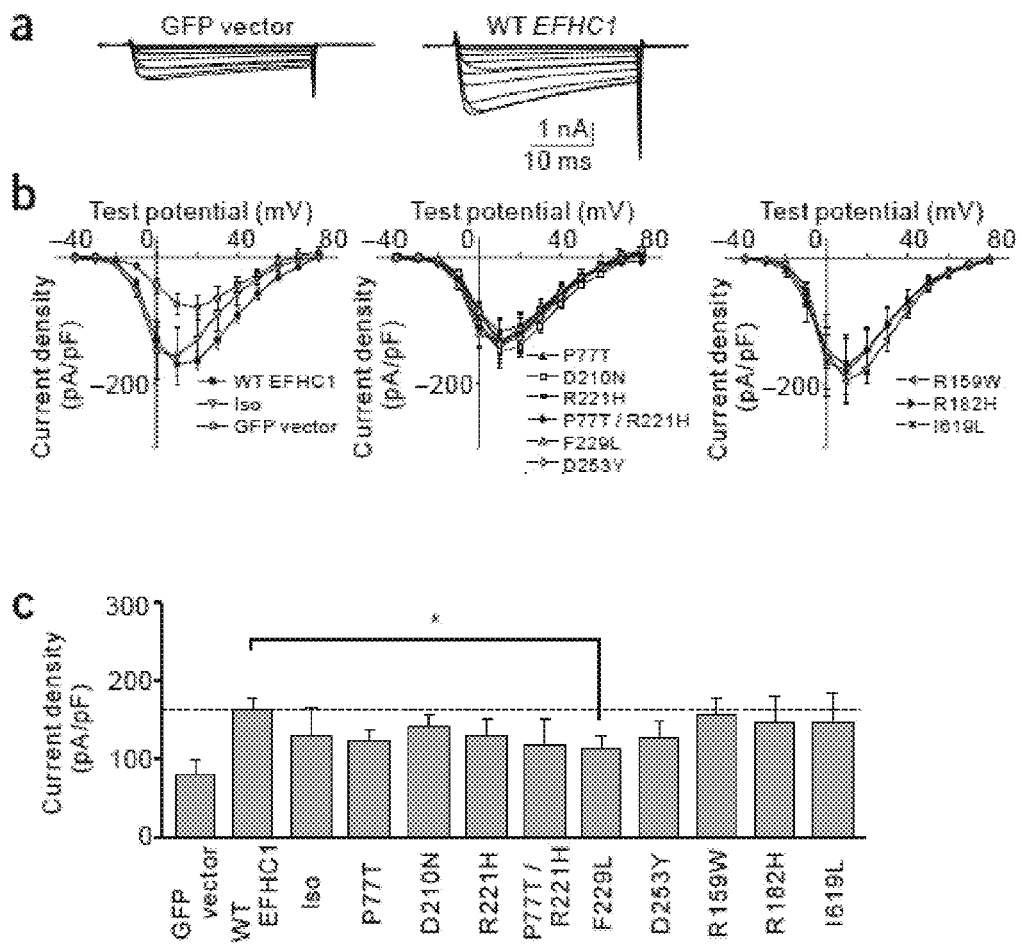
FIG. 5 shows potentiation of voltage-dependent R-type $Ca^{2+}$ channel ($Ca_v2.3$) activity by EFHC1 and its mutants.

FIG. 5 shows: (a) $Ca^{2+}$ currents of recombinant $Ca_v2.3$ evoked in BHK cells transiently transfected with control GFP vector or wild-type (WT) EFHC1 cDNA. Test depolarizing pulses were from −40 to 80 mV for 30 ms. Holding potential was −110 mV. (b) Current-voltage relationships of recombinant $Ca_v2.3$ in BHK cells transfected with GFP vector (open circles), WT EFHC1 (closed circles), transcript B (iso) (open downward arrowheads), and EFHC1 mutants P77T (closed triangles), D210N (open squares), R221H (closed squares), P77T/R221H (closed diamonds), F229L (open triangles), D253Y (open diamonds), R159W (open left arrowheads), R182H (closed right arrowheads), I169L (stars). WT EFHC1 and mutants significantly up-regulates R-type ($Ca_v2.3$) $Ca^{2+}$ currents. (c) $Ca^{2+}$ current densities evoked at 20 mV in BHK cells co-expressing $Ca_v2.3$ in combination with EFHC1 constructs. The JME mutations partly reversed the R-type current increasing effect of EFHC1. The mutation F229L significantly suppressed the potentiation effect of EFHC1 (*$p<0.05$). The modulation of activation and inactivation properties of $Ca_v2.3$ by EFHC1 mutants is described in the FIG. 24.

Example 6

Immunoprecipitation Assays of EFHC1 and Voltage-Dependent $Ca^{2+}$ Channels (VDCCs)

Voltage-dependent $Ca^{2+}$ channels (VDCCs) are often regulated by proteins that interact with intracellular C-termini of VDCCs. The co-immunoprecipitation assays were performed with C-terminal fragments of P/Q-type ($Ca_v2.1$), N-type ($Ca_v2.2$) and R-type ($Ca_v2.3$) VDCC, and found that Myc-tagged EFHC1 co-precipitated with the Flag-tagged C-terminus of $Ca_v2.3$ but not with $Ca_v2.1$ or $Ca_v2.2$ (FIG. 6a,b). Reciprocal co-immunoprecipitation of Flag-tagged EFHC1 and Myc-tagged $Ca_v2.3$ C-terminus also yielded positive results (FIG. 6c,d). Deletion analyses of EFHC1 revealed that $Ca_v2.3$ bound to EFHC1 N-terminus (a.a. 1-359), that was composed of DM10(1) and DM10(2) and harbored all of the JME mutations (FIG. 6c,d). All EFHC1 mutant proteins showed binding abilities to the $Ca_v2.3$ C-terminus See FIG. 15. Catterall, et al., *Annu. Rev. Cell Dev. Biol.*, 16: 521-555, 2000.

Figure 6:
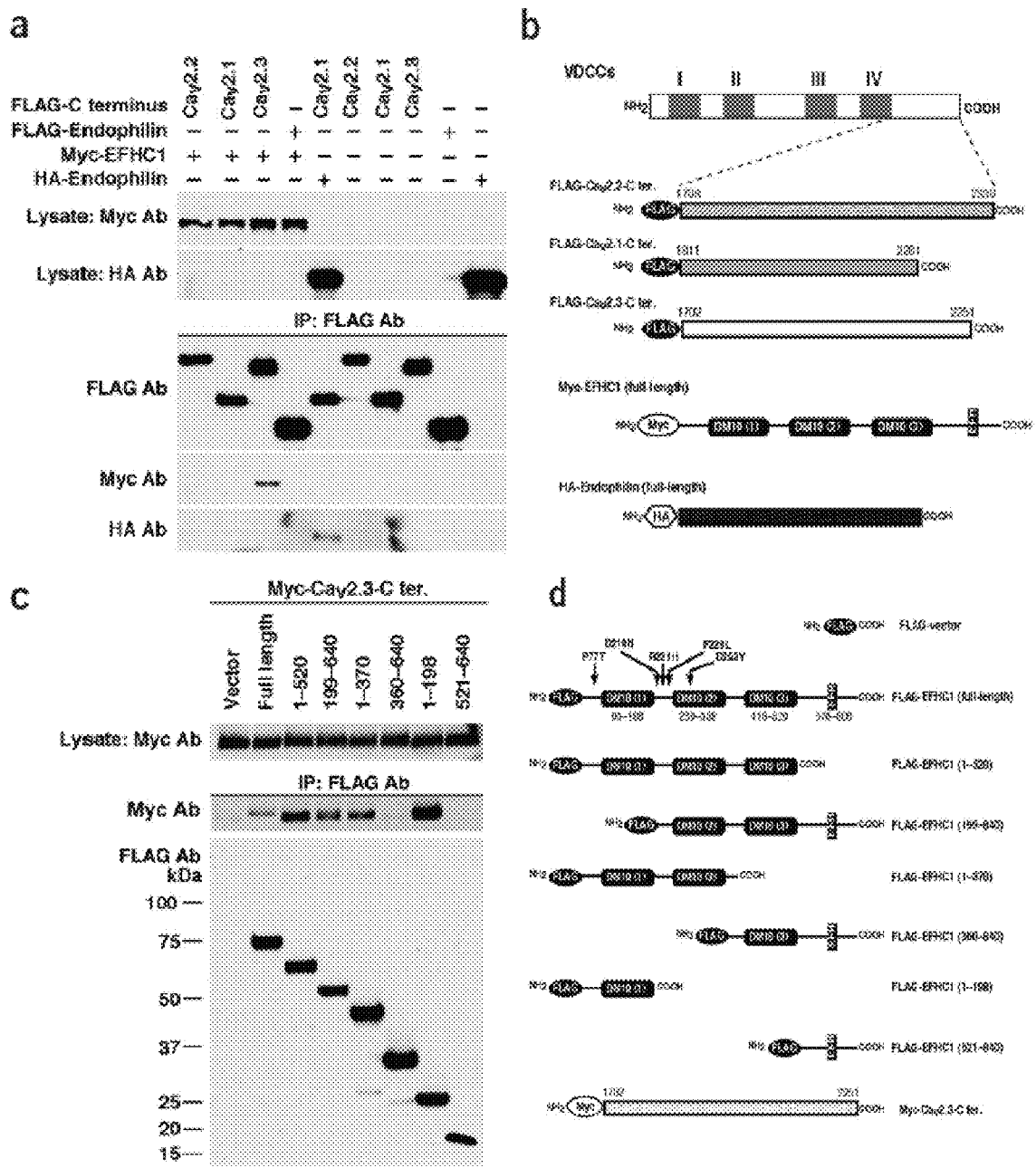
FIG. 6 shows immunoprecipitation assays of EFHC1 and voltage-dependent $Ca^{2+}$ channels (VDCCs).

FIG. 6 shows: (a) Flag-tagged C-termini of VDCCs, or Flag-tagged Endophilin, and Myc-tagged EFHC1 or HA-tagged Endophilin were co-expressed in HEK cells, and cell lysates were immunoprecipitated by anti-Flag antibody. Electrophoresed cell lysates or immunoprecipitants were blotted on membranes, and probed with anti-Flag, anti-Myc, or anti-HA antibodies. C-terminus of $Ca_v2.3$ were co-immunoprecipitated with EFHC1, while those of $Ca_v2.1$ and $Ca_v2.2$ did not. HA-tagged endophilin bound to $Ca_v2.1$ C-termini as reported previously[29], but Flag-tagged endophilin did not co-precipitate with Myc-tagged EFHC1. Approximate molecular weights for EFHC1, $Ca_v2.1$, $Ca_v2.2$ and $Ca_v2.3$ C-termini are 74 kDa, 52 kDa, 69 kDa and 62 kDa respectively. (b,d) Structures of tagged proteins used for immunoprecipitation assays. The C-termini of $Ca_v2.1$, $Ca_v2.2$, $Ca_v2.3$ were PCR-amplified and Flag- or Myc-tagged at their N-termini. Full-length and truncated EFHC1 were PCR-amplified and Myc or Flag-tagged at N-termini. (c) The assay of EFHC1 truncated proteins and C-terminus of $Ca_v2.3$. The result suggests that $Ca_v2.3$ binds to N-terminus (a.a. 1-359) of EFHC1. Ab: antibody, IP: immunoprecipitation.

Example 7

Mutations in EFHC1 Can Cause JME

Several possibilities exist to explain how mutations in EFHC1 can cause JME. One possibility is that JME mutations, by compromising apoptotic activity of EFHC1 through $Ca_v2.3$, prevent elimination of unwanted neurons during CNS development, lead to increased density of neurons with precarious calcium homeostases, and produce hyper-excitable circuits. In fact, increased densities and dystopia of neurons have been observed in brains of JME patients. Although no seizure phenotype has been described in the mice lacking $Ca_v2.3$ (ref. 23), undetected minor seizure sensitivities or brain microdysgeneses may still exist in this mouse. Species differences may also be a factor. Furthermore, EFHC1 protein does not bind to $Ca_v2.3$ only, but also interacts with additional number of proteins that may be modifying the JME phenotype. Woermann, et al., *Brain*, 121: 1661-1667, 1998; Meencke, et al., *Jasper's Basic Mechanisms of the Epilepsies, 3rd Edition, Advances in Neurology*, 79: 123-131, 1999.

In this study, mutations of EFHC1 were identified in only six of 44 JME families Unidentified mutations may exist in intronic or regulatory regions of EFHC1 as was observed in Unverricht-Lundborg progressive myoclonus epilepsy. An extensive search was made for mutations in ~100 bp of each exon-intron boundary and ~650 bp 5'-UTR of EFHC1 for all the JME families. Several patients revealed SNPs, but none showed significant association with the disease phenotype. The SNPs in the 5' UTR also did not affect the EFHC1 promoter activity. Further searches of mutations in expanded regions are warranted. Another possibility is that other genes in or outside the chromosome 6p region might be responsible for JME in some of the remaining 38 families. Common haplotypes at 6p12 in affected members of small JME families could have occurred by chance and might not necessarily be associated with EFHC1 mutation in all cases. Pennacchio, et al., *Science*, 271: 1731-1734, 1996; Virtaneva, et al., *Nat. Genet.*, 15: 393-396, 1997.

In summary, segregation of EFHC1 mutations in epilepsy or polyspike wave-affected persons of JME families, together with reversal of the EFHC1-induced neuronal cell death and EFHC1-dependent increase of R-type $Ca^{2+}$ current by JME mutations, strongly support EFHC1 as the JME gene on 6p12. Most genes incriminated as the cause of idiopathic generalized epilepsy encode ion channels. Identification of a gene encoding a non-ion channel protein containing an EF-hand motif, modulating and interacting with R-type VDCC, and showing apoptotic activity, brings a new viewpoint to the molecular pathology of idiopathic epilepsy.

Example 8

Methodology

Families and Patients. In this study, 44 JME families (31 Mexican families, one from Belize, and 12 Caucasian families from Los Angeles) were analyzed. Each participating subject or responsible adult signed an informed consent form as approved by the Human Subject Protection Committee at the UCLA School of Medicine or the participating institutions. Criteria for inclusion of probands consist of the followings: 1) Myoclonic seizures started between 10 to 20 years of age, usually on awakening involving shoulders, arms, and other parts of the limbs. Myoclonic seizures were not associated with loss of consciousness. 2) Tonic-clonic or clonic tonic-clonic convulsions usually appeared 1 to 2 years and rarely 5 to 10 years after the start of myoclonic seizures. 3) Neurological examination including mental status and intelligence must be normal, and 4) Diffuse synchronous and symmetrical 3.5-6 Hz polyspike-wave complexes were present in the interictal EEG of all probands. Individuals with abnormal spike/polyspike wave complexes in the EEG were assigned as affected even if they were free of seizures. The 382 unrelated healthy controls consist of 252 Mexicans, 96 Japanese, and 34 Caucasians from Los Angeles. Genomic DNA was extracted from peripheral venous blood by using QIAamp DNA Blood Mini Kit (Qiagen). Bai, et al., *Am. J. Med. Genet.,* 133: 268-274, 2002; Liu, et al., *Am. J. Hum. Genet.,* 57: 368-381, 1995; Liu, et al., *Am. J. Med. Genet.,* 63: 438-446, 1996.

Construction of physical and transcriptional map. Construction of physical map was performed as described previously. BAC and PAC sequences were used to search for genes registered in the NCBI BLAST database (http://www.ncbi.nlm.nih.gov/BLAST/). Sugimoto, et al., *Genomics,* 68: 264-272, 2000.

Domain search. A domain search in the EFHC1 amino acid sequence was performed through the InterPro, Pfam and SMART databases (http://www.ebi.ac.uk/interpro/scan.html, http://pfam.wustl.edu/hmmsearch.shtml, http://smart.embl-heidelberg.de/).

Northern blot analysis. Blots were purchased or prepared as follows. Total RNAs were extracted from adult and embrynic 17 days ICR mouse whole brain by using TRIZOL™ Reagent (Invitrogen) and poly $A^+$ RNAs were obtained using µMAX mRNA Isolation Kit (Miltenyi Biotec GmbH). 4 µg of poly $A^+$ RNA per lane was run on a denaturing formaldehyde 1.0% agarose gel, blotted to a nylon membrane, and fixed by UV irradiation. EFHC1 or Efhc1 cDNAs were amplified by PCR using human or mouse adult brain cDNA as a template. The PCR products were $^{32}$P-radiolabeled by High Prime DNA Labeling Kit (Roche) and purified using MicroSpin G-50 columns (Amersham Biosciences). The labeled DNAs were used as probes for northern hybridization using Multiple Human (or Mouse) Adult Tissue Northern Blots, Multiple Human Adult Brain Tissue Northern Blots, Mouse Embryo Tissue Northern Blots (Clontech) or Mouse Brain of Embryo 17-days and Adult Northern Blot. These blots were hybridized overnight with ExpressHyb hybridization solution (Clontech) and washed finally in 0.1×SSC/0.1% SDS at 50° C. for 40 min The filters were exposed to X-ray film at −80° C. for over night. As a control, the same blot was hybridized to G3PDH or β-actin probe. New blots were used for all hybridizations and not used repeatedly.

cDNA library screening. Human adult brain, pancreas, and fetal brain cDNA libraries constructed in the Lambda ZAP II vector (Stratagene) were screened by using a PCR product (probe 3; see FIG. 1b) as a probe according to manufacturer's recommendation.

Generation of anti-EFHC1 antibody. A synthetic peptide corresponding to amino acid residues 522-533 (QYSPEALASIQN (SEQ ID NO: 20)) of human EFHC1, the sequence is identical to that of mouse Ethel, was used for immunization. The peptide with one cysteine residue added at the N-terminus was coupled keyhold limpet hemocyanin, mixed with Freund's complete adjuvant in phosphate-buffered saline (PBS), and injected into two rabbits at a dose of 1 mg protein/injection. Rabbits were boosted with peptide sequence mixed with incomplete adjuvant in PBS at 3 and 6 weeks after the first injection and bled at 8 weeks.

Mouse hippocampal neurons primary culture. Hippocampal neurons were isolated from embryonic day 16 mice and plated at $1-2\times10^5$ cells per well in 24 well plate containing glass coverslips coated with poly-1-lysine and grown in serum-free NEUROBASAL™ media supplemented with B27, 0.5 mM L-glutamine (Invitrogen).

Immunocytochemistry. Hippocampal primary cultured neurons (6 days in vitro) from E16 mouse were fixed with 4% paraformaldehyde in PBS for 15 min and permeabilized with 0.1% Triton X-100 in PBS for 5 min. The cells were incubated with blocking solution (3% normal goat serum in PBS) for 30 min, and then incubated with primary antibody in blocking solution (anti-EFHC1 antibody at 1:1000 dilution and anti-MAP-2 antibody at 1:500; Sigma, or for anti-phosphorylared neurofilament antibody SMI310 at 1:200 dilution; Sternberger Monoclonals Incorporaed) for 1 hr at room temperature. After thorough washing with PBS, the cells reacted with secondary antibody (chicken anti-rabbit IgG Alexa 488 conjugated and donkey anti-mouse IgG Alexa 594 conjugated; Molecular Probes) diluted at 1:1000 for 1 hr at room temperature, washed three times in PBS and the fluorescence was observed with TCS SP2 microscope (Leica).

Colorimetric immunohistochemistry. 40 µm sections were cut using a cryostat (Leica 1900) and washed in 0.1M PBS, and immersed in 10% normal goat serum in PBS with 0.3% Triton (PBST) for 10 minutes. Even number sections were incubated overnight in a solution of primary antibody (1:2000 dilution for anti-EFHC1 C1, 1:2000 dilution for pre-immune serum, or 1:2000 dilution for anti-EFHC1 C1 with 50 µg/ml EFHC1 peptide QYSPEALASIQN (SEQ ID NO: 20)) diluted in 10% normal goat serum in PBST at 4° C. Following serial wash in PBST, sections were incubated for 3 hours at 40° C. with the secondary antibody, biotinylated goat anti-rabbit IgG. The sections were then reacted with ABC reagent (VECTASTAIN ABC KIT, Vector Lab. Inc.) for 1 hour at room temperature. Sections were washed in Tris-buffer (pH 7.2), and reacted with 0.02% DAB (Doujindo) with 0.01% $H_2O_2$ for 20 minutes at room temperature. After wash with Tris-buffer and PBS, sections were mounted on glass, dehydrated, cleared in xylene and cover-slipped.

RT-PCR. Total RNA was extracted from whole brain and hippocampal primary culture neuronal cells of adult ICR mouse using TRIZOL™ Reagent (Invitrogen) and obtained first-strand cDNA from 2 µg total RNA using Thermoscript™ RNA H⁻ Reverse Transcriptase (Invitrogen). To amplify mouse cDNAs, primers were designed in exon 1 and exon 11 (bp 13-2037) for Efhc1 and those for respective $Ca^{2+}$ channels, CACNA1S ($Ca_v1.1$), CACNA1C ($Ca_v1.2$), CACNA1D ($Ca_v1.3$), CACNA1F ($Ca_v1.4$), CACNA1G ($Ca_v3.1$), CACNA1H ($Ca_v3.2$), CACNA1A ($Ca_v2.1$), CACNA1B ($Ca_v2.2$) and CACNA1E ($Ca_v2.3$). Neuron specific enolase cDNA primers were used as controls. Primer sequences are available upon request.

Mutation analysis. Mutation screening was performed as described previously. Briefly, PCR primers were designed to amplify all 11 exons of EFHC1, and genomic DNA was amplified by PCR using the Pwo DNA Polymerase (Roche) and analyzed by hetero-duplex analysis using WAVE (Transgenomic) and direct-sequencing using ABI auto-sequencer type 3700 (PE Applied Biosystems). Primer sequences are available upon request. Morita, et al., *Epilepsy Res.*, 37: 151-158, 1999.

Expression constructs and mutagenesis. The complete open reading frame of EFHC1 (Transcript A) was amplified from human adult brain cDNA (Clontech) by PCR using Pyrobest™ (TaKaRa), and was cloned into pEGFPC2 (Clontech), pcDNA3-MycN (Invitrogen) or pcDNA3-FlagN (Invitrogen) vectors. Transcript B sequence was also amplified from human adult brain cDNA by PCR and was cloned into pEGFPC2. The GFP, Myc or Flag-tag sequences were fused at the N-terminus of EFHC1 protein. Five JME mutations were introduced by using Quick Change site-directed mutagenesis kit (Stratagene), and the nucleotide changes as well as the integrity of full sequences were confined by DNA sequencing.

Transfection and immunostaining of mouse hippocampal neurons. On day 4, expression DNA constructs encoding wild type and mutant EFHC1 proteins were transfected into the neuron cells using LIPOFECTAMINE™2000 (Invitrogen). Cultures were fixed with 4% paraformaldehyde in PBS 16 and 48 hours after transfection, permeabilized with 0.3% Triton X-100, blocked in 3% normal goat serum in PBS, and treated with mouse monoclonal anti-MAP-2 antibody (1:500; Sigma) and Alexa fluor 594 goat anti-mouse IgG antibody (1:1000; Molecular Probes).

TUNEL assay. Neurons were transfected with expression DNA construct (pcDNA-MycN-EFHC1-WT) on day 4 using LIPOFECTAMINE™2000. Forty-eight hours after transfection, neuronal apoptosis was detected using DeadEnd™ Fluorometric TUNEL System (Promega). Nuclei were visualized with Hoescht 33342 (Molecular Probes). These cells were also stained with anti-Myc antibody (1:200; Cell Signaling) and Alexa fluor 594 goat anti-rabbit IgG antibody (1:1000). All experiments were carried out in duplicate wells and at least repeated three times. Neuron cells were observed on a confocal microscope (OLYMPUS FLUOVIEW) following 48 hours post transfection.

Cell death analyses with EFHC1 mutants. Hippocampal primary culture neurons were transfected with GFP-EFHC1 fusion protein expression constructs, those with JME mutations, that of EFHC1 isoform, or GFP vector on day 4 using LIPOFECTAMINE™2000. Surviving cell numbers were scored by counting GFP fluorescent-positive cells that attached to dishes. At each counting, detached cells (dead cells) were carefully removed by changing culture medium. Morphologies of cells (cell shape, length and number of neurites, shrinkage, etc.) were not considered for the counting. Surviving cell numbers were scored at 24, 36, and 48 hours after transfection. Analyses were repeated twice by using two independently prepared expression construct DNAs. In total, neurons in seven wells of 24 well plates were counted for each transfection and time point. Experiments were performed in a blinded fashion.

Cell death analyses with VDCCs inhibitors. Dissociated hippocampal primary culture neurons from embryonic day 16 mice were seeded in 24 well plates containing poly-L-lysine coated coverslips ($5 \times 10^4$ cells/well). Neurons were transfected with pEGFP-EFHC1 on day 6 in vitro with antagonists and fixed 48 hours post transfection. Calcium channel inhibitors, ω-Agatoxin IVA (PEPTIDE INSTITUTE, INC.) for P-type ($Ca_v2.1$), ω-Conotoxin GVIA (PEPTIDE INSTITUTE, INC.) for N-type ($Ca_v2.2$), SNX-482 (PEPTIDE INSTITUTE, INC.) for R-type ($Ca_v2.3$), flunarizine (Nacalai Tesque) for T-type and nifedipine (SIGMA) for L-type VDCC, were added directly to neuronal culture 3 hrs post transfection.

Fluorescence immunohistochemistry. ICR adult mice were deeply anaesthetized and transcardially perfused with 4% paraformaldehyde (PFA) in phosphate-buffer (pH7.4). The brains were dissected out and post-fixed for an additional 3 hrs at 4° C., and cryoprotected 30% sucrose in buffer (pH7.4). Brain samples were transferred to moulds containing Tissue-Tek OCT medium, and freezed by $CO_2$ air. Floating frozen sections (20 µm) were prepared by cryostat. Sections were rinsed in PBS and blocked with 5% FBS in PBS with 0.3% triton X-100 for 1 hr at room temperature (RT), and then incubated for 72 hrs at 4° C. with the anti-EFHC1 rabbit polyclonal antibody diluted at 1:3000 and subsequently with goat polyclonal antibody anti-α1E ($Ca_v2.3$, C-20; Santa Cruz Biotechnology) diluted at 1:10. Sections were incubated with the secondary antibodies (chicken anti-rabbit IgG Alexa 488 conjugated and donkey anti-goat IgG Alexa 564 conjugated; Molecular Probes) diluted at 1:300 for 1 hr at RT. Images were acquired under TCS SP2 microscope (Leica).

Electrophysiological analysis. A baby hamster kidney (BHK) cell line BHK (BII-104-2) stably transfected with the $\alpha_{1E}$ (BII), $\alpha_2/\delta$ and $\beta_{1a}$ subunits, were cultured in DMEM medium containing 10% fetal bovine serum (FBS), 30 U/mL penicillin and 30 µg/mL streptomycin. To transiently express wild type or mutant EFHC1, BHK (BII-104-2) cells were transfected with the pEGFP-C2 plasmids (Clonetech) containing EGFP fused with cDNA for EFHC1 or its mutants using SuperFect Transfection Reagent (QIAGEN). For control experiments, EGFP was transiently expressed by transfecting BHK (BII-104-2) with the same amount of pEGFP without the EFHC1 inserts. Cells were trypsinized, diluted with the DMEM medium, and plated onto glass coverslips 18 hrs after transfection. $Ca^{2+}$ currents were recorded 24-48 hr after transfection from GFP-positive cells. Currents from BHK (BII-104-2) cells were recorded at room temperature (22-25° C.) using patch-clamp techniques of whole cell mode with an EPC-9 amplifier (HEKA, Germany). Patch pipettes were made from borosilicate glass capillaries (1.5 mm outer diameter and 0.87 mm inner diameter; Hilgenberg) by using a model P-97 Flaming-Brown micropipette puller (Sutter Instrument Co., CA). Pipette resistance ranged from 2 to 3 MΩ when filled with the pipette solutions described below. The series resistance was electronically compensated to >70% and both the leakage and the remaining capacitance were subtracted by −P/6 method. Currents were sampled at 100 kHz in activation kinetics, otherwise sampled at 50 kHz and filtered at 10 kHz. Calcium currents were recorded in an external solution that contained (in mM): 3 $CaCl_2$, 148 tetraethylammonium chloride (TEA-Cl), 10 glucose, and 10 HEPES, pH adjusted to 7.4 with Tris-OH. The pipette solution contained (in mM): 85 Cs-aspartate, 40 CsCl, 4 $MgCl_2$, 5

EGTA, 2 ATP2Na, 5 HEPES, and 8 creatine-phosphate, pH adjusted to 7.4 with CsOH. To determine voltage-dependence of activation, amplitude of tail currents at −50 mV after 5 ms test pulse (−40 to 90 mV) was normalized to the maximal tail current amplitude. To determine voltage-dependence of inactivation, amplitude of currents elicited by the 20 ms test pulse to 30 mV after 10 ms repolarization to −110 mV following 2s displacement of holding potentials (−110 mV to 20 mV) was normalized to the current amplitude elicited by the test pulse after the 2s holding potential displacement to −110 mV. All values are given as mean±SE. Statistical comparison was performed by Student's t-test (*, p<0.05; **, p<0.01). The experiments were performed in a blinded fashion. Niidome, et al., *FEBS Lett.*, 308: 7-13, 1992; Chen, et al., *Cell*, 115: 37-48, 2003.

Immunoprecipitation. HEK cells co-transfected with expression constructs were collected 20 hrs post transfection. The cells were washed in PBS, scraped and homogenized in the lysis buffer (10 mM Tris pH 8.0, 150 mM NaCl, 5 mM EDTA) supplemented with protease inhibitors (Complete; Roche). Cellular debris was removed by centrifugation at 12,000×g for 10 min at 4° C. The supernatants were precleared with protein G-Sepharose (Amersham Pharmacia Biotech) for 2 h at 4° C. and then incubated with monoclonal anti-Flag M2-Agarose beads (Sigma) or anti-Myc antibody (Santa Cruz) for 12 hrs at 4° C. Protein G-Sepharose was used for precipitation with anti-Myc antibody. The beads were washed with lysis buffer five times and then eluted either with Flag peptide or SDS sample buffer for immunoblot analyses.

Western blot analysis. Confluent HEK cells transiently transfected with expression constructs were placed on ice and washed twice with ice-cold PBS. Cells were scraped from the dishes and homogenized in a hypotonic buffer (0.25M sucrose, 10 mM Tris-HCl, 10 mM NaCl, 1 mM EDTA, pH7.5) supplemented with mixture of protease inhibitors (Complete; Roche). The lysate was centrifuged at 3,300 g for 5 min. to remove nuclei and the supernatant was used as total cytosolic protein. The samples were run on a 4-20% gradient SDS-polyacrylamide gel and transferred onto a nitrocellulose filter (0.45 μm; Schleicher & Schuell) using an electroblot apparatus (Bio-Rad) at 100V for 1 hr in transfer buffer [25 mM Tris-HCl, 192 mM glycine, 0.1% SDS, 20% (v/v) methanol]. The filter was incubated in blocking solution [50 mM Tris-HCl, 200 mM NaCl, 1 mM $MgCl_2$, pH7.4] containing 3.5-10% non-fat dry milk powder at 37° C. for 1 hr. The membrane was processed through sequential incubations with primary antibody [anti-EFHC1 at 1:1000 dilution, mouse anti-GFP monoclonal antibody (Roche) at 1:1000 dilution, rabbit anti-Myc polyclonal antibody (Cell Signaling) at 1:1000 dilution, goat anti-HA antibody (Roche) at 1:1000 dilution, or anti-Flag HRP (horseradish peroxidase) conjugate (Sigma) at 1:1000 dilution] for 1 hr, and then with 0.4 μg/mHRP-conjugated secondary antibody (Santa Cruz Biotechnology) Immunoreactive proteins on the filter were visualized using the Western Lighting™ Chemiluminescence Reagent Plus (Perkin Elmer Life Sciences).

Example 9

Accession Numbers

Transcript A of human EFHC1: AK001328, Transcript B of EFHC1: AL122084, EST clone of human EFHC1: AY608689, Mouse EFHC1 ortholog: AK006489. Pig EST clone: AW344780, Cow EST clones: BE666117 and AV595456.

c.475C>T (Arg159Trp): rs3804506,
c.545G>A (Arg182His): rs3804505.

| Gene name | Accession numbers |
|---|---|
| Transcript A of human EFHC1 | AK001328 |
| Transcript B of human EFHC1 | AL122084 |
| EST clone of human EFHC1 | AY608689 |
| Mouse EFHC1 ortholog | AK006489 |
| Pig EST clone | AW344780 |
| Cow EST clones | BE666117 and AV595456 |
| c.475C > T (Arg159Trp) | rs3804506 |
| c.545G > A (Arg182His) | rs3804505 |

Example 10

Juvenile Myoclonic Epilepsy: Basic Mechanisms of Convulsions and Absences

Juvenile myoclonic epilepsy, a common form of epilepsy, accounts for at least 6 to 12 percent of all epilepsies. Its full phenotype consists of adolescent onset myoclonias; grand mal (clonic-tonic-clonic) convulsions and absences associated with EEG diffuse polyspikes and slow waves. Pure "grand mal" convulsions are "tonic-clonic-tonic seizures" and the terms are used interchangeably. One endophenotype is the asymptomatic member who only has the EEG polyspike wave trait. Neuropathology reveals increased number of and diffusely distributed dystopic neurons in gray matter stratum moleculare and subcortical white matter of JME brains. Quantitative high resolution MRI detects such JME neuropathology as "significantly larger and thicker cerebral cortical gray matter volumes." Genton, et al., *Epilepsia*, 32: S3,45, 1991; Genton, et al., *Arch. Neurol.*, 58: 1487-1490, 2001; Manford, et al., *Arch. Neurol.*, 49: 801-808, 1992; Goosses, *Frei Berlin University, West Berlin*, 1984; Meencke et al., *Adv. Neurol.*, 79: 123-131, 1999; Woermann, et al., *Brain*, 122: 2101-2108, 1999.

An objective is to study the mutated gene, EJM1A, for Juvenile Myoclonic Epilepsy (JME) in order to understand the basic mechanisms of convulsions and absences. To understand the molecular basis of JME phenotypes, a putative gene, EJM1A, in chromosome 6p12 was identified. The project will study EJM1A, which is a novel gene encoding a protein with an EF hand motif that regulates R-type high voltage dependent calcium channels or $Ca_v2.3$ and apoptosis. EJM1A encodes a 640 amino acid protein, myoclonin1/EFHC1. EJM1A spans 72 kb, has 11 exons, three DM10 domains, and a motif of unknown function. Mutation analysis of EJM1A in 31 JME Mexican families revealed 6 missense mutations segregating in 25 epilepsy or EEG polyspike-wave affected members of six unrelated families but not in 382 unrelated healthy controls. Myoclonin1/EFHC1 overexpression in mouse hippocampal primary culture neurons induced apoptosis that was significantly lowered by JME mutations. The apoptosis was specifically suppressed by SNX-482, an antagonist of R-type voltage-dependent $Ca^{2+}$ channel ($Ca_v2.3$). Myoclonin1/EFHC1 and $Ca_v2.3$ immunomaterials overlapped in mouse brain, and Myoclonin 1/EFHC1 co-immunoprecipitated with $Ca_v2.3$ C-terminus. In patch-clamp analysis, myoclonin1/EFHC1 specifically increased R-type calcium currents that were reversed by JME mutations. These observations strongly favor myoclonin1/EFHC1 as the EJM1A gene.

Figure 7:
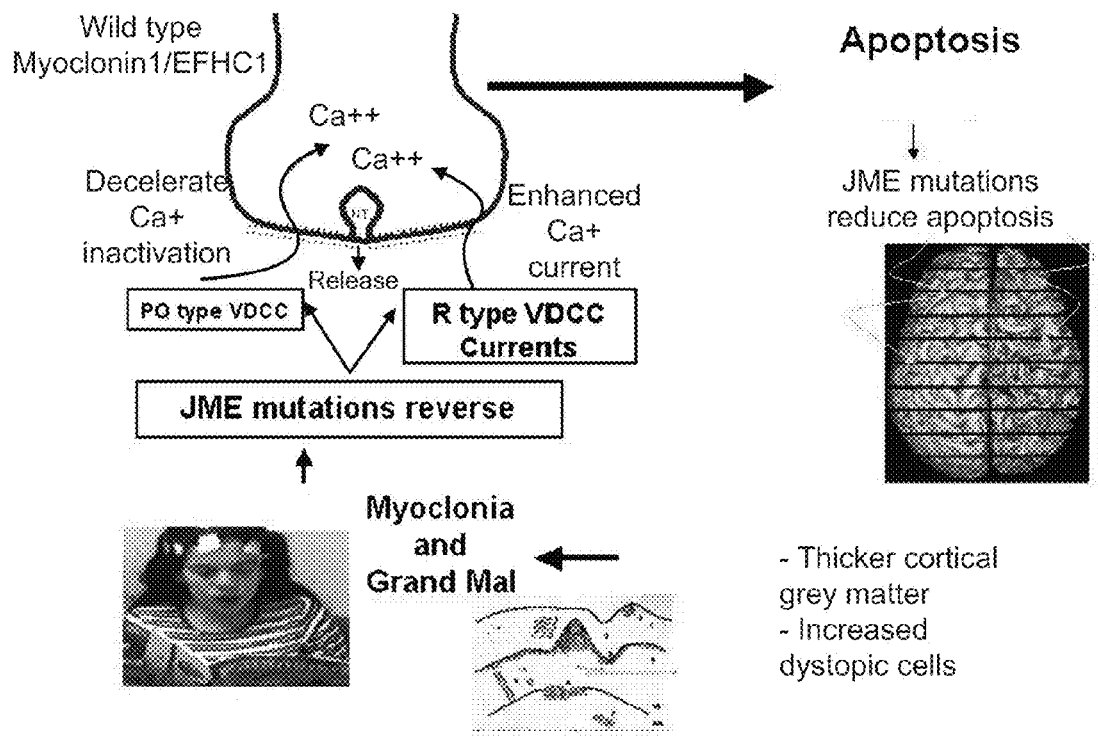
FIG. 7 shows pathogenesis of seizures in JME: Dysregulated $Ca_v2.3$ and apoptosis failure.

Mutations in Myoclonin1/EFHC1, a gene with apoptotic activity, may cause myoclonias, grand mal and absence seizures in JME? One hypothesis states that JME mutations, by compromising EFHC1's apoptotic activity through $Ca_v2.3$, prevent elimination of unwanted neurons during CNS development, lead to increased density of dystopic neurons with dysregulated calcium homeostasis, and predispose to myoclonias and tonic clonic convulsions. FIG. 7. shows that JME mutations reduce apoptosis and dyregulate $Ca^{2+}$. Thicker cortical grey matter is shown by MRI (Woermann et al. 1998), and there is an increased number of dystopic cells in stratium molecular and subortical white matter. A further hypothesis states that mutations in myoclonin1/EFHC1 alters its binding to SNAP25, impair modulation of $Ca_v2.3$, tilting the balance to more low voltage activated T type calcium currents in thalamus, leading to cortical spike waves and absences.

In order to understand the basic mechanisms of convulsive and absence seizures in JME two approaches will be taken:

(1) A study of calcium modulation will test the role of newly identified mutations and variants in $Ca_v2.3$ regulation and compare them with myoclonin1/EFHC1 action on R type ($Ca_v2.3$) and P/Q type calcium channels ($Ca_v2.1$) by patch clamp analyses of human embryonic kidney (HEK) cell lines. Transcripts (2.3 kb, 4.4 kb, 7.5 kb and 9.5 kb) and antiepileptic drugs that suppress JME seizures will be studied for their effects on $Ca_v2.3$ and $Ca_v2.1$ regulation.

(2) A study of myoclonin1-SNAP25 interaction will continue an investigation of wild type myoclonin1-SNAP25 interaction using in vitro GST pull down experiments and in vivo by co-immunoprecipitation from transfected HeLa cells expressing both proteins. In vitro and in vivo binding of myoclonin1/EFHC1 missense mutations to SNAP25 proteins will then be assessed. Confocal microscopy will study the expression profile of myoclonin1/EFHC1/SNAP25 complex using double labeling techniques with specific polyclonal antibodies in developing and adult wild type mice cerebrum, cerebellum, thalamus, hippocampus and brainstem. Understanding the molecular mechanisms of grand mal convulsions and absence seizures will lead to therapeutic treatments in Juvenile Myoclonic Epilepsy.

Juvenile Myoclonic Epilepsy, a common form of epilepsy, is genetically heterogeneous. Amongst the idiopathic generalized epilepsies (IGEs), various authors consider juvenile myoclonic epilepsy (JME), childhood absence epilepsy (CAE) and pure grand mal on awakening as common varieties of epilepsies. If not the most frequent form of IGE, JME is the most common cause of primary grand mal seizures. Most hospital/clinic-based reports calculate that JME accounts for at least 12 percent of all epilepsies while population based prevalence studies placed JME as responsible for 6 percent of all epilepsies. See FIG. 7. Delgado-Escueta, et al., *Neurology*, 34: 285-295, 1984; Nicoletti, et al., 1999; Delgado-Escueta, et al., *Adv. Neurol.*, 89: 161-184, 2002; Delgado-Escueta, et al., *Epilepsy and Movement Disorders*, Cambridge University Press, pp. 421-450, 2002; Thomas, In: Roger, et al., (editors) *Epileptic syndromes in infancy, childhood and adolescence* 3$^{rd}$, Eastleigh: John Libbey & Co. Ltd., Chapter 24, pp. 335-355; Goosses, *Frei Berlin University, West Berlin*, 1984; Thomas, In: Roger, et al., (editors) *Epileptic syndromes in infancy, childhood and adolescence* 3$^{rd}$, Eastleigh: John Libbey & Co. Ltd., Chapter 24, pp. 335-355; Manford, et al., *Arch. Neurol.*, 49: 801-808, 1992; Genton, et al., In: Delgado-Escueta, et al., *Myoclonic Epilepsies, Adv. Neurol.*, 2004, in press.

Juvenile myoclonic epilepsy has been associated with a mutation in the GABRA1 gene on chromosome 5q34-q35 in one large family from Quebec, with a mutation in the CACNB4 gene on chromosome 2q22-q23 in one woman, with a mutation in the CLCN2 gene on chromosome 3q26 in one family from Germany and with SNPS in the BRD2 gene and its promoter region on chromosome 6p21 in JME European American families from New York City. However, with the exception of the report by, these Mendelian epilepsy genes cannot explain the complex genetics of JME, its intermediate clinical phenotypes and EEG endophenotype of "asymptomatics with polyspike waves only." Cossette, et al., *Nat. Genet.*, 31: 184-189, 2002; Escayg et al., *Am. J. Hum. Genet.*, 66: 1531-1539, 2000; Haug, et al., *Am. J. Hum. Genet.*, 69(S4): 226, 2001; Heils, et al., *Epilepsia*, 42(S7): 22, 2001; Pal, et al., *Am. J. Hum. Genet.*, 71: 442, 2002.

EJM1A, a gene that encodes a protein with an EF hand (Myoclonin/EFHC1) is mutated in Spanish Amerind families with JME. In 1988, 1995-1996 and 2001-2002, the locus for "classic JME" in chromosome 6p12-11 (EJM1A) from 7cM to a 1MB region occupied by D6S1714/D6S1960 and D61573 was mapped and refined using families from Los Angeles, Mexico and Belize assuming an autosomal dominant model with 70% reduced penetrance. Thirty-one Mexican families were used for recombination mapping and mutation analyses. A physical map covering the entire region and identified 18 genes was made. All 18 genes were excluded by mutation screening except for the myoclonin/EFHC1 gene. EJM1A (GenBank Acc. No. AK001328) lies between D6S1960 and 180e22 and has mutations that segregate with both clinically and EEG affected members of six families amongst 31 JME families from Mexico. The EJM1A gene spans approximately 63 kb, contains at least 11 exons, and encodes a protein of 640 amino acids. See FIG. 7. A domain search through InterPro and Pfam databases revealed an EF-hand motif (pfam 00036; E-value=0.00066) between amino acid residues 578 to 606. EJM1A was named the myoclonin/EFHC1 gene for EF-hand containing 1. The canonical EF-hand motif has two cooperatively interacting domains each of which consists of two perpendicularly placed alpha helices termed E and F, connected by a calcium-binding loop. C-terminal EF-hands are found in neuronal calcium sensors, the calmodulin family, $Ca^{2+}$ ATPase, $Ca^{2+}$ activated $K^+$ and $Ca^{2+}$ channels, and various novel calcium binding proteins such as calsenilin, DREAM, and KchIP3 (Braunewell and Gundelfinger 1999). Greenberg, et al., *Am. J. Hum. Genet.*, 66: 508-516, 2000; Liu, et al., *Amer. J. Hum. Genet.*, 57: 368-381, 1995; Liu, et al., *Amer. J. Med. Genet.*, 63(3): 438-446, 1996; Serratosa, et al., *Ann. Neurol.*, 39: 187-195, 1996; Bai, et al., *Am. J. Med. Genet.*, 113: 268-274, 2002; Morita, et al., *Am. J. Hum. Genet.*, 69: 534, 2001; Braunewell, et al., *Cell Tissue Res.*, 295: 1-12, 1999.

Mutation analysis in 31 JME families of all 11 exons and intron-exon boundaries of the myoclonin/EFHC1 gene revealed four heterozygous and one doubly heterozygous missense mutations in 24 epilepsy-affected or EEG polyspike-wave-affected members of seven unrelated JME families from Mexico and Los Angeles (see manuscript in Appendix 2). These mutations were not observed in 382 healthy controls (252 Mexicans, 96 Japanese, 34 Caucasians), implying they are not neutral polymorphisms. Double heterozygous mutations (Pro77Thr and Arg221His) were found in affected members of families #1 and #2. In families #3 and #4, c.685T>C resulted in an amino acid change from phenylalanine to leucine at codon 229 (Phe229Leu). In family #5, nucleotide change c.628G>A resulted in amino acid substitution Asp210Asn. Affected members of the family #6 were heterozygous for the mutation Asp253Tyr (c.757G>T).

Arg182His variant in the novel gene with EF hand motif also segregate with 23 affected members of five JME Spanish Amerind families and is significantly associated with 124 index cases of JME. A coding polymorphism, rs3804505 (G/A, Arg182His), was genotyped by dHPLC, TaqMan allelic discrimination and direct sequence (see manuscript) in 99 members of a large Spanish Amerind family from Belize linked to 6p12, including 10 affected members, 68 non affected family members and 21 married ins. 322 unaffected and unrelated Spanish Amerinds were also genotyped. All 10 affected members were heterozygous (G/A). Amongst 68 nonaffected members, 11 had alleles G/A (16.2%). Of 21 married-ins, three share the allele G/A (14.7%). For 322 population controls, 25 show G/A (16.6%). Differences were statistically significant between affected and nonaffected family members (x2=20.44, p<0.001) versus married-ins (x2=20.44, p<0.001), and versus population control (x2=38.10, p<0.001). This suggests that the variant rs3804505 (G/A Arg182His) is statistically associated with affected of this large family with JME, contributing to the risk of JME. This is significant because this variant only partly reverses wild type myoclonin actions and effectively acts like the wild type myoclonin/EFHC1 in decelerating inactivation of PQ type VDCC, enhancing R type VDCC currents and inducing apoptosis.

SNP Rs3804505 were also observed to be significantly associated (p<0.05) with 124 unrelated JME index cases compared to 322 case controls.

Preliminary studies show that Arg182His variant is also commonly found in JME patients from Japan. Because the origin of the Japanese race, according to Y chromosome studies, is near the area of Siberia where American Indians originate (Bianchi et al., 1998), a preliminary screen queried whether the same Arg182His variation is present in JME patients from Japan. The prevalence of Arg182His variation is 38% in Japanese JME patients compared to 8% in healthy controls from Japan and Mexico ($x^2$=12.7, P<0.01 for Japanese patients).

The complex genetics of JME may consist of rare/infrequent mutations and common variants that confer a wide range of susceptibility. It is commonly held that genes with low allele frequency and high displacement (Mendelian or near Mendelian inheritance [Risch, 2001]) are those that are usually identified by linkage and positional cloning. Individuals with these genes are in the tails of the risk distribution, which favors ascertainment of alleles with large phenotypic effects, high penetrance and classically Mendelian appearance in families (Weiss and Terwilliger, 2000). In fact, common alleles with sufficiently large displacement have been rarely detected by linkage. And so, it is reasonable to ask—do variants in exons, such as Arg182His, or in intronic regulatory sites within myoclonin/EFHC1 contribute varying degrees of risk (from small to modest) in Spanish Amerinds? Do variants such as Arg182His have any effect, perhaps small, on risk in European Americans? To answer these questions, a project screens for mutations and variants in myoclonin/EFHC1 in 600 JME patients from Mexico, California and Central America. Results are contrasted in Spanish Amerinds versus European Americans. Myoclonin variants are mapped by linkage dysequilibrium based association studies (Smith et al., 2001; McKeigur et al., 1997, 1998). Two recent examples of a rare gene variant associated with a common disease are NOD2 leucine rich repeat variants in Crohn disease (Hugot et al., 2001; Ogura et al., 2001) and an intronic SNP in PDCD1 (programmed cell death 1) in Lupus erythematosus (Prokunina et al., 2002). Risch, *Nature,* 405: 847-856, 2000; Weiss, et al., *Nature Genetics,* 26: 151-157, 2000; Smith, et al., *Amer. J. Hum. Genet.,* 69(5): 1080-1094, 2001; McKeigue, *Amer. J. Hum. Genet.,* 60: 188-196, 1997; McKeigue, *Am. J. Hum. Genet.,* 63: 241-251, 1998; Hugot, et al., *Nature,* 411: 599-603, 2001; Ogura, et al., *Nature,* 411: 603-606, 2001; Prokunina, et al., *Nature Genetics,* 32(4): 666-669, 2002.

Phenotype and genotype correlate with functions of myoclonin/EFHC1. The only known functional domain of myoclonin/EFHC1 is the EF-hand motif suggesting a role in sensing, binding and modulating neuronal calcium. Mutations in subunits of calcium channels in stargazer, tottering and lethargic epileptic mice emphasize the critical role of calcium homeostasis in the pathogenesis of epilepsy. Because of its EF-hand calcium-sensing motif and because of abnormalities reported in epilepsies, the first functional studies investigated the effects of myoclonin/EFHC1 on voltage-dependent $Ca^{2+}$ channels (VDCCs). Burgess, et al., *Cell,* 88: 385-92, 1997; Cox, et al., 1997; Letts, et al., *Nat. Genet.,* 19: 340-7, 1998; Kawasaki, et al., *Protein Profile,* 1: 343-517, 1994; Heizmann, et al., *Trends Neurosci.,* 15: 259-264, 1992; Kullman, 2002; Fletcher, et al., 1996; Burgess, et al., *Cell,* 88: 385-92, 1997; Letts, et al., *Nat. Genet.,* 19: 340-7, 1998.

ω-Agatoxin IVA sensitive PQ type VDCC ($Ca_v2.1$) and transfected human embryonic kidney (HEK) cell line with P/Q type VDCCs and wild type EFHC1 or mutant constructs were studied. See FIG. 8. Patch-clamp analyses showed EFHC1 significantly decelerated inactivation speed and shifted voltage dependence of inactivation toward positive potentials. EFHC1 did not significantly affect voltage dependence of activation (See Table 1) or other parameters such as $Ca^{2+}$ current density.

TABLE 1

EFHC1 shifted the half-maximal voltage of PQ type VDCC inactivation

| | Activation | | | Inactivation | | |
|---|---|---|---|---|---|---|
| | N | $V_{0.5}$ (mV) | k (mV) | N | $V_{0.5}$ (mV) | K (mV) |
| Vector | 12 | 19.3 ± 1.2** | 9.03 ± 0.58 | 13 | −14.2 ± 1.9** | 6.38 ± 0.21 |
| EFHC1-WT | 14 | 23.9 ± 1.0 | 8.63 ± 0.35 | 14 | −8.0 ± 0.8 | 6.73 ± 0.15 |
| P77T | 5 | 23.0 ± 3.2 | 8.87 ± 1.67 | 5 | −15.8 ± 1.4*** | 6.59 ± 0.44 |
| D210N | 11 | 24.1 ± 1.4 | 9.08 ± 0.71 | 11 | −9.4 ± 1.4 | 6.44 ± 0.33 |
| R221H | 7 | 17.7 ± 1.9 | 7.08 ± 0.81 | 8 | −17.0 ± 2.5*** | 7.00 ± 0.27 |
| F229L | 4 | 21.0 ± 3.4 | 9.25 ± 0.43 | 6 | −13.7 ± 2.4** | 6.53 ± 0.41 |
| D253Y | 7 | 19.7 ± 2.0 | 7.60 ± 0.51 | 7 | −10.9 ± 1.8 | 6.08 ± 0.22* |

N, Number of cells recorded;
$V_{0.5}$, half-maximal voltage of activation and inactivation;
k, slope factor.
Data points are mean ± SEM.
*p < 0.05,
** p < 0.01,
*** p < 0.001 (compare with wild type EFHC1).

JME mutations, P77T, R221 and F229L abolished the decelerating effect of EFHC1 on calcium inactivation.

D210N did not significantly affect calcium inactivation (See Table 1). D253Y mutant reduced the sustained component of calcium currents compared with the vector-transfected control P/Q-type-expressing cells. Mutant D253Y, however, prominently increased current densities while P77T moderately increased $Ca^{2+}$ density. Other mutants did not have effects on $Ca^{2+}$ current density. As a whole, EFHC1 effects on calcium inactivation were extensive and unique, even when compared to effects of $Ca^{2+}$ channels' auxiliary subunits. Wakamori, et al., *J. Biol. Chem.*, 273: 34857-34867, 1998; Letts, et al., *Nat. Genet.*, 19: 340-7, 1998.

The effects of EFHC1 on SNX-482 sensitive R-type VDCC were investigated. Patch clamp analyses of baby hamster kidney (BHK) cells co-transfected with R-type VDCC and EFHC1 expression constructs revealed that EFHC1 significantly increased R-type VDCC currents. JME mutations again partly reversed the increased R-type Ca2+ currents (see manuscript in Appendix 2).

Since EFHC1-elicited gain in resistance to inactivation may potentiate calcium influx through P/Q—type channels and since EFHC1 directly increases R type calcium currents, downstream cellular responses may result. mouse hippocampal neurons in cell cultures were transfected with wild type EFHC1 and characterized neuronal differentiation and neurite outgrowth. Sixteen hours after transfection, GFP-EFHC1 positive neurons showed shorter neurites and less branches in contrast to neurons transfected by pEGFP vector only. Forty-eight hours after transfection (see manuscript in Appendix 2) all GFP-EFHC1 positive neurons exhibited signs of neurodegeneration and cell death including shrinkage of cell body and fragmentation of processes. Control cultures transfected with pEGFP vector showed no features of degeneration (see manuscript in Appendix 2). EFHC1 transfected cells were TUNEL positive indicating apoptosis. The effects of EFHC1 mutations on cell survivability was investigated by counting GFP-positive surviving cells attached to the dishes at various time points, irrespective of cell morphologies. Cell death effects of EFHC1 were significantly reduced by any of the 5 JME mutations or the double mutation P77T/R221H. The three coding polymorphisms identified in control population did not affect cell death effects of EFHC1. The effects of EFHC1 isoforms on cell survival was assessed. Transcript B expression construct (named as iso) produced moderate cell death effects and Wild type co-expression showed intermediate effects. The cellular functions and effects on VDCC by isoform protein encoded by transcript B are presently unknown.

One hypothesis states that dysregulated $Ca_v2.3$/Apoptosis failure leads to myoclonias and convulsions. Thus, studies, so far, allow a proposal that myoclonin/EFHC1 decelerates PQ type calcium inactivation and enhances R type VDCC currents effectively increasing calcium influx. Increased calcium influx, in turn, stimulates programmed cell death in hippocampal cells. JME mutations by compromising EFHC1's apoptotic activity through $Ca_v2.3$, prevent elimination of unwanted neurons during CNS development, lead to increased density of neurons with precarious calcium homeostases, produce hyper-excitable circuits myoclonias and grand mal. The results explain neuropathological findings of microdysgenesis and the structural thick cerebral cortex in JME detected by voxel based quantitative MRI and 2FDG PET scans. See FIG. 7. Woermann, et al., *Brain*, 122: 2101-2108, 1999.

Another hypothesis states that JME mutations lead to abnormal Myoclonin/EFHC1 SNAP25 interaction, altering HVACC currents, tilting balance to more LVDCC currents and cortical spike wave generation.

Consistent with the "calcium myristolation" function of myoclonin/EFHC1 is the identification by the yeast two-hybrid system of SNAP25 or soluble NSF (N-Ethylmaleimide sensitive factor) attachment proteins25 as a major recombinant protein myoclonin/EFHC1 interacts with. Genetic deletion in mice of one copy of synaptic SNAP25 that interacts with high voltage dependent calcium channels or HVDCC results in spike waves and absence epilepsy. While dysregulated $Ca_v2.3$ could explain convulsive grand mal and myoclonias, binding of SNAP25 by a mutated myoclonin/EFHC1 could impair HVDCC, tilting the balance to low voltage activated T-type VDCC in thalamus leading to cortical spike waves and absence seizures in JME. SNAP25 is a palmitoylated peripheral membrane protein that is cleaved by Botulinum toxins A and E and binds to syntaxins. SNAP-25 is found both on the plasma membrane and on synaptic vesicles and is involved in synaptic vesicle trafficking and exocytosis. The synaptic vesicle protein called synaptobrevin is cleaved by Botulinum toxins B, D, F, G and H and tetanus toxin. Botulinum toxin C1, cleaves two substrates, SNAP-25 and syntaxin, which are codistributed with SNAP-25. The identification of these three synaptic proteins—synaptobrevin, SNAP25 and syntaxin as substrates for Botulinum and Tetanus toxins revealed that these proteins must act during the priming reaction. See FIG. 7. Because the priming reaction involves a partial fusion reaction, these three proteins must be directly involved in the fusion of synaptic vesicles. In support of this notion, the three proteins interact with each other to form a stable trimeric complex. Ames, et al., *Nature*, 389: 198-202, 1997; Zhang, et al., *J. Neurosci.*, 24(22): 5239-5248, 2004.

After fusion, this trimeric complex has to be dissolved and its component proteins must be returned to an active conformation for the next fusion reaction. An ATPase called N-ethylmaleimide-sensitive factor (NSF) performs this function by acting as a chaperone in conjunction with attachment proteins called soluble-NSF attachment proteins (SNAPs). NSF originally was thought to participate directly in the fusion reaction, but it is now clear that this enzyme probably is required to recycle the components of the membrane fusion apparatus into an active conformation. Calcium triggered release of neurotransmitters may then result from binding of multiple calcium ions to synaptotagmin, a relatively low affinity sensor.

Because the exact biochemical functions and physiological role of myoclonin/EFHC1 proteins in living neurons still remains to be clarified, because myoclonin/EFHC1 decelerates PQ-type calcium inactivation and enhances R-type calcium currents, and because myoclonin 1/EFHC1 interacts with SNAP25, whose deletion is known to lead to absences, the study concentrates on its role in calcium modulation and interaction with SNAP25. The protein, myoclonin1, contains sequences of one EF-hand and myristoylisation domain, which is known to be involved with intracellular calcium signaling and exocytosis and potentially epileptogenesis. The protein myoclonin 1/EFHC1, therefore, represents an important molecular target for curative antiepileptic drug design and development.

An international JME consortium as part of the GENetic Epilepsy Studies or GENESS has focused on recruiting large, multiplex families and accelerate further discovery of common epilepsy genes. This consortium has identified the chromosome locus for Absence Epilepsy persisting into adulthood in 8q24 and Absence Epilepsy persisting and evolving into Juvenile Myoclonic Epilepsy in 1p. Advances include: identifying the first 6p12 chromosome locus, refining the map position, constructing a physical map, isolating genes and defining the JME mutations in myoclonin1/EFHC1. Further advances in Lafora's progressive myoclonus epilepsy include: identifying the chromosome 6q24 locus, refining the map position, constructing a physical map of 6q24, isolating genes and defining the EPM2A mutations in Laforin/dual specificity phosphatase. A second Lafora disease gene, EPM2B/malin has been identified. The full-length mouse cDNA clones as well as mouse genomic clones of laforin or EPM2a, has been isolated and mapped to mouse chr 10 (the syntenic region of human chr 6q24) and the EPM2a-exon 4 Ko mice has been produced. The same methods are being applied to produce a knockout mouse model for JME.

The genetics core unit of the international JME consortium of GENESS validates the clinical and EEG phenotypes of the JME patient and family members (see manuscript in Appendix 2 for Inclusion and Exclusion Criteria) and then identify mutations in myoclonin1/EFHC1. Three separate and new cohorts of 30 JME multiplex, multigeneration families recruited and enrolled at Mexico and Honduras are being screening. The genetics core unit is also screening such JME mutations for their effects on myoclonin1/EFHC1 induction of programmed cell death. JME mutations that reverse wild-type myoclonin1/EFHC1 pro-apoptotic activities hypothetically should have a thick cerebral cortex as shown by MRI due to apoptosis failure. Hence, these JME patients are also undergoing high resolution quantitative MRI. Polyclonal antibodies against myoclonin/EFHC1 domains together with in situ hybridization (distribution of gene transcripts) are used for studies of development and functions of myoclonin/EFHC1 in (a) normal wild type mice, (b) autopsy brains of human children, adolescents and adults with no known epilepsy, and (c) autopsy brains of humans with JME. Minassian, et al., *Nature Genet.*, 20(2): 171-174, 1998; Minassian., et al., *Neurology* 8, 55(3): 341-346, 2000; Minassian, et al., *Neurology*, 54(2): 488-90, 2000; Ganesh, et al., *Hum. Mol. Genet.*, 12: 2359-2368, 2003.

The role of various domains of myoclonin1-EFHC1, JME mutations and antiepileptic drugs on ($Ca_v2.3$) and ($Ca_v2.1$) function are being studied to help explain myoclonias and convulsions. The exact molecular interactions between myoclonin1/EFHC1 and SNAP25 are being studied to help explain absence seizures in JME.

A study of the role of calcium modulation will test the role of newly identified mutations and variants in $Ca_v2.3$ regulation and compare them with myoclonin1/EFHC1 action on R type ($Ca_v2.3$) and P/Q type calcium channels ($Ca_v2.1$) by patch clamp analyses of human embryonic kidney (HEK) cell lines. Transcripts (2.3 kb, 4.4 kb, 7.5 kb and 9.5 kb) and antiepileptic drugs that suppress JME seizures will be studied for their effects on $Ca_v2.3$ and $Ca_v2.1$ regulation.

Electrophysiological studies will investigate (a) the cellular action of 2.3 kb, 4.4 kb, 7.5 kb and 9.5 kb transcripts, (b) the effects of antiepileptic drugs (levetiracetam, zonisamide, lamotrigine, topiramate, ethosuximide, phenyloin, carbamazepine), and (c) the action of new JME mutations and variants identified by core activities.

Mechanisms of actions of antiepileptic drugs (AEDs) can provide evidence for epileptogenesis produced by epilepsy genes. The mechanisms of seizure-suppressing AEDs in JME, such as valproate, levetiracetam, topiramate, zonizamide and lamotrigine, remain unexplained. Likewise, the reasons why ethosuximide has no effects and phenyloin and carbamazepine can make seizures worse in JME remain unexplained. Valproate selectively reduces low threshold T type VDCC in rat nodose neurons but not in thalamic neurons. In contrast, ethozuximide reduces T-type VDCC in thalamus neurons. Levetiracetam depressed high voltage activated calcium currents but the specific type of high voltage activated calcium currents have not been defined. Levetiracetam had no effects on T type VDCC. Topiramate (10 µmol/L) decreased the peak of L-type HVDCC. Zonizamide (500 µmol/L) does not alter HVDCC but reduces T type LVDCC in cultured fetal rat cortical neurons. Lamotrigine spares L type but inhibits N type and P type HVDCC. Defining these drugs actions at equivalent "therapeutic" and "toxic" concentrations on wild type myoclonin1/EFHC1 effects and JME mutation effects on both LVDCC and HVDCC could provide further evidence on how JME mutations cause seizures. Those AEDs that suppress JME seizures may reverse the effects of JME mutations on P/Q Type VDCC and R type VDCC (see table in Appendix 3 on concentrations of AEDs to be studied). Kelly, et al., *Neurosci. Lett.*, 116:1-2, 1990; Coulter, et al., *Ann. Neurol.*, 25: 582-593, 1989; Niespodziany, et al., *Epilepsia*, 31: 347, 2000; Suzuki, et al., *Epilepsy Research*, 12: 21-27, 1992.

The biophysics of P/Q type calcium channels is primarily determined by the α1A subunit and less by the smaller auxiliary polypeptides (B, α2d and γ subunits). The α1A subunit forms the pore and is essential for voltage sensing and ion permeation. The cytoplasmic C-terminus of α1A is implicated in β subunit interactions, calcium calmodulin mediated inactivation and G protein mediated regulation. A variety of drugs will be tested including the P type VGCC antagonist w-agatoxin IVA (0.1 µM; Calbiochem, La Jolla, Calif.); the N-type VGCC antagonist w-conotoxin GV1A (1 µM; Calbiochem), and the L-type VGCC antagonist nimodopine or nifedipine (1 µM; Research Biochemicals International, Natick, Mass.), the R-type VDCC antagonist SNX-482 (Peptide Institute Inc), the T-type VDCC antagonist flunarizine (Nacalai Tesque). Human embryonic kidney (HEK) cell line HEK (BI-2) will be stably transfect with $α_{1E}$, (BII), $α_{1A}$, (BI-2), $α_2$/d and $β_{1a}$ subunits will be cultured in DMEM containing 10% fetal bovine serum (FBS), 30 µ/mL penicillin and 30 µg/mL streptomycin. Liljelund, et al., *J. Neurosci.*, 20(19): 7394-7403, 2000; Mori et al., *Nature*, 350: 398-402, 1991; Niidome T, Kim M S, Friedrich T, Mori Y, 1992, *FEBS Lett.*, 308, 7-13; Niidome T, Teramoto T, Murata Y, Tanaka I, Seto T, Sawada K, Mori Y, Katayama K (1994). Stable expression of the neuronal BI (class A) calcium channel in baby hamster kidney cells. *Biochem. Biophys. Res. Commun.* 203: 1821-1827.

To transiently express wild-type or mutant EFHC1, HEK (BI-2) cells will be transfected with the pEGFP-C2 plasmids (Clonetech) containing EGFP fused with cDNA for EFHC1 or its mutants using SuperFect Transfection Reagent (QIAGEN). For control experiments, EGFP is transiently expressed by transfecting HEK (BI-2) with the same amount of pEGFP without the EFHC1 inserts. Cells are trypsinized, diluted with the DMEM medium, and plated onto glass coverslips, 24 hours after transfection. $Ca^{2+}$ currents are recorded 36-48 hr after transfection from GFP-positive cells. Currents from HEK (BI-2) cells are recorded at room temperature (22-25° C.) using patch-clamp techniques of whole cell mode with an EPC-9 amplifier (HEKA, Germany). Preparation of patch pipettes, currents sampling, calcium currents recordings, determination of voltage dependence of activation and inactivation are as described in Suzuki et al. (2004). All values are given as mean±SE.

A study of the role of myoclonin1-SNAP25 interaction will continue an investigation of wild type myoclonin1-SNAP25 interaction using in vitro GST pull down experiments and in vivo by co-immunoprecipitation from transfected HeLa cells expressing both proteins. In vitro and in vivo binding of myoclonin1/EFHC1 missense mutations to SNAP25 proteins will then be assessed. Confocal microscopy will study the expression profile of myoclonin1/EFHC1/SNAP25 complex using double labeling techniques with specific polyclonal antibodies in developing and adult wild type mice cerebrum, cerebellum, thalamus, hippocampus and brainstem.

A study of the role of myoclonin/EFHC1-SNAP25 interaction will continue an investigation of specific protein-protein interaction using the yeast-two hybrid technology, tandem affinity purification and mass spectrometry. Confocal microscopic studies will be used in identifying proteins that interact with Laforin, the gene product of EPM2A in Lafora Disease, using the 2-hybrid system. Ganesh, et al., *Hum. Mol. Genet.*, 12: 2359-2368, 2003.

Duplex-A-yeast two-hybrid system (OriGene Technolgies Inc., Rockville, Md.) can be used to identify arrays of proteins that interlock with myoclonin, namely, the. All experiments were performed in yeast strain EGY48. Bait vector pEG202-Myoclonin was transformed into EGY48 cells using the lithium acetate method as recommended and the transformants then tested for the absence of autoactivation of the lacZ reporter gene. For the library screen, a single colony of EGY48 cells transformed with pEG202-Myoclonin was grown overnight and then transformed with a human fetal brain cDNA library constructed in vector pJG4-5 (OriGene). Approximately $2 \times 10^6$ transformants were plated on YNB (gal)-his-ura-trp-leu selective plates. After incubation at 30° C. for 3-5 days, positive clones were further tested for galactose growth dependence and lacZ expression. Plasmid DNAs were isolated from β-gal-positive clones by growth in YNB (gal)-his-ura-trp-leu plates followed by transformation into *E. coli* KC8. A human fetal brain cDNA library (UNI Zap vector, Stratagene) and adult mouse brain cDNA library (Lambda ZAP vector, Strategene) were screened using the insert of the yeast two-hybrid screen positive clone as a probe. Approximately $2 \times 10^6$ plaques were hybridized overnight and positive clones phages were transformed into plasmids by in vivo excision and the inserts were sequenced.

The screen revealed 10 distinct cDNAs encoding proteins that were capable of interacting with myoclonin and did not interact with negative controls used in the screen. Ten inserts that had a length of 400 to 1000 bp were automatically sequenced. Seven inserts matched to known sequences and three did not match sequences or share homology at the nucleotide level with sequences at GenBank and EMBL databases. Among the seven sequences, four matched to known cDNA sequences: brain creatine kinase (CKB), nucleoporin p54 protein (NUP54), syntaxin and SNAP25. Three sequences matched to known non-coding sequences.

With these observations the myoclonin-EFHC1/SNAP25 complex is characterized by tandem affinity purification (TAP) and mass spectrometry. The cDNA coding for the protein of interest (myoclonin-EFHC1) will be tag at the 3' end or amino/carboxy-terminus with the TAP cassette. The TAP cassette contains two tags that allow two steps of high affinity purification with a very mild site-specific protease treatment to release a pure and intact complex. The constructs will be inserted in a suitable eukaryotic expression vector under control of the CMV promoter. The TAP tagged cDNA of myoclonin-EFHC1 is transfected and overexpressed in a cell line containing the protein of interest. After cell lysis, tandem affinity purification is carried out in two steps. Protein components of the complex are separated by gel electrophoresis and the single bands eluted and then sequenced. As little as 3 ng of protein can be sequenced by mass spectrometry. This technique allows us to determine the stoichiometry of the myoclonin-EFHC1/SNAP25 complex and to isolate and define all other SNAP proteins interacting with myoclonin-EFHC1.

After confirming the interaction between SNAP25 and myoclonin/EFHC1 proteins by the in vitro pull down experiments, the relationship of myoclonin mutations with SNAP25 will be studied by investigating the in vitro binding of myoclonin missense mutations to SNAP25 proteins. Myoclonin-EFHC1 cDNA mutants coding for (1) the double heterozygous mutations (Pro77thr and arg22His) and (2) mutants coding for c.685T>C will be fused to GST in the pGEX-3× prokaryiotic expression vector (Pharmacia) and the corresponding GST-fusion peptide will be expressed and purified from bacterial lysate using the glutathione-sepharose 4B beads (Sigma). The pNMyc-SNAP25 construct will be used for the production of SNAP25 protein by using an "in vitro" transcription and translation system in the presence of 35S-labelled methionine. Purified recombinant GST-tagged myoclonin full-length protein or myoclonin mutants and GST will be incubated with 35S-labelled "in vitro" translated SNAP25. Whether polypeptides of SNAP25 will be retained by GST-myoclonin beads will be determined.

To further characterize the in vivo interaction of SNAP25 and myoclonin/EFHC1 proteins, HeLa cells will be cotransfected with pEGFP-Myoclonin vectors expressing GFP-myoclonin fusion protein and pNMyc-SNAP25 construct expressing Myc-tagged SNAP25 protein to study in vivo binding of myoclonin-EFHC1 mutations to SNAP 25. It will be determine if GFP-myoclonin will immunoprecipitate from cell lysates with anti-GFP antibody and whether co-transfected SNAP25 protein will co-immunoprecipitate with GFP-myoclonin. To determine if the interaction is indeed between myoclonin and SNAP25, one will examine if SNAP25 will be co-immunoprecipitated by anti-GFP antibody in HeLa cells co-transfected with vectors expressing GFP and SNAP25 proteins. Conversely, anti-Myc antibody should also co-immunoprecipitate with the GFP-myoclonin protein from the co-transfected cells while anti-Myc antibody should not co-immunoprecipitate the GFP protein.

Similar experiments will be performed with myoclonin mutants in vivo by transferring them to a eukaryotic expression vector under control of a strong promoter and then transfecting them into HeLa cells. Western blot analyses should confirm if the proteins are expressed and to which extent they are stable. Immunoprecipitation experiments should further tell us if cerebrum, cerebellum and brainstem neuronal cell lines also contain the myoclonin-EFHC1/SNAP25 complex. When antibodies are not yet available against proteins of SNAP family, FLAG tagging for the protein will be used. For each transfection experiment, only one flagged protein can be used. These series of experiments should determine if the mutant myoclonin binds SNAP25 and other SNAPs in vivo, whether a hyperexpressed mutant interacts with the myoclonin-EFHC1/SNAP25 complex and acts as a dominant negative.

Figure 9:
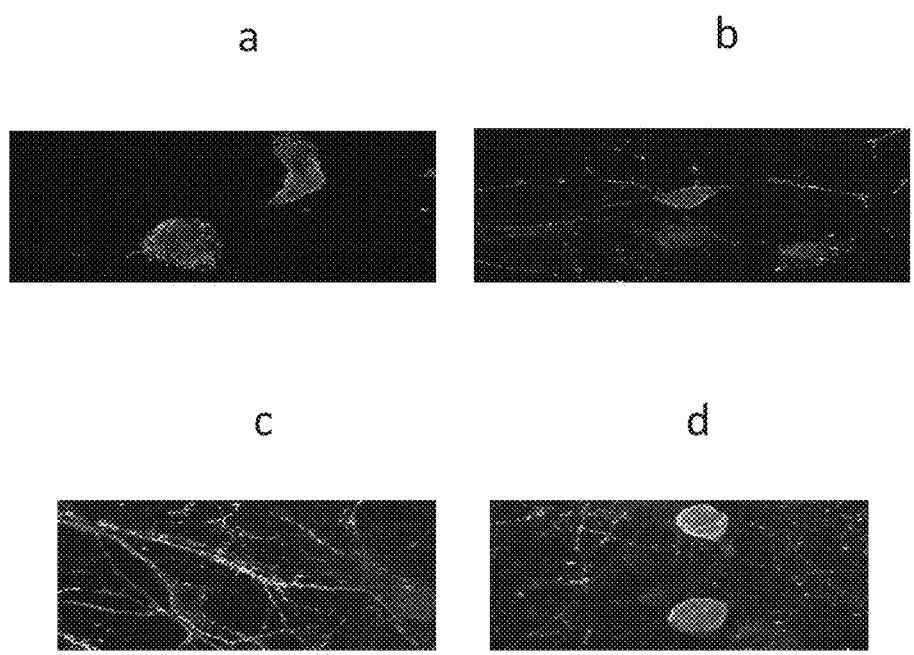
FIG. 9 shows the pattern of expression of myoclonin/EFHC1 proteins in developing and adult wild type mice brain tissue using polyclonal antibodies raised against AB61 and AB62.

The pattern of expression of myoclonin/EFHC1 proteins in developing and adult wild type mice cerebrum, cerebellum, thalamus, hippocampus and brainstem has been studied using polyclonal antibodies raised against AB61 and AB62 and confocal microscopy of the myoclonin-EFHC1/SNAPs complex using double labeling techniques with specific polyclonal antibodies. FIG. 9 illustrates immunocytochemical material of myoclonin/EFHC1 antibodies in neurons (9a), glia (9b) and dendrites (9c: Confoc 100× Ethidium homo 1: blue Ep021061: green MAP-9ab: dendrites), but not axons (9d: Hippoc 18 days Confoc 100× Ethidium homo 1: red Ep021061: green SMI31 axons: blue). Protein product in expression vectors and tissues of "controls" (normal mice brains and normal human brains) and in autopsy brains of patients with idiopathic generalized epilepsies suspected as JME will be characterized. Two such frozen brains are available in the UCLA/VA Brain Bank. Normal, non-JME brain specimens (humans and animals) of different ages are also available. The Brain Bank has provided frozen brain regions from autopsied brain specimens of non-JME adults, adolescents and children who die from accidents as well as surgically excised brain specimens.

Since a polyclonal antibody against SNAP 25 is commercially available, the pattern of expression of myoclonin/EFHC1 and related SNAP25 proteins in developing and adult mice will be studied. Cerebrum, cerebellum, thalamus, hippocampus and brainstem will be studied. Specific polyclonal antibodies against other SNAPs will be generated to see if they also interact with myoclonin The SNAP proteins will be synthesized in the *E. coli* heterologous system using the inducible vector pGEX (Pharmacia) in the correct frame. The coding sequences of the peptides will be inserted in the plasmid fused to a GST tag that allows the simple and rapid isolation of large amounts of proteins by affinity chromatography. Antibodies will be generated to the purified proteins. Double labeling studies in a separate gene product namely laforin has been performed. Ganesh, et al., *Hum. Mol. Genet.*, 11: 1251-62, 2002; Ganesh, et al., *Hum. Mol. Genet.*, 11: 1263-1271, 2002.

Statistical analyses are performed. Voltage dependence of activation and inactivation by JME mutations and transcripts 2.3 kb, 4.4 kb, 7.5 kb and 9.5 kb will be compared to the wild type EFHC1. The effects of antiepileptic drugs on PQ type and R type VDCC will be determined and compared with wild type EFHC1. The effects of antiepileptic drugs on EFHC1 action and on JME mutations effects on PQ type and R type VDCC will also be determined. A student's t-test will be performed for the comparisons, and statistics with probabilities of less than 0.05 will be considered significant.

Example 11

Study to Determine how Mutations in Myoclonin1/EFHC1, a Gene with Apoptotic Activity, Cause Myoclonias, Grand Mal and Rare Absence Seizures in JME Expression of JME mutations may compromise EFHC1 apoptotic activity through Cav2.3, and thus preventing elimination of unwanted neurons during CNS development, leading to increased density of dystopic neurons with dysregulated calcium homeostasis, and predisposition to myoclonias and tonic clonic convulsions. See FIG. 7.

Antiepileptic drugs (AEDs) that suppress or aggravate JME seizures will be used to test how JME mutations produce seizures. These AEDs will be studied to determine how the drugs influence the effects of myoclonin/EFHC1 and JME mutations on $Ca_v2.3$ and $Ca_v2.1$ (P-Q type VDCC) in human embryonic kidney (HEK) cell lines analysed by patch clamp. If JME mutations cause seizures by reversing enhanced $Ca_v2.3$ currents, AEDs that suppress JME seizures should enhance $Ca_v2.3$ currents, diminish thalamic T type VDCC and prevent cortical spike waves. AEDs that aggravate JME seizures and precipitate/prolong absences should inhibit $Ca_v2.3$ currents increase thalamic T type VDCC functions and thalamocortical spike waves.

The site of action of myoclonin/EFHC1 and JME mutations in the apoptotic cascade in transiently transfected primary mouse hippocampal neuronal cell culture will be delineated. Three polyclonal antibodies against myoclonin/EFHC1 domains and in situ hybridization for studies of period and region specific myoclonin1/efhc1 expression during development will be used in (a) wild type mice, (b) autopsy brains of human infants, children, adolescents and adults with no known epilepsy, and (c) autopsy brains of humans with JME. Understanding how myoclonin and JME mutations regulate apoptosis may provide the key to cure or prevent JME.

Quantitative/volumetric MRI will measure cerebral cortical and subcortical matter in clinically affected, EEG affected, and unaffected family members who carry the myoclonin/EFHC1 mutations. If JME mutations cause epilepsy by preventing apoptosis, MRI should show thicker cerebral cortical mantle in JME patients with myoclonin1/EFHC1 mutations. Determining molecular actions of myoclonin1/EFHC1 in $Ca_v2.3$ and $Ca_v2.1$ regulation and in apoptosis can lead to novel and curative drug design and development for Juvenile Myoclonic Epilepsy (JME).

In this millennium, the epilepsies remain the most common serious neurological problem worldwide, afflicting about 40 to 100 million persons. The public health importance of the epilepsies is unquestionable. Epilepsy costs the USA approximately $11.1 to $12.5 billion a year (Begley et al., 2000). The lifetime prevalence of epilepsy in the USA is 2% to 5% affecting an estimated 3 million Americans. Of all epilepsies, idiopathic generalized epilepsies comprise at least 30% in USA, 20% in Mexico, and 8% in Honduras, Panama and Guatemala (Jallon, 1998; Garcia Pedroza et al., 1983; Gracia et al., 1986; Medina et al., 1997; Mendizabal & Salguero, 1996; Rubio Donnadieu et al., 1991). The idiopathic epilepsies comprise a significant proportion of the epilepsies in the USA, because we have diminished many parasitic infestations, such as cysticercosis, poor obstetrical care and early life injuries that cause lesional epilepsies.

Amongst the idiopathic generalized epilepsies (IGEs), various authors consider juvenile myoclonic epilepsy (JME), childhood absence epilepsy (CAE), and pure grand mal on awakening to be common varieties of epilepsies. If not the most frequent form of IGE, JME is the most common cause of primary grand mal seizures. Most hospital/clinic-based reports calculate that JME accounts for at least 12 percent of all epilepsies while population based prevalence studies placed JME as responsible for 6 percent of all epilepsies. However, data suggests that JME may account for even a higher percentage—as much as 20 to 30% of all epilepsies in the Western world for the following reasons. Pure grand mal on awakening is reported by the German school of Janz (Janz, 1957, 1969, 1985, 1998; Goosses, 1984; Tsuboi and Christian, 1973-6) to account for 22% to 37% of all epilepsies. And yet, awakening grand mal epilepsy was observed less frequently in epidemiologic studies in USA, Europe, and Central America and in genetic twin studies in Australia (Berkovic et al., 1994). Moreover, CCTV-EEG telemetry or polygraphy show that awakening grand mal seizures are most often preceded by myoclonic seizures or absences. Delgado-Escueta, et al., *Neurology*, 34: 285-295, 1984; Delgado-Escueta, et al., *Epilepsy and Movement Disorders*, Cambridge University Press, pp. 421-450, 2002; Delgado-Escueta, et al., *Adv. Neurol.*, 89: 161-184, 2002; Thomas, In: Roger, et al., (editors) *Epileptic syndromes in infancy, childhood and adolescence* 3$^{rd}$, Eastleigh: John Libbey & Co. Ltd., Chapter 24, pp. 335-355; Goosses, *Frei Berlin University, West Berlin*, 1984; Nicoletti, et al., 1999; Manford, et al., *Arch. Neurol.*, 49: 801-808, 1992; Genton, et al., In: Delgado-Escueta, et al., *Myoclonic Epilepsies, Adv. Neurol.*, 2004, in press; Medina, et al., 1997; Loiseau, et al., 1964, 1991; Genton, et al., *Epilepsia*, 32: S3,45, 1991; Hauser, et al., 1990; Berkovic, et al., 1994; Delgado-Escueta, et al., *Adv. Neurol.*, 79: 351-374, 1994; Janz, 1969; Roger, et al., 1992.

For many years individuals with JME were presumed to have normal neuroanatomy and intelligence. This notion began to be questioned when reductions were noted in glucose uptake in the premotor cortex and caudate of JME subjects at rest, failure to activate glucose uptake in the dorsal prefrontal cortex during a working memory task, and impaired performance of the same task during [18]FDG-PET neuroimaging. These subjects also showed impairment in motor dexterity, timed tests and verbal fluency, which further supported frontal lobe dysfunction. These findings correlated with neuropathology that showed increased number of "dystopic neurons" in stratum moleculare of gray matter and in subfrontal white matter on autopsy brain specimens of JME patients. Swartz, et al., 1995; Meencke, et al., 1984; Meencke, et al., 1996.

Quantitative MRI detects such neuropathologies and structural changes as "significantly larger cortical gray matter volumes than control subjects" in 8 of 20 JME patients maximal in the frontal central regions. There was no correlation between regional volumes and age, age of onset, duration of epilepsy, incidence of generalized tonic-clonic seizures, or seizure free duration. JME patients with positive family history were more likely to have structural abnormalities than those without. Further evaluations of JME subjects showed significantly thicker cerebral cortex mantle especially in the mesial frontal lobe. In light of the above results by Woermann, et al., 1998, and earlier work on 2 FDG PET scan of JME patients and the hypothesis of dysregulated $Ca_v2.3$ and apoptosis failure in JME, the in vivo neuroanatomy of JME subjects who have a mutation in the myoclonin1/EFHC1 gene will be studied. Woermann, et al., 1998.

Calcium modulation studies will use antiepileptic drugs (AEDs) that suppress or aggravate JME seizures to test how JME mutations produce seizures. AEDs will be studied to determine how they influence the effects of myoclonin/EFHC1 and JME mutations on $Ca_v2.3$ and $Ca_v2.1$ (P-Q type VDCC) in human embryonic kidney (HEK) cell lines analyzed by patch clamp. If JME mutations cause seizures by reversing enhanced $Ca_v2.3$ currents, AEDs that suppress JME seizures should enhance $Ca_v2.3$ currents, diminish thalamic T type VDCC and prevent cortical spike waves.

Investigations include: (a) the cellular action of transcripts (2.3 kb, 4.4 kb, 7.5 kb and 9.5 kb) on $Ca_v2.3$ and $Ca_v2.1$ by patch clamp analyses of human embryonic kidney (HEK) cell lines. (b) The action on $Ca_v2.3$ and $Ca_v2.1$ by new JME mutations and variants identified by the Genetics Core Unit, and (c) contrast the actions of AEDs (valproate, levetiracetam, zonisamide, lamotrigine, topiramate) that suppress JME seizures against AEDs (ethosuximide, phenyloin, carbamazepine) that have no effects on or aggravate JME seizures.

Antiepileptic drugs (AED) will be studied because mechanisms of actions of AEDs can provide evidence for mechanisms of epileptogenesis produced by epilepsy genes. Moreover, understanding AED mechanisms can have practical clinical use. The mechanisms of seizure suppressing AEDs in JME, such as valproate, levetiracetam, topiramate, zonisamide and lamotrigine, remain unexplained. Likewise, why ethosuximide has no effects and phenyloin and carbamazepine can make seizures worse in JME is unexplained. Why phenyloin and carbamazepine make absence appear for the first time or turn rare 2-10 second absences into 30-60 minute absences in JME remain a mystery. VPA selectively reduces low threshold T type VDCC in rat nodose neurons but not in thalamic neurons and yet is most effective in JME. In contrast, trimethadione and ethosuximide reduce T-type VDCC in thalamus neurons but have no effects in JME. Levetiracetam depresses high voltage activated calcium currents but the specific type of high voltage activated calcium currents have not been defined. Levetiracetam had no effects on T type VDCC. Topiramate (10 µmol/L) decreased the peak of L-type HVDCC. Zonisamide (500 µmol/L) reduces T type LVDCC in cultured fetal rat cortical neurons while it enhances N-type $Ca^{2+}$ channel activity and possibly reduces P-type calcium channel activity. Lamotrigine spares L type but inhibits N type and P type HVDCC. Defining these drugs actions at equivalent 'therapeutic' and 'toxic' concentrations on wild type myoclonin1/EFHC1 effects and JME mutation effects on both LVDCC and HVDCC could provide further evidence on how JME mutations cause seizures. Kelly, et al., *Neurosci. Lett.*, 116:1-2, 1990; Coulter, et al., *Ann. Neurol.*, 25: 582-593, 1989; Niespodziany, et al., *Epilepsia*, 31: 347, 2000; Kawata, et al., 1999; Suzuki, et al., *Epilepsy Research*, 12: 21-27, 1992; Okaka, et al., 2002.

Mutant alleles of high-voltage activated subunit genes $Ca_v2.1/\alpha_{1A}$ (tottering/tg; leaner/tg$^{1a}$; rocker/tg$^{rkr}$), $\beta_4$ (lethargic/lh), $\gamma 2$ (stargazer/stg), and $\alpha 2\delta 2$ (ducky/du) have been associated with electrocortical spike-wave discharges in mice resembling those in human idiopathic absence epilepsy. How mutations in high-voltage activated calcium channels produce cortical spike-waves remained a question until recently. Recent analysis of thalamic neurons in tg, lh, and stg mutants revealed not only decreased HVA current densities and altered kinetics, but striking increases in LVA peak currents and channel availability. Studies suggest that the elevated thalamic LVA currents provide a common downstream excitability defect that favors thalamocortical spike wave generation and absence epilepsy. Direct proof for this hypothesis was obtained when studies showed elevated thalamic low-voltage-activated currents preceded the onset of absence epilepsy in the SNAP25-deficient mouse mutant Coloboma. Noebels, 1990; Zwingman, et al., 2001; Zhang, et al., 2002; Zhang, et al., *J. Neurosci.*, 24(22): 5239-5248, 2004.

Figure 10:
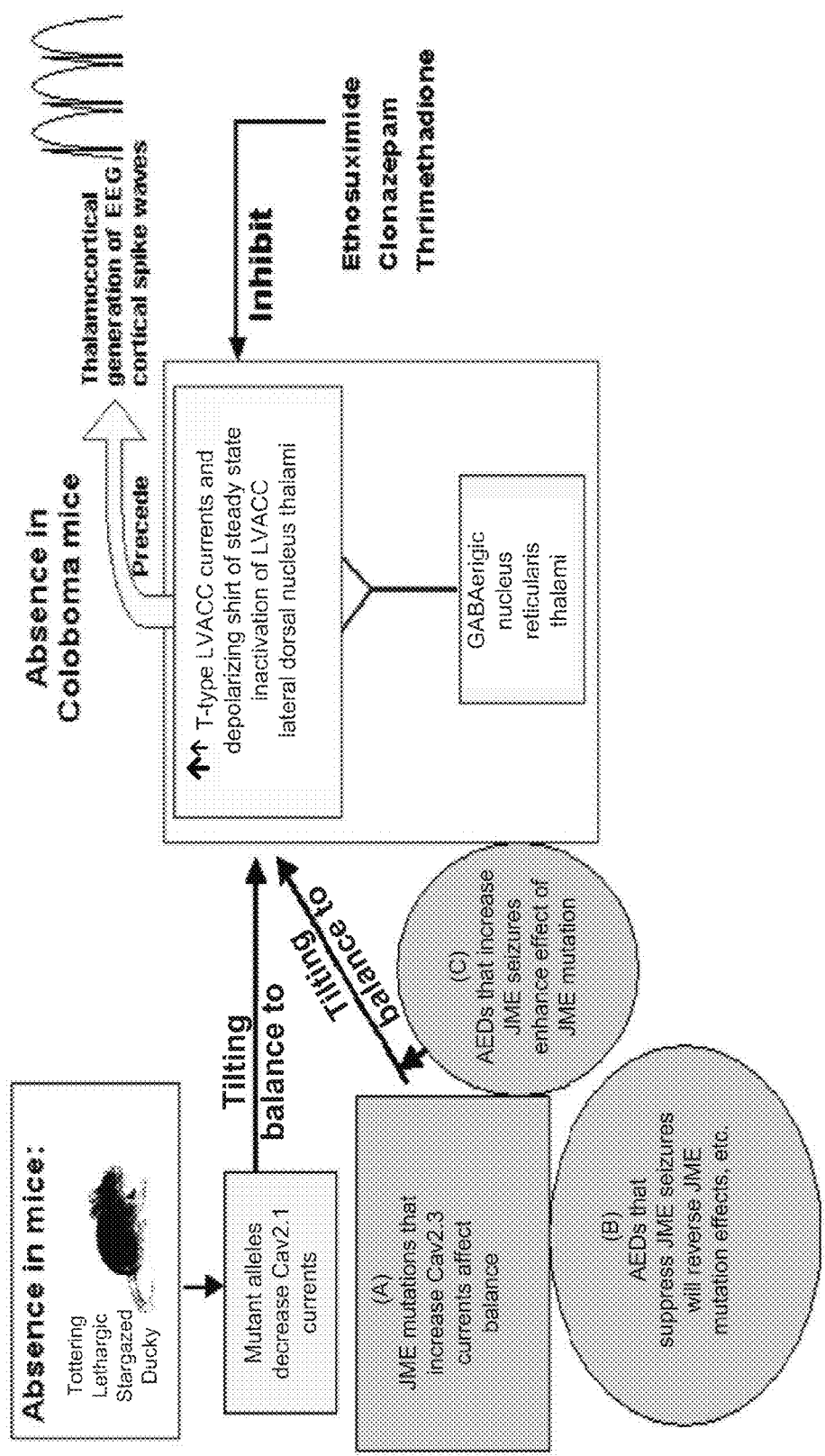
FIG. 10 shows Noebel's hypothesis of thalamocortical spike wave generation compared to a current hypothesis.

JME mutations have an effect on $Ca_v2.3$ and $Ca_v2.1$ and produce seizures. This effect can be explained as follows. In a hypothetical model, a balanced HVACC (high voltage activated calcium channels) and LVACC (low voltage activated calcium channels) prevent thalamic T type LVDCC from generating thalamocortical oscillations and cortical spike waves See FIG. 10. JME mutations reverse the actions of wild type myoclonin1/EFHC1 on $Ca_v2.3$ and $Ca_v2.1$, effectively decreasing HVACC functions. In FIG. 10, the mutant alleles of HVACC-PQ type decrease $CA_v2.1$ currents. The model includes the following questions or hypotheses: (A) "Do JME mutations that increase $Ca_v2.3$ currents and decrease inactivated PQ type $Ca_v2.1$ tilt the balance to increase thalamic T-type LAVCC?", (B) It is anticipated that AEDs that suppress JME seizures will reverse JME mutation effects and enhance $Ca_v2.3$ current and decrease inactivated PQ-type VACC, and (C) It is anticipated that AEDs that increase JME seizures enhance effect of JME mutation. It has been suggested that decreased HVACC functions in JME tilt the balance in favor of increases in thalamic LVACC functions, resulting in thalamocortical oscillations, cortical spike wave generation and seizures. This idea will be tested by studying the actions of antiepileptic drugs that suppress JME seizures and antiepileptic drugs that aggravate JME seizures (See Table 2). Zhang, et al., *J. Neurosci.*, 24(22): 5239-5248, 2004.

TABLE 2

Antiepileptic drugs (AEDs) that suppress or aggravate JME seizures

| AED Myoclonin/EFHC1 JME mutation | Seizure protecting plasma concentrations in humans | "Therapeutic" concentrations to be used in experiments** | Expected results | |
|---|---|---|---|---|
| | | | $Ca_v2.1$ inactivation Decelerate or ↓ Reverse or ↑ | $Ca_v2.3\ Ca^{2+}$ currents Enhance or ↑ Reverse or ↓ |
| (a) Suppress JME seizures | | | | |
| Valproate | 40-150 µg/ml | 0.2-4 mM/L | ↓ | ↑ |
| Levetiracetam* | 5-45 µg/ml | 5-50 µmol/L | ↓ | ↑ |
| Lamotrigine* | 3-14 µg/ml | 5-10 µmol/L | ↓ | ↑ |
| Topiramate* | 5-10 µg/ml | 1-100 µmol/L | ↓ | ↑ |
| Zonisamide | 15-40 µg/ml | 5-500 µmol/L | ↓ | ↑ |
| (b) No effects or aggravate JME seizures or induce absence | | | | |
| Ethosuximide | 40-100 µg/ml | 10-100 µmol/L | No effects | No effects |
| Phenytoin | 10-20 µg/ml | 5-30 µmol/L | ↑ | ↓ |
| Carbamazepine | 4-10 µg/ml | 2-10 µmol/ml | ↑ | ↓ |
| CBZ epoxide | — | 5-30 µmol/ml | ↑ | ↓ |
| Phenobarbital | 10-40 µg/ml | 30-100 µM | ↑ | ↓ |

*Relation between plasma levels and seizure control has either not been established or has not been investigated.
**based on published in vitro experiments.

In this hypothetical model, a balanced HVDCC and LVDCC prevent thalamic T type LVDCC from generating cortical spike waves. Accordingly, in the proposed concept, if JME mutations cause seizures by decreasing myoclonin-enhanced R type VDCC currents, then AEDs that suppress JME seizures should enhance VDCC currents. Likewise, AEDs that aggravate JME seizures and produce or prolong absence seizures, should inhibit HVDCC currents and tilt the balance to LVDCC and enhance thalamic T type VDCC generating cortical spike waves. Full evidence proving thalamic T type VDCC generating cortical spike waves in JME will require testing in a transgenic mice model for JME.

To further investigate the role of apoptosis in development, studies will be conducted to delineate the site of action of EFHC1 in the apoptotic cascade in hippocampal cells in culture Does myoclonin/EFHC1 induce apoptosis by stimulating calcium influx, cause the release of cytochrome c from calcium-loaded mitochondria, bind to Apaf-1, and cleave caspase 3 and proteolyse proteins essential for cell viability? Or, does myoclonin/EFHC1 act upstream of caspase 3 and activate immediate early genes and death signaling proteins, which in turn activate caspases?

Figure 11:
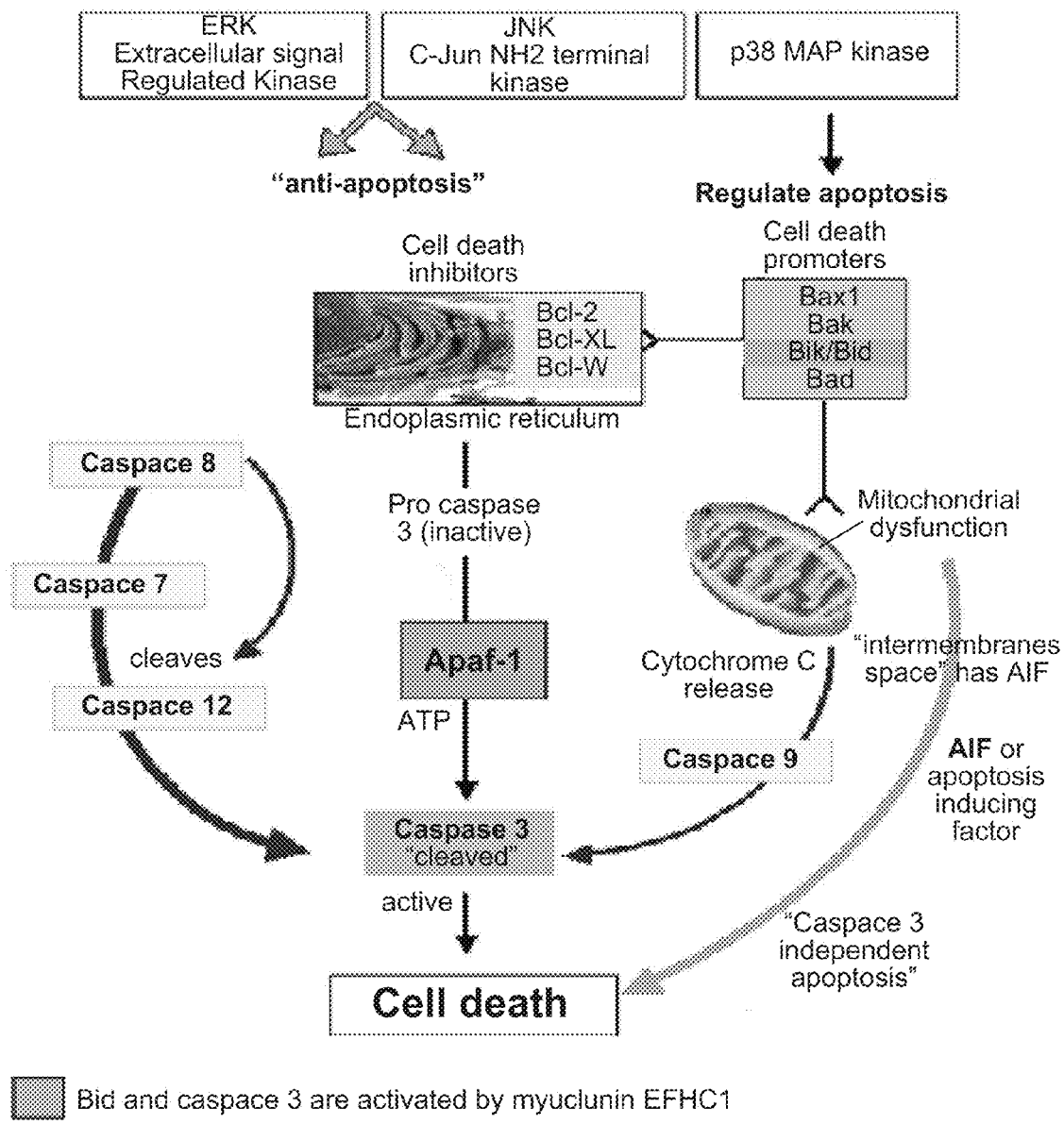
FIG. 11 shows EFHC1/myoclonin 1 activates Bid and Caspase 3 in the apoptosis cascade.

Three sequential phases occur in apoptosis—activation, effector and degradation phases. In the activation phase, biochemical events initiate the machinery of programmed cell death and involve cell organelles notably mitochondriae. Bcl-2 family of proteins protects cells and inhibits apoptosis upstream of Apaf-1 and caspase 3 activation. Bcl-2 blocks the release of cytochrome c from mitochondriae. Certain members of the Bcl-2 family (bax, bak, bid, bad) bind to Bcl-2 and inhibit its function, thus promoting cell death. Apaf-1 possess an ATP dependent hydrolytic activity that promotes cleavage and activation of caspase 3. In the effector phase, other organnelles such as the endoplasmic reticulum act as effectors of apoptosis. Common effector caspases 8, 7 and 12 as well as bax reside in the ER. MAP kinases such as JNK and p38MAP kinase mediate cell death through caspase 3. See FIG. 11. Rosse, et al., 1998; Sakahira, et al., 1998; Kluck, et al., 1997; Li, et al., 1997; Yang, et al., 1997; Zamzami, et al., 1996; Zhivotokovsky, et al., 1998; Zhu, et al., 1998; Liu, et al., 1999; Cheng, 2001; Cohen, et al., 1992; Cohen, et al., 1997; Deckwerth, et al., 1996; Enari, et al., 1998.

The phases of activation and effector are reversible. The degradation phase produces nuclear events, membrane blebbing, internucleosomal cleavage of chromatin by nucleotidase after activation of a calcium calmodulin system and serine proteases, cell elimination by phagocytosis. At this phase rescue from cell death is not possible. Henderson, 1996; Raff, 1998; Hamburger, 1975; Zou, et al., 1997.

Clarifying the exact stage or stages of apoptosis thru which myoclonin/EFHC1 acts and by what stage JME mutations reverse apoptosis is important for development of a curative treatment. Typically, apoptotic stimuli, through a Bcl-2 family mediated checkpoint, cause redistribution of cytochrome-c from mitochondria to cytosol. Cytosolic cytochrome-c binds to APAF-1 in the presence of dATP or ATP, result in recruitment and activation of caspase 9 and subsequent cleavage of caspase 3. Caspase 3 ultimately produces extensive DNA fragmentation. Studies have show that co-expression in fetal mouse primary hippocampal neuron with DsRed-Bid vector, a marker for caspase activation, produce activated Bid in a number of EFHC1-expressing neurons. These results suggest that myoclonin/EFHC1 causes caspase dependent apoptosis in neurons when they are involved in neuronal modeling during brain development. After establishing Bid activation, the next step is to establish that myoclonin acting through Bid, cause mitochondrial cytochrome C release and then caspase 3 activation. After establishing this step, studies will ask whether myoclonin also acts thru the AIF and a caspase 3 independent cell death mechanisms. Studies will ask if p38MAP kinase and JNK have a role in myoclonin-induced apoptosis.

To verify other Bcl-2 cell death promoters participate in the actions of EGFP-tagged myoclonin 1/EFHC1, the expression of bax and caspase 3 will be studied. Activation of bax (a proapoptotic member of the Bcl-2 family) produces a conformational change exposing its C-terminal hydrophobic domain causing its translocation from cytosol to mitochondriae and other membranes producing a loss of mitochondrial membrane potential and release of cytochrome c. As mentioned above, cytochrome c leads to activation of caspase 3 expression. Mouse hippocampal neurons will be transfected in cell cultures with wild type EFHC1 and characterized for neuronal differentiation and neurite outgrowth sixteen hours and 48 hours after transfection. Rosse, et al., 1998; Maarzo, et al., 1998; Chen, et al., 1998.

Figure 12:
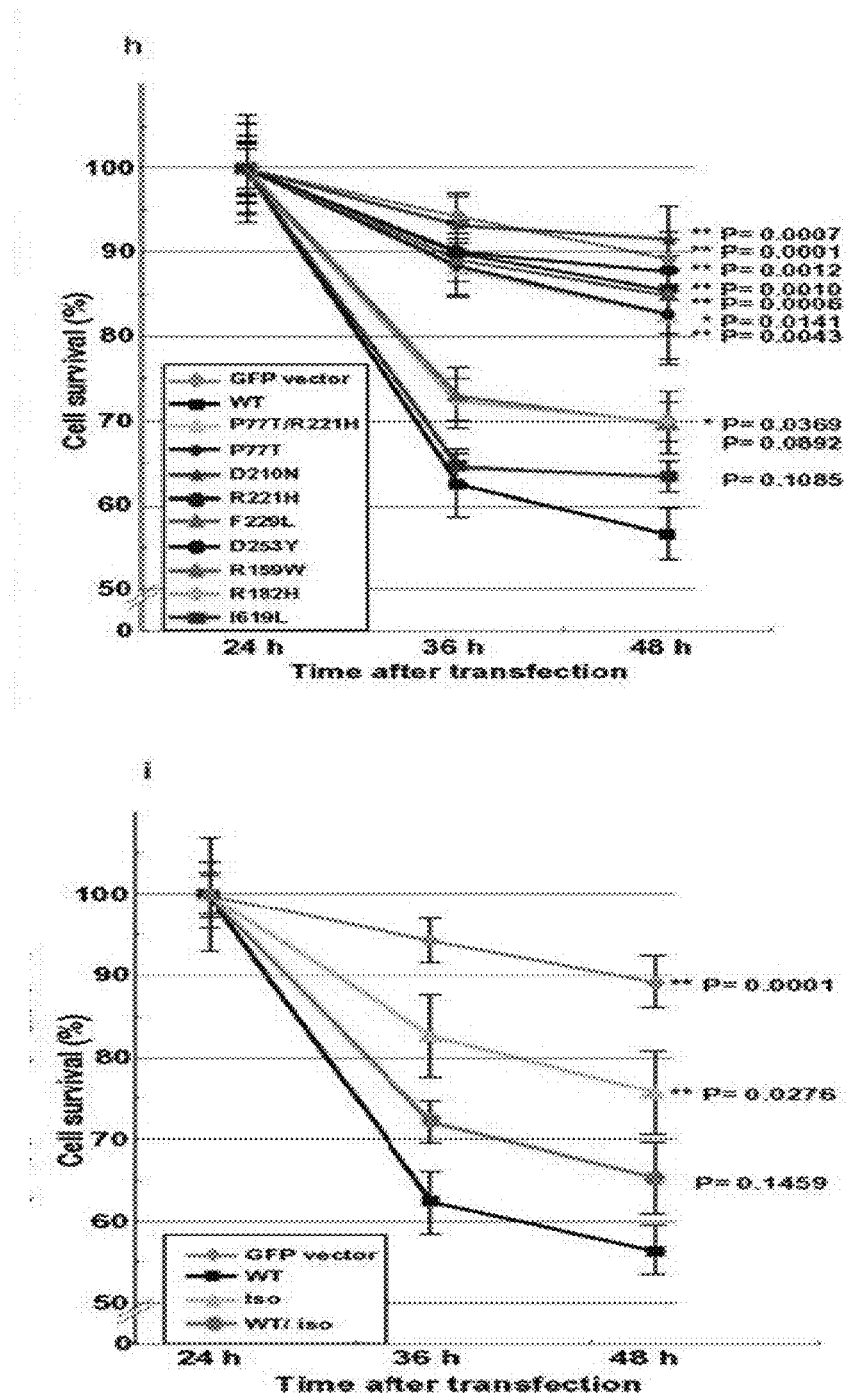
FIG. 12 shows effects of JME mutations or effects of transcript b(iso) on apoptosis.

The effects of EFHC1 mutations on cell survivability will be investigated by counting GFP-positive surviving cells attached to the dishes at various time points, irrespective of cell morphologies. See FIGS. 12a and 12b. After fixation and 1-hr saturation with PB-G, hippocampal cultures will then be further incubated for 10 min with PB-G containing Triton 0.1% then with caspase 3 antibody (rabbit polyclonal antibody to the p20 fraction of caspase3 or caspase 3a) and cytochrome c antibodies (mouse monoclonal antibody to cytochrome c). Double staining will be revealed with anti-mouse mABs conjugated to FITC (1:100 Jackson Immuno Research) and anti-rabbit polyclonal Abs conjugated to Cy3 (1:100 Jackson Immuno Research). After counter staining with Hoechst 33342, the triple label is viewed on a scanning widefield microscope with image deconvolution.

Similar methods will be used for incubations with only rabbit anti-bax antiserum (Oncogene) or only a rabbit anti-caspase 3 antiserum (Santa Cruz Biotechnology). The antisera will be detected by using ABC (Vector Labs) and 3,3 diaminobenzidine (Sigma) with nickel enhancement. The specificity of antisera will be verified by omitting the primary antisera. A stereological approach to quantify immunoreactivity will be used. The total number of immunoreactive material labeled neurons in every fourth section in brain fields will be counted from video images of brain sections. Electronmicroscopy of bax and caspase immunoractive material distribution in hippocampal neurons, and subcellular organelles can provide evidence as to a mechanism of cell death. West, 1993; Wolter, et al., 1997; Rosse, et al., 1998; Marzo, et al., 1998.

For experiments with caspase inhibitors, cultures will be preincubated with caspase inhibitors (Enzyme systems products, Livermore, Calif.) 45 mins before exposure to myocloni1/EFHC1. Inhibitors of caspase 3 (DEVD-fmk (SEQ ID NO: 23)), caspase 9 (LEHD-fmk (SEQ ID NO: 24)) and the general caspase inhibitor ZVAD-fmk and caspase 1 inhibitor (YVAD-fmk (SEQ ID NO: 25)) will be assessed. Neuronal survival is determined by trypan blue assay in 4 wells representing groups of experiments.

Mitochondrial membrane potential will be measured in order to correlate mitochondrial integrity with cytochrome c release. Mitochondria from hippocampal cell cultures will be isolated according to Brustevetsky, et al., 2000, and mitochondrial membrane potential will be assessed with Mitotracker orange dye. If EFHC1 induces apoptosis by loading mitochondriae with calcium, a severe loss of mitochondrial membrane potential is expected with cytochrome C release preceding caspase 3 activation. Niquet, et al., 2003.

Whether AIF is involved in a "caspase 3 independent" apoptosis in the presence of myoclonin/EFHC1 will be investigated. Immunostaining with AIF antibody (QED Bioscience and Sigma), PARP (caspase 3 substrate) antibody together with TUNEL staining will be used to determine whether apoptotic neurons colocalize with active caspase 3.

Studies will determine whether the caspase 8 and caspase 2 apoptotic pathways are involved. For caspase 8 studies, a commercially available enzyme assay substrate (AcIETD-pNA, (SEQ ID NO: 26), BD Biosciences) and inhibitor (Z-IETD-FMK, (SEQ ID NO: 26), 10 uM, R & D Systyems) will be used. For caspase 2 studies, an enzyme activity assay substrate (Ac-IETD-pNA (SEQ ID NO: 26), from BD Biosciences) and inhibitor (Z-VDVAD-FMK (SEQ ID NO: 27) from R&D Systems) will be used.

If results suggest that myoclonin1/EFHC1 action is upstream of the Bcl-2 family of proteins, studies will further determine whether myoclonin 1/EFHC1 acts on MAP kinases as upstream signals that regulate caspase3. Hippocampal cells will be transfected with overexpression vectors of JNK1 and p38 MAP kinase and measurements will determine whether they potentiate myoclonin induced apoptosis and whether JME mutations can block these effects. Experiments can determine if JNK1 or p38 MAP kinase is activated and if p38 inhibitors (MKK3/6) reverse such activation. JNK1/2/3 KO mice (Jackson laboratory) and p38 KO mice can also be used to confirm if JNK or p38 is a specific target of myoclonin1/EFHC1 apoptosis. Reccio, 2002.

Primers will be designed to amplify the complete open reading frame of EFHC1 from human brain cDNA (Clontech) by PCR using Pyrobest™. The PCR product will be cloned into pEGFPC2 (Clontech) or pcDNA3.1 MycHis (Invitrogen) vector. QuickChange site-directed mutagenesis kit (Stratagene) will be used to introduce 5 kinds of mutations in the EFHC1 clone.

Hippocampal neurons will be isolated from embryonic day 16 mice and plated at $2 \times 10^5$ cells per well in 24 well plate containing glass coverslips coated with poly-1-lysine and grown in serum-free NEUROBASAL™ media supplemented with B27, 0.5 mM L-glutamine (Invitrogen) To develop mouse hippocampus primary cultures. On day 4, cDNA encoding wild type and mutant EFHC1 proteins will be transfected into the cells using LIPOFECTAMINE™2000 (Invitrogen). Cultures will be fixed with 4% paraformaldehyde in PBS 16 and 48 hours after transfection, permeabilized with 0.3% Triton X-100, and blocked in 3% normal goat serum in PBS, and treated with monoclonal anti-MAP-2 antibody (1:500; Sigma), anti-Cmyc antibody (1:200; Santa Cruz Biotechnology) and Alexa fluor 594 goat anti-mouse IgG antibody (1:1000; Molecular Probes). The number of apoptotic cells with cells transformed with mutations will be compared to the number of wild type apoptotic cells using a chi square test of contingency.

Terminal deoxynucleotidyl transferase mediated dUTP-biotin nick-end-labeling (TUNEL) is the most widely used histochemical marker of apoptosis, however it does not discriminate between apoptosis, necrosis, and autolysis and does not provide a full proof method to detect apoptotic cells. Therefore TUNEL plus DNA Fragmentation Assay has been used together with inspection of cells by light and electron microscopy. Morphological changes during apoptosis are very specific, namely, EM evidence of plasma membrane blebbing and chromatin condensation. The TUNEL assay uses DeadEnd™ Fluorometric TUNEL System (Promega). Nuclei are visualized with Hoescht 33342 (Molecular Probes). All experiments are carried out in duplicate wells and at least repeated three times. GFP positive neurons are randomly captured on a confocal microscope (OLYMPUS FLUOVIEW). The subset of cells is reconstructed using Canvas 7 software for representative purposes. The survival cell number in 10× field are counted and statistically analyzed 48 hours after transfection for total 15 fields from 3 coverslips per condition. DNA Fragmentation Assay is based on the activation of calcium/magnesium-dependent endonuclease activity that specifically cleaves cellular DNA between regularly spaced nucleosomal units. DNA fragments are visualized as a distinct ladder of DNA bands on agarose gel after isotopic DNA end labeling. To quantify the presence of cytoplasmic nucleosomes we will use the cell death detection ELISA kit (Roche Molecular Biochemicals). Dong, et al., 1997; Grasl-Kraaupp, et al., 1995; Portera-Cailliau, et al., *J. Comp. Neurol.*, 378:70-87, 1997; Kerr, et al., 1991; Wyllie, et al., 1984; Chun, 1998.

To determine which brain region myoclonin1/EFHC1 exert their apoptotic activities, normal sites of distribution will be defined. Certain regions and neuronal populations at different periods of development may be subjected more to myoclonin-induced apoptosis. Myoclonin may be expressed more during periods of apoptosis. Brain MRI of JME patients would suggest that at the frontal lobe, there may be critical sites of myoclonin apoptosis undetected by MRI. Thus, three polyclonal antibodies against myoclonin/EFHC1 domains will be used together with in situ hybridization (distribution of gene transcripts) for studies of region and period specific expression of myoclonin1/EFHC1 during development in (a) normal wild type mice (embryonic days 7, 11, 15, 17, birth, 7, 14, 21 days, 1, 2, 6, 12 and 24 months) (see FIG. 13), (b) autopsy brains of human children, adolescents and adults with no known epilepsy, and (c) autopsy brains of humans with JME. FIG. 13 shows (a) RT-PCR analyses of mRNA from mouse whole brain tissue and hippocampal primary culture neurons. Upper panel; mouse Ethe1. Lower panel: g3pdh for control. (-): without template. (b) Northern-blot analyses of mouse Efhc1 on mouse whole bodies (embryonic days 7, 11, 15, 17), brains from embryonic days 17 and adult mice, and adult mouse multiple tissues. A segment of Efhc1 cDNA (nt. 1670-1990) was amplified by PCR, and used as a probe. Control signals for β-actin are shown in the lower panol. (c) Western blot analyses with anti-EFHC1 antibody Immuno-blots of lysates from HEK cells transiently transfected with expression contructs as indicated were analyzed. EGFP-tagged (~100 kDa) and Myc-tagged EFHC1 (~74 kDa) were detected at expected sizes by anti-EFHC1 antiserum. Anti-GFP antibody detected a band at ~100 kDa in the pEGFP-EFHC1 transfected cells and ~30 kDa in the pEGFP vector-transfected cells. Anti-Myc antibody detected a band at ~74 kDa in the pcDNA3-MycN-EFHC1 trnasfected cells. No signal appeared in lanes of untransfected cells. Histochemistry and electronmicoscopy will allow us to study how myoclonin distribution differs in these various brains on a tissue, cellular and subcellular level at different time periods.

For tissue in situ hybridization the protocol of Lyons, et al., 1994; 1995; 1990 is used to fix and embed mouse postnatal brains at various age intervals (birth, 1, 2, 3, 4, 6, 9, 12, 18 and 24 months). At each stage 5 mice will be studied, based on previous mouse studies in Lafora disease. For electron microscopic studies we follow procedures of cardiac perfusion, sectioning ultra-thin and immunostaining as published in Ganesh, et al., 2002.

Blood brain bather studies and electron-microscopic immunogold analyses of myoclonin immunoreactivity in brains of normal mice, normal humans and autopsy brains of humans with JME as well as studies on apoptotic and non-apoptotic pathways, including advanced glycation and lipoxidation end products will be performed. Anti-Myoclonin/EFHC1 antibody was generated by using a synthetic peptide corresponding to amino acid residue 522-533 (QYSPEALA-SIQN (SEQ ID NO: 20)) of human EFHC1 for immunization. The sequence is identical to that of mouse efhc1. Specificity and sensitivity of the antiserum were verified by probing the protein extracts of HEK cells transfected with GFP-tagged EFHC1 or myc-tagged EFHC1 expression constructs. The antibody detected expected bands with approximately 100 and 74 kDa for the GFP and myc-EFHC1 respectively and absorption with the peptide effectively eliminated the signals. No signal was observed in protein extracts from vector transfected and untransfected cells. This antibody successfully detected myoclonin/EFHC1 in immunohistological analyses.

Figure 14:
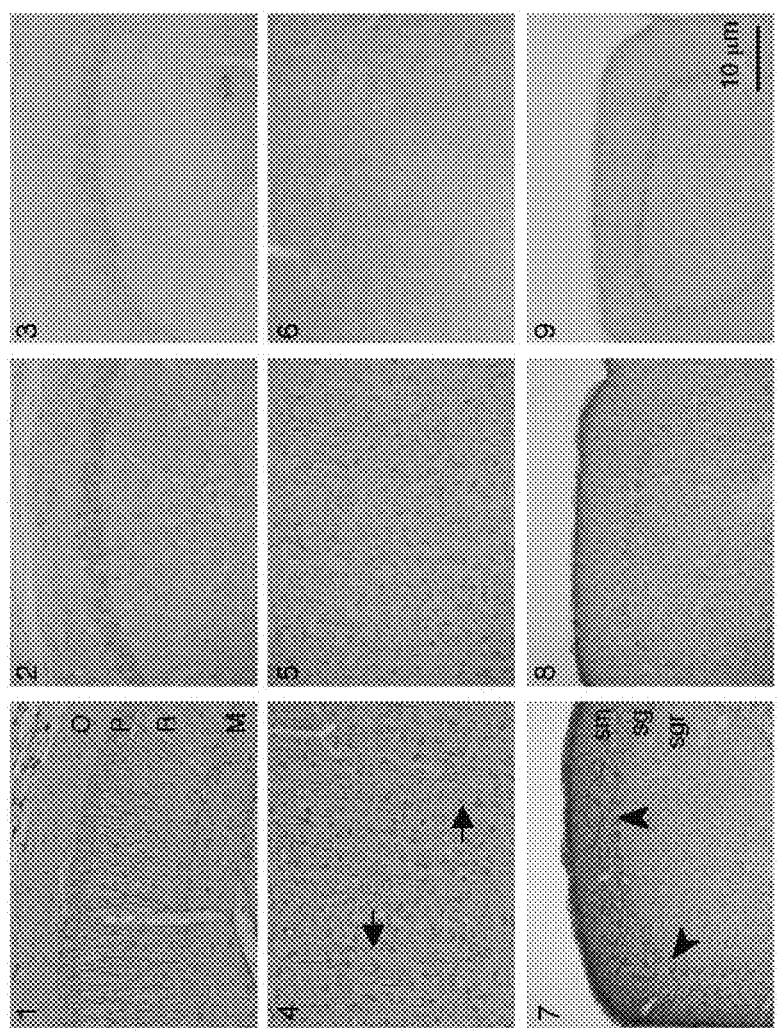
FIG. 14 shows immunohistochemical studies of mouse hippocampal CA1 region, layer III of cerebral cortex, and cerebellum.

Myoclonin/EFHC1 is widely distributed in CNS including hippocampus, cerebellum, cerebral cortex, thalamus, hypothalamus, amygdala and upper brainstem. FIG. 14 shows immunohistochemical studies of mouse hippocampal CA1 region (panels 1-3), layer III of cerebral cortex (panels 4-6), and cerebellum (panels 7-9). (1) anti-EFHC1 antibody shows signals on soma and dendrites of neurons. M:stratum moleculare, O:stratum oriens, P:stratum pyramidal, R:stratum radiatum. (4) Dendrites of neurons show signals (arrows). (7) Dendrites and soma of Purkinje cells (arrowheads) show signals. sg: stratum gangliosum, sgr: stratum granulosum, sm: stratum moleculare. (panels 2, 5 and 8) Staining with anti-EFHC1 antibody with EFHC1 peptide used for immunization. (panels 3, 6 and 9) Preimmune serum Immunoreactions of anti-EFHC1 with peptide and preimmune serum were not seen in all areas (panels 2, 3, 5, 6, 8 and 9). In mouse hippocampal primary culture neurons (6 d in vitro) from E16 mouse embryos were double-stained with antibodies to EFHC1 and to MPA2. Signals from EFHC1 and MAP 2 mostly overlap. Myoclonin overlaps with anti-R type VDCC antibody. See FIG. 4. See co-localization of antibodies against EFHC1 [FIG. 4A,C, F, I, L, O] and antibodies against R type VDCC [FIG. 4B,D, G, J, M, P] and merged images in FIG. 4E,H, K, N, Q), anti-MAP2 antibody (dendrite marker) and antisynaptophysin antibody (presynaptic vesicle marker) but not with anti-neurofilament (axon marker). Myoclonin/EFHC1 signals were dominantly observed in spines of dendrites. Immunostaining using antibodies against AGEP (advanced glycation end products) and ALEP (advanced lipoxidation end products) will be performed. Such studies have been done in studies of the laforin deficient mice and will lead to studies of the role of oxidative stress in cell death induced by myoclonin/EFHC1.

Example 11

EFHC1 Nucleotide and Amino Acid Sequences

FIG. 16 shows the deduced human cDNA sequence (FLJ22843; SEQ ID NO: 1); NCBI accession number NM_025184.

FIG. 17 shows the deduced human polypeptide sequence (FLJ22843; SEQ ID NO: 2); NCBI accession number NP_079460.

FIG. 18 shows a comparison of EFHC1 polypeptide sequence (NCBI accession number AK001328; NM_018100; SEQ ID NO: 4), with mouse polypeptide (NCBI accession number AK006489; SEQ ID NO: 5), and human polypeptide (FLJ22843; SEQ ID NO: 2).

FIG. 19 shows a comparison of human polypeptide (FLJ22843; SEQ ID NO: 2), with *Drosophila* polypeptide (NCBI accession number CG8959; SEQ ID NO: 6), and *Drosophila* polypeptide (NCBI accession number CG11048; SEQ ID NO: 7).

FIG. 20 shows the deduced human EFHC1 cDNA sequence (NCBI Accession: AK001328; NM_018100; SEQ ID NO: 3).

FIG. 21 shows the deduced human EFHC1 polypeptide sequence (NCBI Accession: AK001328; NM_018100; SEQ ID NO: 4).

FIG. 22 shows the deduced human EFHC1 cDNA sequence (NCBI Accession: AL122084; SEQ ID NO: 8) which is an alternatively spliced variant.

FIG. 23 shows the deduced human EFHC1 polypeptide, positions 243-278 of transcript B, c-terminus, (SEQ ID NO: 9) which is an alternatively spliced variant.

FIG. 25(*a*) shows the predicted amino acid sequence of the protein encoded by human EFHC1 gene transcript A. (SEQ ID NO: 4) Residues shown in bold face define the EF-hand motif (pfam 00036; E-value=0.00066). The deduced C terminus of transcript B (bottom; SEQ ID NO: 10) arises due to the retention of intron 4. N terminal region common to both proteins is underlined. See FIGS. 21 and 23. FIG. 25(*b*) shows amino acid sequence alignment of putative EFHC1 orthologs from mouse, pig, and cow. Note that four (D210N, R221H, F229L, D253Y) of the five missense mutations target residues that are conserved among the orthologs. Two (R182H, 1619L) of the three polymorphisms target residues that are also conserved among the orthologs.

Example 12

Diagnostic Assays to Predict Myoclonias, Grand Mal and Rare Absence Seizures in Juvenile Myoclonic Epilepsy (JME)

Assays to identify alleles and susceptibility loci for diagnosis of epilepsy are useful in the present invention. Juvenile myoclonal epilepsy (JME) accounts for at least 6 to 12 percent of all epilepsies. The full phenotype of JME consists of adolescent onset myoclonias, grand mal (clonic-tonic-clonic) convulsions, and absences associated with EEG diffuse polyspikes and slow waves. Diagnostic assays are useful to determine susceptibility to these epilepsy syndromes comprising various phenotypes.

Mutations in myoclonin1/EFHC1 can produce the full disease phenotype and are found in 20 percent of Spanish Amerinds with JME. Variants of myoclonin 1/EFHC1 are susceptibility factors in 38 percent of JME patients. Myoclonin 2/EFHC1a, a homologue of myoclonin 1, is located in chromosome Xp11.4, and is being analyzed for mutations and function. Myoclonin 1/EFHC1 and myoclonin 2/EFHC1a can serve as diagnostic markers for JME. One may expect that 6 or more, or 8 or more genes may be associated with the onset of epilepsy, for example, juvenile myoclonic epilepsy found in families in Belize, Los Angeles, Mexico, Brazil, Holland, and Japan. Segregation of EFHC1 mutations in epilepsy or polyspike wave-affected persons of JME families, together with reversal of the EFHC1-induced neuronal cell death and EFHC1-dependent increase of R-type $Ca^{2+}$ current by JME mutations, strongly support EFHC1 as the JME gene on chromosome 6p12, and EFHC1a on chromosome Xp11.4. Suzuki et al., *Epilepsy Res.* 50: 265-275, 2000. Most genes indicated as the cause of idiopathic generalized epilepsy encode ion channels. Identification of one or more, or multiple genes encoding a non-ion channel protein containing an EF-hand motif, modulating and interacting with R-type VDCC, and showing apoptotic activity, brings a new approach to the molecular pathology of idiopathic epilepsy.

A variety of diagnostic tests are used to detect polymorphism in EFHC1, EFHC1a, and other genes related to JME. Diagnostic assays include microcytotoxicity (Terasaki tray) assay, flow cytometric evaluation, EIA or ELISA assay for soluble myoclonin 1 or myoclonin 2 protein, isoelectric focusing and polymerase chain reaction with nucleotide sequencing of EFHC1 and EFHC1a genes.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

SEQUENCE LISTING

<160> NUMBER OF SEQ ID NOS: 48

<210> SEQ ID NO 1
<211> LENGTH: 2511
<212> TYPE: DNA
<213> ORGANISM: Homo sapiens

<400> SEQUENCE: 1

```
gggggccaaa caacacggcc gggaggcggc cgctgcctgc cgggccctct cttctgggac      60
cctggatttt cggacactga gcgccatggc cctgcctctg ctgccgggca acagcttcaa     120
ccgcaacgtg ggaaaggaga agtttcacaa atcccaacat tggggctttt gcaacaatgt     180
tatgatgttg gtgagtgatg aaaagcctgg aataggtgga gaaccacttc tggggcaaaa     240
gataaagcct aaatgtagca tatatcctaa aggagatgga agtgatgtac catcatgggt     300
agcctttgat aaacaggtat tatctttga tgcctatttg gaagaggaag tacttgataa     360
aagccaaacc aactacagaa taagatacta taaaatctac ttctaccctg aagatgacac     420
aattcaagta aatgaaccag aggtgaaaaa tagtggatta cttcaaggga cttctatccg     480
gcgtcatcgg attactcttc cgcctcctga tgaggatcag ttttatactg tgtatcattt     540
taatgtcggc acagaggttg tcttctatgg ccggacattc aagatttatg actgtgatgc     600
attcacaaga aacttttga ggaaaatagg ggtcaaagtg aatccccag tgcaatgtcc     660 agaagatcct tacatgaaga ttcggagaga ggttgtagaa cacgtagagc ccttacgtcc     720
```

```
ctacgaatcc ctcgacaccc tgaaacagtt cctccagtat catggcaaga ttttgtgttt      780
cttctgcctg tgggatgact cagtctcaat gtttggagac cgtagagaac tcatcctgca      840
ttacttcttg tgtgatgata ctattgaaat caaagaattg cttccacaca gctcaggccg      900
agatgctcta aaaatgttcc tccggaggag taagctaccc aagaattgcc cacctagagt      960
ctatcaacca ggccagataa cagatcgagc agttctcaat tcatatggtg actttataaa     1020
gaaccaagcg gatggctacc tgttcgatag atataagcta ggaaaagtag accaagagtt     1080
ttacaaagat agtgacctgt ccctaggagt caccatcaat gtgtgggaa gaaaagtgct      1140 cctttatgac tgtgatgaat ttacgaagtc ttattataag tctaaatatg gaattgagaa     1200
ctttacctca gtttcatgca agcctccttc tcctcctcca aaaatagaaa ggaaatttcc     1260
accttacaac ggttttggtt ctgaagagga ttctctccgt aactgcatag acctcaagcc     1320
cacacctcat cggaggaact tcaagaagtt tatggaaaaa gacagctatg ctccaaaag     1380 caatatactc cgttttttg caaaactagt cacagacaaa tgtgttgact ggacaggat      1440 gtttgttatt tcatattatc tcggtgatga caccatttca gtgtttgaac ctatagagag     1500
gaattcagga attgctggtg ggatgttctt gaaaagaagt cgcgttaaga agcctggaca     1560
agaagtcttt aaaagtgaac tatctgaata tatcaaggcc gaggagctgt acattggagt     1620
cacggtgaat gtgaatggtt acctatttcg tttgctcaat gctgatgagt ataccttaaa     1680
ctacatggag cagaatacag ataagtatcc tttcagtaac ctcaaacttg ccctacaaaa     1740
gctgaagcaa gaagaaggaa atccagaga gctcaagcag gtatttaaag ctgctgactc     1800
taagcacaca aatatggtgg attataatac attcagagac atattgatgt ctttgactgt     1860
tggaaacctt gcagagcaag aatttgtaac cattgcacgt cactaccgtg tgcctgaggg     1920
cacatgttca gatatggatt tcttaatcgc actggcccac gaaaagttca gaaaaatat      1980 gtttgagaat ttcgacactt tcatttattc ctgtgtgtat gaagatcgag aaaaaaaaaa     2040
tgtattaccc accaaagaca ttaaaaggct gtgcaaatcc tccagattac ctttgagtga     2100
tgatcttcta gaatccttat tgtcaaggtt tgaagacagt gaaaaacaaa tagattataa     2160 gtcattttc tctgccctga actggagaaa gaatccagtg cctgaattgc aaccagcatc     2220
ataccttaaa gagagatgtg aagatgtttg gcttggtatg ccatcaccta ttcctgcgaa     2280
atacattgac tactggaccct ttttgaagga cgcgtttggc ttagaggagg aataaccatg    2340
ccagttttgg tcaattctct atgatttact tctctcattt tgccacatt  actttagtag     2400 atataatttc attaaaaaca aaaagaaac aaggtttata ttaaatggaa atccataaac      2460
cacaaaaaaa aaaaaaaaaa aaaaaaaaaa aaaaaaaaaa aaaaaaaaa a               2511
```

<210> SEQ ID NO 2
<211> LENGTH: 749
<212> TYPE: PRT
<213> ORGANISM: Homo sapiens

<400> SEQUENCE: 2

Met Ala Leu Pro Leu Leu Pro Gly Asn Ser Phe Asn Arg Asn Val Gly
1               5                   10                  15

Lys Glu Lys Phe His Lys Ser Gln His Trp Gly Phe Cys Asn Asn Val
            20                  25                  30

Met Met Leu Val Ser Asp Glu Lys Pro Gly Ile Gly Gly Glu Pro Leu
        35                  40                  45

Leu Gly Gln Lys Ile Lys Pro Lys Cys Ser Ile Tyr Pro Lys Gly Asp

```
            50                  55                  60
Gly Ser Asp Val Pro Ser Trp Val Ala Phe Asp Lys Gln Val Leu Ser
 65                  70                  75                  80

Phe Asp Ala Tyr Leu Glu Glu Val Leu Asp Lys Ser Gln Thr Asn
                 85                  90                  95

Tyr Arg Ile Arg Tyr Tyr Lys Ile Tyr Phe Tyr Pro Glu Asp Asp Thr
                100                 105                 110

Ile Gln Val Asn Glu Pro Glu Val Lys Asn Ser Gly Leu Leu Gln Gly
                115                 120                 125

Thr Ser Ile Arg Arg His Arg Ile Thr Leu Pro Pro Pro Asp Glu Asp
            130                 135                 140

Gln Phe Tyr Thr Val Tyr His Phe Asn Val Gly Thr Glu Val Val Phe
145                 150                 155                 160

Tyr Gly Arg Thr Phe Lys Ile Tyr Asp Cys Asp Ala Phe Thr Arg Asn
                165                 170                 175

Phe Leu Arg Lys Ile Gly Val Lys Val Asn Pro Val Gln Cys Pro
                180                 185                 190

Glu Asp Pro Tyr Met Lys Ile Arg Arg Glu Val Val Glu His Val Glu
                195                 200                 205

Pro Leu Arg Pro Tyr Glu Ser Leu Asp Thr Leu Lys Gln Phe Leu Gln
                210                 215                 220

Tyr His Gly Lys Ile Leu Cys Phe Phe Cys Leu Trp Asp Asp Ser Val
225                 230                 235                 240

Ser Met Phe Gly Asp Arg Arg Glu Leu Ile Leu His Tyr Phe Leu Cys
                245                 250                 255

Asp Asp Thr Ile Glu Ile Lys Glu Leu Leu Pro His Ser Ser Gly Arg
                260                 265                 270

Asp Ala Leu Lys Met Phe Leu Arg Arg Ser Lys Leu Pro Lys Asn Cys
                275                 280                 285

Pro Pro Arg Val Tyr Gln Pro Gly Gln Ile Thr Asp Arg Ala Val Leu
                290                 295                 300

Asn Ser Tyr Gly Asp Phe Ile Lys Asn Gln Ala Asp Gly Tyr Leu Phe
305                 310                 315                 320

Asp Arg Tyr Lys Leu Gly Lys Val Asp Gln Glu Phe Tyr Lys Asp Ser
                325                 330                 335

Asp Leu Ser Leu Gly Val Thr Ile Asn Val Trp Gly Arg Lys Val Leu
                340                 345                 350

Leu Tyr Asp Cys Asp Glu Phe Thr Lys Ser Tyr Tyr Lys Ser Lys Tyr
                355                 360                 365

Gly Ile Glu Asn Phe Thr Ser Val Ser Cys Lys Pro Pro Ser Pro Pro
                370                 375                 380

Pro Lys Ile Glu Arg Lys Phe Pro Pro Tyr Asn Gly Phe Gly Ser Glu
385                 390                 395                 400

Glu Asp Ser Leu Arg Asn Cys Ile Asp Leu Lys Pro Thr Pro His Arg
                405                 410                 415

Arg Asn Phe Lys Lys Phe Met Glu Lys Asp Ser Tyr Gly Ser Lys Ser
                420                 425                 430

Asn Ile Leu Arg Phe Phe Ala Lys Leu Val Thr Asp Lys Cys Val Asp
                435                 440                 445

Leu Asp Arg Met Phe Val Ile Ser Tyr Tyr Leu Gly Asp Asp Thr Ile
                450                 455                 460

Ser Val Phe Glu Pro Ile Glu Arg Asn Ser Gly Ile Ala Gly Gly Met
465                 470                 475                 480
```

Phe Leu Lys Arg Ser Arg Val Lys Lys Pro Gly Gln Glu Val Phe Lys
            485                 490                 495

Ser Glu Leu Ser Glu Tyr Ile Lys Ala Glu Leu Tyr Ile Gly Val
        500                 505                 510

Thr Val Asn Val Asn Gly Tyr Leu Phe Arg Leu Leu Asn Ala Asp Glu
            515                 520                 525

Tyr Thr Leu Asn Tyr Met Glu Gln Asn Thr Asp Lys Tyr Pro Phe Ser
        530                 535                 540

Asn Leu Lys Leu Ala Leu Gln Lys Leu Lys Gln Glu Glu Gly Lys Ser
545                 550                 555                 560

Arg Glu Leu Lys Gln Val Phe Lys Ala Ala Asp Ser Lys His Thr Asn
                565                 570                 575

Met Val Asp Tyr Asn Thr Phe Arg Asp Ile Leu Met Ser Leu Thr Val
            580                 585                 590

Gly Asn Leu Ala Glu Gln Glu Phe Val Thr Ile Ala Arg His Tyr Arg
        595                 600                 605

Val Pro Glu Gly Thr Cys Ser Asp Met Asp Phe Leu Ile Ala Leu Ala
    610                 615                 620

His Glu Lys Phe Lys Lys Asn Met Phe Glu Asn Phe Asp Thr Phe Ile
625                 630                 635                 640

Tyr Ser Cys Val Tyr Glu Asp Arg Glu Lys Lys Asn Val Leu Pro Thr
                645                 650                 655

Lys Asp Ile Lys Arg Leu Cys Lys Ser Ser Arg Leu Pro Leu Ser Asp
            660                 665                 670

Asp Leu Leu Glu Ser Leu Leu Ser Arg Phe Glu Asp Ser Glu Lys Gln
        675                 680                 685

Ile Asp Tyr Lys Ser Phe Phe Ser Ala Leu Asn Trp Arg Lys Asn Pro
    690                 695                 700

Val Pro Glu Leu Gln Pro Ala Ser Tyr Leu Lys Glu Arg Cys Glu Asp
705                 710                 715                 720

Val Trp Leu Gly Met Pro Ser Pro Ile Pro Ala Lys Tyr Ile Asp Tyr
                725                 730                 735

Trp Thr Phe Leu Lys Asp Ala Phe Gly Leu Glu Glu Glu
            740                 745

<210> SEQ ID NO 3
<211> LENGTH: 2103
<212> TYPE: DNA
<213> ORGANISM: Homo sapiens

<400> SEQUENCE: 3
aaaaaccatg gatcctggag gtgcccgcga acactgcttg tcgcctgggc aaccggagag      60
gacgaagcag gacctaggtg gcggcggtgg taccggctgc aatggtgtcc aatcccgtgc     120
atggcttgcc ctttcttccg ggcacgtcct ttaaggactc tacgaaaaca gccttccaca     180
gaagtcagac gctgagctac aggaacggct atgcaattgt tcgacgtcca acagttggga     240
taggcggaga ccggctccag ttcaaccagc tgtcccaggc tgagctggat gagttggcca     300
gtaaggcacc agtcttaact tatggccaac taaacaagc cccacctgcg gattttattc     360
ctgcgcatgt ggcctttgac aaaaaggtac tgaaatttga tgcctatttc aagaagatg     420 ttcctatgtc aactgaggaa cagtatagga tccgtcaggt gaacatttac tattatctag     480
aagatgacag catgtctgtc atagagcctg ttgtagaaaa ttctggaatc cttcaaggca     540
agttaataaa acgccagcgg ctagccaaga atgaccgggg tgaccattac cattggaaag     600

```
acctaaatcg aggaataaac atcacaattt atggcaaaac tttccgcgtt gttgactgtg    660
accaattcac acaggtattt ttagaaagcc aaggaattga gttaaatcca ccagagaaga    720
tggctcttga tccttacact gaactccgaa acagcctct tcgtaagtat gtcaccccat     780
cagactttga tcaactcaag caatttctca cctttgacaa acaggtcctt cgattctatg    840
caatctggga tgatacagac agcatgtatg gtgaatgtcg gacctacatc attcattact    900
atcttatgga tgatacggtg gaaattcgag aggtccacga acggaatgat gggagagatc    960
ctttcccact cctaatgaac cgccagcgtg tgcccaaagt tttggtggaa aatgcaaaga   1020
acttccctca gtgtgtgcta gaaatctctg accaagaagt gttggaatgg tatactgcta   1080
aagacttcat tgttgggaag tcactcacta tccttgggag aactttcttc atttatgatt   1140
gtgatccatt tactcgacgg tattacaaag agaagtttgg aatcactgat ttaccacgta   1200
ttgatgtgag caagcgggaa ccacctccag taaaacagga gttgcctcct tataacggtt   1260
ttggactagt ggaagattct gctcagaatt gttttactct cattccaaaa gctccaaaaa   1320
aagacgttat taaaatgctg gtgaatgata acaaggtgct tcgttatttg gctgtactgg   1380
aatcccccat cccagaagac aaagaccgca gatttgtctt ctcttacttt ctagctaccg   1440
acatgatcag tatctttgag cctcctgttc gcaattctgg tatcattggg ggcaagtacc   1500
ttggcaggac taaagttgtt aaaccatact ctacagtgga caaccctgtc tactatggcc   1560
ccagtgactt cttcattggt gctgtgattg aagtgtttgg tcaccggttc atcatccttg   1620
atacagacga gtatgttttg aaatacatgg agagcaacgc tgcccagtat tcaccagaag   1680
cactcgcgtc aattcagaac catgtccgaa agcgagaagc gcctgctcca gaagcagaaa   1740
gcaagcaaac tgaaaaggat ccaggcgtgc aggaattgga agcattaata gacacaattc   1800
agaagcaact gaaagatcac tcatgcaaag acaacattcg tgaggcattt caaatttatg   1860
acaaggaagc ttcaggatat gtggacagag acatgttctt taaaatctgt gaatcgctta   1920
acgtcccagt ggatgactcc ttggttaagg agttaatcag gatgtgctct catggagaag   1980
gcaaaattaa ctactataac tttgttcgtg ctttctcaaa ctgacctgct gatgagaaaa   2040
tgcaagacaa ttttgatac tggaactatg ctttgaaata caccttacac tcttcatagt    2100
ggc                                                                 2103
```

<210> SEQ ID NO 4
<211> LENGTH: 640
<212> TYPE: PRT
<213> ORGANISM: Homo sapiens

<400> SEQUENCE: 4

```
Met Val Ser Asn Pro Val His Gly Leu Pro Phe Leu Pro Gly Thr Ser
1               5                   10                  15

Phe Lys Asp Ser Thr Lys Thr Ala Phe His Arg Ser Gln Thr Leu Ser
            20                  25                  30

Tyr Arg Asn Gly Tyr Ala Ile Val Arg Arg Pro Thr Val Gly Ile Gly
        35                  40                  45

Gly Asp Arg Leu Gln Phe Asn Gln Leu Ser Gln Ala Glu Leu Asp Glu
    50                  55                  60

Leu Ala Ser Lys Ala Pro Val Leu Thr Tyr Gly Gln Pro Lys Gln Ala
65                  70                  75                  80

Pro Pro Ala Asp Phe Ile Pro Ala His Val Ala Phe Asp Lys Lys Val
                85                  90                  95
```

```
Leu Lys Phe Asp Ala Tyr Phe Gln Glu Asp Val Pro Met Ser Thr Glu
             100                 105                 110

Glu Gln Tyr Arg Ile Arg Gln Val Asn Ile Tyr Tyr Leu Glu Asp
            115                 120                 125

Asp Ser Met Ser Val Ile Glu Pro Val Val Glu Asn Ser Gly Ile Leu
        130                 135                 140

Gln Gly Lys Leu Ile Lys Arg Gln Leu Ala Lys Asn Asp Arg Gly
145             150                 155                 160

Asp His Tyr His Trp Lys Asp Leu Asn Arg Gly Ile Asn Ile Thr Ile
                165                 170                 175

Tyr Gly Lys Thr Phe Arg Val Val Asp Cys Asp Gln Phe Thr Gln Val
            180                 185                 190

Phe Leu Glu Ser Gln Gly Ile Glu Leu Asn Pro Pro Glu Lys Met Ala
        195                 200                 205

Leu Asp Pro Tyr Thr Glu Leu Arg Lys Gln Pro Leu Arg Lys Tyr Val
    210                 215                 220

Thr Pro Ser Asp Phe Asp Gln Leu Lys Gln Phe Leu Thr Phe Asp Lys
225                 230                 235                 240

Gln Val Leu Arg Phe Tyr Ala Ile Trp Asp Asp Thr Asp Ser Met Tyr
                245                 250                 255

Gly Glu Cys Arg Thr Tyr Ile Ile His Tyr Tyr Leu Met Asp Asp Thr
            260                 265                 270

Val Glu Ile Arg Glu Val His Glu Arg Asn Asp Gly Arg Asp Pro Phe
        275                 280                 285

Pro Leu Leu Met Asn Arg Gln Arg Val Pro Lys Val Leu Val Glu Asn
    290                 295                 300

Ala Lys Asn Phe Pro Gln Cys Val Leu Glu Ile Ser Asp Gln Glu Val
305                 310                 315                 320

Leu Glu Trp Tyr Thr Ala Lys Asp Phe Ile Val Gly Lys Ser Leu Thr
                325                 330                 335

Ile Leu Gly Arg Thr Phe Phe Ile Tyr Asp Cys Asp Pro Phe Thr Arg
            340                 345                 350

Arg Tyr Tyr Lys Glu Lys Phe Gly Ile Thr Asp Leu Pro Arg Ile Asp
        355                 360                 365

Val Ser Lys Arg Glu Pro Pro Val Lys Gln Glu Leu Pro Pro Tyr
    370                 375                 380

Asn Gly Phe Gly Leu Val Glu Asp Ser Ala Gln Asn Cys Phe Thr Leu
385                 390                 395                 400

Ile Pro Lys Ala Pro Lys Lys Asp Val Ile Lys Met Leu Val Asn Asp
                405                 410                 415

Asn Lys Val Leu Arg Tyr Leu Ala Val Leu Glu Ser Pro Ile Pro Glu
            420                 425                 430

Asp Lys Asp Arg Arg Phe Val Phe Ser Tyr Phe Leu Ala Thr Asp Met
        435                 440                 445

Ile Ser Ile Phe Glu Pro Pro Val Arg Asn Ser Gly Ile Ile Gly Gly
    450                 455                 460

Lys Tyr Leu Gly Arg Thr Lys Val Val Lys Pro Tyr Ser Thr Val Asp
465                 470                 475                 480

Asn Pro Val Tyr Tyr Gly Pro Ser Asp Phe Phe Ile Gly Ala Val Ile
                485                 490                 495

Glu Val Phe Gly His Arg Phe Ile Ile Leu Asp Thr Asp Glu Tyr Val
        500                 505                 510

Leu Lys Tyr Met Glu Ser Asn Ala Ala Gln Tyr Ser Pro Glu Ala Leu
```

```
            515                 520                 525
Ala Ser Ile Gln Asn His Val Arg Lys Arg Glu Ala Pro Ala Pro Glu
530                 535                 540

Ala Glu Ser Lys Gln Thr Glu Lys Asp Pro Gly Val Gln Glu Leu Glu
545                 550                 555                 560

Ala Leu Ile Asp Thr Ile Gln Lys Gln Leu Lys Asp His Ser Cys Lys
                565                 570                 575

Asp Asn Ile Arg Glu Ala Phe Gln Ile Tyr Asp Lys Glu Ala Ser Gly
                580                 585                 590

Tyr Val Asp Arg Asp Met Phe Phe Lys Ile Cys Glu Ser Leu Asn Val
                595                 600                 605

Pro Val Asp Asp Ser Leu Val Lys Glu Leu Ile Arg Met Cys Ser His
                610                 615                 620

Gly Glu Gly Lys Ile Asn Tyr Tyr Asn Phe Val Arg Ala Phe Ser Asn
625                 630                 635                 640

<210> SEQ ID NO 5
<211> LENGTH: 648
<212> TYPE: PRT
<213> ORGANISM: Mus musculus

<400> SEQUENCE: 5

Met Gly Thr Asn Pro Val His Gly Leu Pro Phe Leu Pro Gly Ser Ser
1               5                   10                  15

Phe Thr Asp Ser Thr Lys Thr Ala Phe His Arg Ser Gln Thr Leu Asn
                20                  25                  30

Tyr Arg Asn Gly Tyr Ala Val Val Arg Arg Pro Thr Met Gly Ile Gly
            35                  40                  45

Gly Asp Arg Leu His Tyr Asn Gln Leu Ser Gln Ala Glu Leu Asp Glu
        50                  55                  60

Leu Ala Asn Lys Ala Pro Ile Leu Thr Tyr Gly Pro Leu Lys Gln Ala
65                  70                  75                  80

Pro Leu Ala Glu Phe Val Pro Ala His Val Ala Phe Asp Lys Lys Val
                85                  90                  95

Leu Lys Phe Ser Ala Tyr Phe Gln Glu Asp Val Pro Ile Ser Met Glu
                100                 105                 110

Glu His Tyr Arg Ile Arg His Val Asn Ile Tyr Tyr Tyr Leu Glu Asp
            115                 120                 125

Asp Ser Met Ser Val Ile Glu Pro Val Val Glu Asn Ser Gly Ile Pro
        130                 135                 140

Gln Gly Lys Leu Ile Lys Arg Gln Arg Phe Thr Lys Asn Asp Met Gly
145                 150                 155                 160

Asp His Tyr His Trp Lys Asp Leu Asn Arg Gly Ile Asn Leu Thr Val
                165                 170                 175

Tyr Gly Lys Thr Phe Arg Ile Val Asp Cys Asp Arg Phe Thr Gln Asp
                180                 185                 190

Phe Leu Glu Ser Gln Gly Ile Glu Leu Asn Pro Ser Glu Lys Ile Pro
            195                 200                 205

Leu Asp Pro Tyr Thr Gln Leu Arg Lys Glu Pro Val Arg Lys Tyr Val
        210                 215                 220

Thr Pro Ser Asp Phe Asp Gln Leu Lys Gln Phe Leu Thr Phe Asp Lys
225                 230                 235                 240

Gln Val Leu Arg Phe Tyr Ala Ile Trp Asp Asp Thr Asp Ser Leu Phe
                245                 250                 255
```

Gly Glu Cys Arg His Tyr Ile Ile His Tyr Tyr Leu Met Asp Asp Thr
              260                 265                 270

Val Glu Ile Arg Glu Val His Glu Arg Asn Asn Gly Arg Asp Pro Phe
        275                 280                 285

Pro Leu Leu Met Asn Arg Gln Arg Met Pro Lys Val Leu Val Glu Asn
    290                 295                 300

Ala Lys Asn Phe Pro Lys Cys Val Leu Glu Ile Ser Asp Gln Glu Val
305                 310                 315                 320

Leu Glu Trp Tyr Thr Ala Lys Asp Phe Ile Val Gly Lys Pro Leu Thr
                325                 330                 335

Ile Leu Gly Arg Thr Phe Phe Ile Tyr Asp Cys Asp Pro Phe Thr Arg
                340                 345                 350

Gln Phe Tyr Lys Asp Lys Phe Gly Met Pro Asp Leu Pro Pro Val Asp
            355                 360                 365

Val Thr Lys Lys Glu Pro Pro Val Lys Gln Glu Leu Pro Pro Tyr
        370                 375                 380

Asn Gly Tyr Gly Leu Ile Glu Asp Ser Ala Gln Asn Cys Phe Ala Leu
385                 390                 395                 400

Ile Pro Lys Ala Pro Arg Lys Asp Val Val Lys Met Leu Met Asn Asp
                405                 410                 415

Asn Lys Val Leu Arg Tyr Leu Ala Ala Leu Glu Ser Pro Ile Pro Glu
                420                 425                 430

Asp Lys Asp Arg Arg Phe Val Phe Ser Tyr Phe Leu Ala Thr Asp Met
            435                 440                 445

Ile Ser Ile Phe Glu Pro Pro Val Arg Asn Ser Gly Ile Ile Gly Gly
450                 455                 460

Lys Phe Leu Gly Arg Thr Lys Val Val Lys Ser Phe Ser Pro Val Asp
465                 470                 475                 480

Asn Pro Ile Tyr Tyr Ser Pro Ser Asp Phe Phe Ile Gly Ala Val Ile
                485                 490                 495

Glu Val Phe Gly His Arg Phe Val Ile Leu Asp Thr Asp Glu Tyr Val
                500                 505                 510

Leu Lys Tyr Met Glu Ser Asn Ala Ser Gln Tyr Ser Pro Glu Ala Leu
            515                 520                 525

Ala Ser Ile Gln Asn Arg Ile Gln Lys Pro Glu Leu Pro Ala Pro Glu
530                 535                 540

Leu Glu Ser Lys Gln Ala Thr Gly Glu Pro Met Val Gln Gly Thr Glu
545                 550                 555                 560

Glu Ser Lys Val Gln Asp Leu Asp Ala Leu Ile Asp Gln Ile His Met
                565                 570                 575

His Leu Lys Tyr Asn Ser Tyr Lys Glu Asn Leu Arg Glu Thr Phe Gln
            580                 585                 590

Met Tyr Asp Lys Asp Glu Ser Gly Tyr Val Asp Arg Glu Thr Phe Phe
        595                 600                 605

Lys Ile Cys Glu Thr Leu Asn Val Pro Val Asp Asp Ser Leu Ile Lys
    610                 615                 620

Glu Leu Ile Arg Leu Cys Thr His Gly Glu Gly Arg Ile Asn Tyr Tyr
625                 630                 635                 640

Asn Phe Val Arg Ala Phe Ser Asn
                645

<210> SEQ ID NO 6
<211> LENGTH: 793
<212> TYPE: PRT

<213> ORGANISM: Drosophila melanogaster

<400> SEQUENCE: 6

```
Met Leu Arg Ile Pro Gly Met Pro Leu Leu Pro Gly Thr Leu Phe Arg
1               5                   10                  15

Asp Val Ser Lys Gly His Tyr Pro Lys Pro Gln Ser Leu Ala Asn Val
            20                  25                  30

Gln Gly Leu Ser Met Leu Ser Asp Arg Gln Pro Ala Pro Val Glu
        35                  40                  45

Ser Gly Ser Val Thr Val Asp Ile Ser Cys Pro Pro Val Gly Ala Ser
    50                  55                  60

Ser Ile Tyr Pro Pro Arg Ser Gly Pro Arg Met Pro Pro Trp Leu Ala
65                  70                  75                  80

Tyr Asp Lys Lys Val Leu Cys Phe His Ala Tyr Phe Lys Gln Thr Leu
                85                  90                  95

Gln Glu Val Tyr His Ala Pro Tyr Leu Val Arg Lys Val Lys Ile Tyr
            100                 105                 110

Tyr Tyr Leu Glu Asp Gly Thr Leu Glu Ile Tyr Glu Pro Arg Val Asp
        115                 120                 125

Asn Ser Gly Ile Val Gln Gly Cys Val Val His Arg Gln Arg Val Gln
130                 135                 140

Lys Ala Pro Pro Cys Asp Asn Glu Phe Met Ser Leu Ile Asp Leu Asn
145                 150                 155                 160

Val Asp Gln Thr Val Gln Ile Phe Asp Arg Gln Tyr His Ile Thr Asp
                165                 170                 175

Cys Asp Pro Phe Thr Arg Thr Phe Leu Asn Lys Arg Gly Ile Thr Val
            180                 185                 190

Pro Asp Pro Val Lys Ser Pro Cys Asp Pro Thr Glu Glu Gln Arg Lys
        195                 200                 205

Arg Glu Asn Gln Pro Arg Ser Gly Asn Leu Ile Pro Lys Asn His Pro
210                 215                 220

Phe Ala Gln Phe Leu Lys Tyr Asp Arg Gln Ile Leu Lys Phe Gln Ala
225                 230                 235                 240

Tyr Trp Asp Asp Arg Thr Glu Phe Gly Asp Val Arg Lys Leu Glu Leu
                245                 250                 255

Cys Tyr Tyr Leu Ser Asp Asp Thr Ile Glu Ile Lys Glu Gln His Ile
            260                 265                 270

Arg Asn Ser Gly Arg Asp Gly Pro Thr Val Phe Leu Lys Arg Gly Arg
        275                 280                 285

Leu Ala Arg Glu Phe Glu Gly Leu Gln Leu Pro Gly Gln Met Thr Pro
290                 295                 300

Met Thr Leu Leu Asn Val Leu Gly Thr Asn Met Arg Asn Val Arg Tyr
305                 310                 315                 320

Cys Val Asp Pro Leu Asn Thr Gly Asn Lys Glu Ile His Tyr Tyr Arg
                325                 330                 335

Glu Lys Asp Leu Gln Ile Gly Ser Val Ile Asn Val Tyr Gly Arg Ala
            340                 345                 350

Val Val Ile Thr Glu Leu Asp Pro Phe Thr Gln Asn Tyr Tyr Arg Gln
        355                 360                 365

Arg Tyr Gly Ile Gln Asp Phe Thr Pro Leu Pro Ile Pro Ala Arg Ser
370                 375                 380

Asp Asp Cys Ala Asp His Arg Ser Glu Arg Gln Leu Pro Pro Tyr Asn
385                 390                 395                 400
```

Gly Trp Gly Ser Tyr Glu Asp Ser Val Gly Asn Cys Ile Ser Val Glu
                    405                 410                 415

Pro Lys Pro Lys Ser Asp Phe Lys Lys Phe Ile Lys Tyr Asp Arg
        420                 425                 430

Tyr Val Leu Arg Phe Gly Ala Lys Met Leu Ser Thr Ile Lys Ala Asn
            435                 440                 445

Cys Glu Arg Ile Phe Val Ile Ser Tyr Tyr Leu Cys Asp Asp Thr Leu
    450                 455                 460

Gln Ile Gln Glu Ile Ala Val Arg Asn Ser Gly Phe Leu Gly Gly Glu
465                 470                 475                 480

Phe Met Lys Arg Thr Arg Leu Glu Leu Pro Gly Gln Glu Arg Phe Ser
                485                 490                 495

Cys Lys Gln Pro Gln Tyr Tyr Met Pro Trp Asn Phe Val Gly Ser
        500                 505                 510

Thr Met Ser Leu Lys Asp Phe Ile Phe His Ile Val Ser Ala Asp Glu
            515                 520                 525

Tyr Thr Leu Met Tyr Met Glu His His Pro Glu Ile Phe Pro His Ala
        530                 535                 540

Asn Val Gly Val Ile Met Glu Lys Val Lys Ser Ala Leu Gln Asn Arg
545                 550                 555                 560

Met Ala Glu Phe Val Gly Ser Cys Val Pro Asp Cys Thr Asp Leu Glu
                565                 570                 575

Lys Lys Arg Asp Val Phe Val Ser Phe Glu Ser Phe Lys Gly Ala Leu
                580                 585                 590

Ile Ser Ile Met Gly Asn Gln Ile Ser Asp His Glu Ile Ile Ser Leu
            595                 600                 605

Cys Arg His Phe Ser Ala Glu Lys Ser Gln Pro Asn Ala Cys Asp Arg
    610                 615                 620

Ser Thr Val Arg Ala Ala His Leu Glu Leu Lys Arg Thr Leu Trp
625                 630                 635                 640

Asn Ala Arg Asp Asp Leu Met Glu His Phe His His Ile Asn Pro Thr
                645                 650                 655

Asn Gln Pro Phe Leu Pro Glu Val Lys Val Arg Ser Ala Leu Arg Gly
            660                 665                 670

Cys Arg Leu Pro Phe Ser Leu Glu Leu Ile Asp Asn Ile Leu Ser Ile
        675                 680                 685

Leu Asn Arg Asn Glu Cys Asp Asp Ile Glu Val Cys Asp Leu Met Asn
    690                 695                 700

Phe Ile Asp Val Ser Cys Gly Lys Gly Cys Asp Met Leu Pro Val Asn
705                 710                 715                 720

His Ala Phe Glu Leu Cys Pro Lys Ile Pro Phe Leu Asn Lys Gly Arg
                725                 730                 735

Val Val Asn Phe Thr Cys Phe Leu Arg Glu Leu Asn Leu Pro Leu Asn
            740                 745                 750

Leu Pro Ala Gly Gly Glu Lys Asn Asn Asp Ala Ile Ala Glu Gly Gly
        755                 760                 765

Arg Ile Met Pro Pro Ser Ala Met Pro Asp Thr Asp Ala His Lys Ala
    770                 775                 780

Asn Glu Asp Asp Ala Gln His Met Ala
785                 790

<210> SEQ ID NO 7
<211> LENGTH: 765
<212> TYPE: PRT

<213> ORGANISM: Drosophila melanogaster

<400> SEQUENCE: 7

```
Met Met Arg Leu Pro Gly Met Pro Met Leu Pro Gly Ala Gln Phe Tyr
1               5                   10                  15
Asp Arg Gly Lys Arg Arg His Pro Arg Gln Gln Thr Leu Met His Tyr
            20                  25                  30
Gln Gly Ile Gln Met Leu Ser Asp Arg Arg Glu Pro Glu Leu Val Glu
        35                  40                  45
Pro Asn Gly Ile Val Ala Asp Pro Lys Cys Pro Pro Val Pro Ala Gln
50                  55                  60
Leu Asn Ser Leu Trp Ala Pro Lys Ala Thr Thr Lys Leu Pro Pro Trp
65                  70                  75                  80
Leu Ala Tyr Asp Lys Gln Val Leu Cys Phe Asn Ala Tyr Phe Lys Glu
                85                  90                  95
Asn Leu Thr Glu Ile Tyr His Ala Pro Tyr Gln Val Arg Lys Val Lys
            100                 105                 110
Ile Phe Phe Tyr Leu Glu Asp Gly Thr Met Gln Val Thr Glu Pro Lys
        115                 120                 125
Val Glu Asn Ser Gly Ile Pro Gln Gly Cys Leu Val His Arg Gln Arg
130                 135                 140
Ile Pro Lys Ala Pro Pro Thr Asp Arg Glu Phe Ile Ser Ile Phe Asp
145                 150                 155                 160
Leu Asn Val Asp Thr Asp Val Gln Ile Phe Asp Arg Val Tyr His Ile
                165                 170                 175
Ser Gly Cys Asp Val Phe Thr Arg Gln Phe Leu Asn Arg Ala Gly Ile
            180                 185                 190
Phe Val Pro Glu Ala Gln Gln Glu Pro Cys Asp Pro Thr Thr Glu Ile
        195                 200                 205
Arg Lys Arg Ser Gly Leu Lys Gln Thr Gly Asn Thr Ala Thr Ser Ala
210                 215                 220
Leu Pro Lys Lys His Ala Phe Ala Gln Phe Leu Glu Phe Asp Arg Arg
225                 230                 235                 240
Val Leu Lys Phe Gln Gly Tyr Trp Asn Asp Arg Ser Glu Phe Gly Asp
                245                 250                 255
Val Arg Lys Leu Glu Val Cys Tyr Tyr Leu Ala Asp Asp Thr Ile Asp
            260                 265                 270
Ile Lys Glu Lys Phe Pro Arg Asn Ser Gly Arg Glu Gly Pro Thr Thr
        275                 280                 285
Phe Leu Lys Arg Gly Lys Leu Pro Lys Glu Phe Ser Gly Leu Pro Leu
290                 295                 300
Pro Gly Gln Gln Thr Ala Met Thr Leu Leu Asn Val Leu Gly Asn Ser
305                 310                 315                 320
Met Arg Asp Val Arg Tyr Val Ala Asp Pro Leu Asn Thr Gly Gln Lys
                325                 330                 335
Glu Val Gln His Tyr Thr Asp Gln Asp Leu Gln Ile Gly Ala Val Leu
            340                 345                 350
Asn Val Phe Gly Arg Ser Val Val Leu Thr Ser Cys Asp Gln Phe Thr
        355                 360                 365
Gln Ser Tyr Tyr Arg Glu Lys Tyr Gly Ile Gln Glu Phe Ser Pro Gln
370                 375                 380
Pro Ile Pro Glu Arg Ser Asp Ile Arg Pro Tyr Thr Gln Gly Gly Met
385                 390                 395                 400
```

-continued

```
Gly Ser Arg Arg Leu Pro Pro Tyr Asn Gly Trp Gly Ser His Glu Asp
            405                 410                 415
Ser Glu Gly Asn Cys Ile Thr Val Glu Pro Lys Pro Gln Ala Asp
        420                 425                 430
Phe Lys Lys Leu Phe Lys Tyr Asp Gly Cys Ile Leu Arg Phe Gly Ala
            435                 440                 445
Lys Leu Ile Ser Ala Ile Arg Asp Asn Gly Glu Arg Asp Phe Val Ile
450                 455                 460
Ser Tyr Phe Leu Ala Asp Asp Thr Leu Gln Ile Tyr Glu Thr Ser Arg
465                 470                 475                 480
Arg Asn Ser Gly Phe Leu Gly Gly Glu Phe Leu Lys Arg Ala Arg Val
                485                 490                 495
Pro Leu Pro Gly Gln Asp Met Tyr Ser Ser Arg Pro Glu Tyr Tyr
            500                 505                 510
Arg Ala Asn Asp Phe Tyr Ile Gly Arg Thr Met Thr Leu Lys Asp His
            515                 520                 525
Ile Phe His Ile Val Ser Ala Asp Glu Phe Thr Leu Met Tyr Met Glu
            530                 535                 540
Gln His Pro Ser Glu Phe Pro Val Ala Asp Ile Gln Lys Ile Met Gln
545                 550                 555                 560
Lys Ile Arg Glu Ala Val Arg Pro Asp Tyr Lys Gln Phe Val Leu Arg
                565                 570                 575
Cys Lys Pro Asp Gly Asp Leu Gly Asp Tyr Thr Ala Val Ser Phe Glu
            580                 585                 590
Thr Leu Arg Ser Thr Leu Leu Ser Tyr Leu Ser Lys Asp Cys Leu Leu
            595                 600                 605
Asn His Glu Ile Val Thr Val Cys Arg Phe Phe Ser Ala Glu Gln Ala
            610                 615                 620
Met Pro Pro Ser Cys Asp Arg Asn Arg Val Arg Ala Ala Gln Leu
625                 630                 635                 640
Glu Leu Lys Arg Ala Leu Trp Asn Gly Met Asp Gln Leu Asn Asp His
                645                 650                 655
Leu Ser His Ile Asn Pro Ala Cys Lys Pro Tyr Ile Ser Glu Gly Gln
            660                 665                 670
Val Arg Ser Thr Leu Arg Gly Cys Arg Leu Pro Phe Ser Leu Glu Leu
            675                 680                 685
Val Glu Asp Ile Leu Met Val Leu Gln Arg Asn Gly Gln Asn Glu Ile
690                 695                 700
Glu Val Arg Asp Phe Leu Ala Phe Phe Asn Met Arg Asn Asp Gln Val
705                 710                 715                 720
Pro Asp Ile Ala Pro Leu Asn Ile Ala Phe Glu Leu Cys Pro Lys Leu
                725                 730                 735
Pro Phe Leu His Lys Gly Arg Leu Val Asp Phe Thr Trp Phe Leu Asp
            740                 745                 750
Tyr Leu Gly Ile Glu Glu Leu Lys Arg Ala Asn Asn
            755                 760                 765

<210> SEQ ID NO 8
<211> LENGTH: 3447
<212> TYPE: DNA
<213> ORGANISM: Homo sapiens

<400> SEQUENCE: 8
agcgttacca tgatcctgga ggtgcccgcg aacactgctt gtcgcctggg caaccggaga    60
```

```
ggacgaagca ggacctaggt ggcggcggtg gtaccggctg caatggtgtc caatcccgtg      120
catggcttgc cctttcttcc gggcacgtcc tttaaggact ctacgaaaac agccttccac      180
agaagtcaga cgctgagcta caggaacggc tatgcaattg ttcgacgtcc aacagttggg      240
ataggcggag accggctcca gttcaaccag ctgtcccagg ctgagctgga tgagttggcc      300
agtaaggcac cagtcttaac ttatggccaa cctaaacaag ccccacctgc ggattttatt      360
cctgcgcatg tggcctttga caaaaaggta ctgaaatttg atgcctattt ccaagaagat      420
gttcctatgt caactgagga acagtatagg atccgtcagg tgaacattta ctattatcta      480
gaagatgaca gcatgtctgt catagagcct gttgtagaaa attctggaat ccttcaaggc      540
aagttaataa aacgccagcg gctagccaag aatgaccggg gtgaccatta ccattggaaa      600
gacctaaatc gaggaataaa catcacaatt tatggcaaaa cttccgcgt tgttgactgt       660 gaccaattca cacaggtatt tttagaaagc caaggaattg agttaaatcc accagagaag      720
atggctcttg atccttacac tgaactccga aaacagcctc ttcgtaagta tgtcaccccca     780 tcagactttg atcaactcaa gcaatttctc acctttgaca aacaggtaag tgacatagga      840
accacaatag gcttacttat ttccaaatgt gacctacatt tattggcaaa aggtttgggt      900
agctgtattg gtaactattt tgaaacatta cagctataat tgaactgttt ggacacagta      960
ctgtctttct gctttcatca agggttacag gtacaggaat gcctacattt catatggaga     1020
tccaaagaag atcgtggagt tgcggagttg ttttgtgaac ctcaccaaac atttaaatct     1080
caaagcaatt cctgagctac atctgcttcc caccttacgt ttccaattga caatttcttt     1140
cccttaaaat gagctaattt catagactcc tttgtgaaac cataaatcga ttattaggaa     1200
atttcacaaa tatgcataca tgtaggttgt aatgttaaaa tgtttaattt cacagaagcc     1260
ccactacaga tgcttccttg ttaaatgtta tattaatatt ggagtccaga atgttctgag     1320
cattttccaa ctctgttcca accttcctaa tcctctccct tgtgagctga tgtgtataag     1380
cagatttaaa tccttccctt tctgtactaa agggagaaaa aaaaggaaga gatcaccctc     1440
agtgcttctt tgctgctcct tttctttaga catttaaccc cttttagttc agaaaatgta     1500
aactagcact agcatggtct tttaaggatt ttgttcatat cagtcatata tctgttatta     1560
ttatgtattt aaagattgtg tttattccca cgatttgaag aagcctagcc aaaaaaaaaa     1620
aaaaaaagat tgtgtttata ttattgctag aagatatgtg ttgatgggac caaaaaaaga     1680
ctggttaata aataaaaatt ttttctacac taattatata taaaccatat tcacatgtac     1740
ctttattaat atatatatac cactatgtaa agaacttcat tgctcttta atttagcttc      1800 tctttcactg actaatattt tggatcaaag tgagctcttc ttttttggca caaacttata     1860
atcctattat ttaattcttt ccagctgctg acatatagta cataatttca gatgttttag     1920
tatgtttgat gaatatttct ttttttttcaa tttaccccat ctgaaattac ttcatagtct    1980
ttccagctag tctttccatc gttgatacat aattgccaaa gtagccaagt tgaactccct     2040
acttttagga ttcttgagtc actactttgg attcttcaaa ggtccttcga ttctatgcaa     2100
tctgggatga tacagacagc atgtatggtg aatgtcggac ctacatcatt cattactatc     2160
ttatggatga tacggtggaa attcgagagg tccacgaacg gaatgatggg agagatcctt     2220
tcccactcct aatgaaccgc cagcgtgtgc ccaaagtttt ggtggaaaat gcaagaact     2280 tccctcagtg tgtgctagaa atctctgacc aagaagtgtt ggaatggtat actgctaaag     2340
acttcattgt tgggaagtca ctcactatcc ttggagaac tttcttcatt tatgattgtg     2400
atccatttac tcgacggtat tacaaagaga agtttggaat cactgattta ccacgtattg     2460
```

```
atgtgagcaa gcgggaacca cctccagtaa aacaggagtt gcctccttat aacggttttg    2520
gactagtgga agattctgct cagaattgtt ttgctctcat tccaaaagct ccaaaaaaag    2580
acgttattaa aatgctggtg aatgataaca aggtgcttcg ttatttggct gtactggaat    2640
cccccatccc agaagacaaa gaccgcagat ttgtcttctc ttactttcta gctaccgaca    2700
tgatcagtat ctttgagcct cctgttcgca attctggtat cattgggggc aagtaccttg    2760
gcaggactaa agttgttaaa ccatactcta cagtggacaa ccctgtctac tatgccccca    2820
gtgacttctt cattggtgct gtgattgaag tgtttggtca ccggttcatc atccttgata    2880
cagacgagta tgttttgaaa tacatggaga gcaacgctgc ccagtattca ccagaagcac    2940
tcgcgtcaat tcagaaccat gtccgaaagc gagaagcgcc tgctccagaa gcagaaagca    3000
agcaaactga aaaggatcca ggcgtgcagg aattggaagc attaatagac acaattcaga    3060
agcaactgaa agatcactca tgcaaagaca acattcgtga ggcatttcaa atttatgaca    3120
aggaagcttc aggatatgtg gacagagaca tgttctttaa aatctgtgaa tcgcttaacg    3180
tcccagtgga tgactccttg gttaaggagt tactcaggat gtgctctcat ggagaaggca    3240
aaattaacta ctataacttt gttcgtgctt tctcaaactg acctgctgat gagaaaatgc    3300
aagacaattt ttgatactgg aactatgctt tgaaatacac cttacactct tcatagaggc    3360
atttacaggg ttcctgaagt ttttatttctg ttttggttct tatttcactc ctactgaagt    3420
cgaaactaaa ttggatcaaa aaaaaaa                                       3447
```

```
<210> SEQ ID NO 9
<211> LENGTH: 35
<212> TYPE: PRT
<213> ORGANISM: Homo sapiens

<400> SEQUENCE: 9

Ser Asp Ile Gly Thr Thr Ile Gly Leu Leu Ile Ser Lys Cys Asp Leu
1               5                   10                  15

His Leu Leu Ala Lys Gly Leu Gly Ser Cys Ile Gly Asn Tyr Phe Glu
            20                  25                  30

Thr Leu Gln
        35

<210> SEQ ID NO 10
<211> LENGTH: 36
<212> TYPE: PRT
<213> ORGANISM: Homo sapiens

<400> SEQUENCE: 10

Ser Asp Ile Gly Thr Thr Ile Gly Leu Leu Ile Ser Lys Cys Asp Leu
1               5                   10                  15

His Leu Leu Ala Lys Gly Leu Gly Ser Cys Ile Gly Asn Tyr Phe Glu
            20                  25                  30

Thr Leu Gln Leu
        35

<210> SEQ ID NO 11
<211> LENGTH: 7
<212> TYPE: PRT
<213> ORGANISM: Homo sapiens

<400> SEQUENCE: 11

Tyr Gly Gln Pro Lys Gln Ala
1               5
```

```
<210> SEQ ID NO 12
<211> LENGTH: 7
<212> TYPE: PRT
<213> ORGANISM: Mus musculus

<400> SEQUENCE: 12

Tyr Gly Pro Leu Lys Gln Ala
1               5

<210> SEQ ID NO 13
<211> LENGTH: 7
<212> TYPE: PRT
<213> ORGANISM: Sus sp.

<400> SEQUENCE: 13

Met Ala Leu Asp Pro Tyr Thr
1               5

<210> SEQ ID NO 14
<211> LENGTH: 7
<212> TYPE: PRT
<213> ORGANISM: Bos sp.

<400> SEQUENCE: 14

Tyr Gly Gln Ala Arg Gln Ala
1               5

<210> SEQ ID NO 15
<211> LENGTH: 7
<212> TYPE: PRT
<213> ORGANISM: Homo sapiens

<400> SEQUENCE: 15

Lys Asn Asp Arg Gly Asp His
1               5

<210> SEQ ID NO 16
<211> LENGTH: 7
<212> TYPE: PRT
<213> ORGANISM: Mus musculus

<400> SEQUENCE: 16

Lys Asn Asp Met Gly Asp His
1               5

<210> SEQ ID NO 17
<211> LENGTH: 7
<212> TYPE: PRT
<213> ORGANISM: Sus sp.

<400> SEQUENCE: 17

Arg Thr Phe Arg Ile Val Asp
1               5

<210> SEQ ID NO 18
<211> LENGTH: 7
<212> TYPE: PRT
<213> ORGANISM: Bos sp.

<400> SEQUENCE: 18

Lys Asn Asp Arg Gly Asp His
1               5
```

```
<210> SEQ ID NO 19
<211> LENGTH: 8
<212> TYPE: PRT
<213> ORGANISM: Artificial Sequence
<220> FEATURE:
<223> OTHER INFORMATION: Synthetic construct

<400> SEQUENCE: 19

Asp Tyr Lys Asp Asp Asp Asp Lys
1               5

<210> SEQ ID NO 20
<211> LENGTH: 12
<212> TYPE: PRT
<213> ORGANISM: Homo sapiens

<400> SEQUENCE: 20

Gln Tyr Ser Pro Glu Ala Leu Ala Ser Ile Gln Asn
1               5                   10

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 21

His His His His His His
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Tyr Lys Asp Asp Asp Asp Lys
1               5

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Glu Val Asp
1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Glu His Asp
1
```

```
<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Tyr Val Ala Asp
1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Glu Thr Asp
1

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Val Asp Val Ala Asp
1               5

<210> SEQ ID NO 28
<211> LENGTH: 7
<212> TYPE: PRT
<213> ORGANISM: Homo sapiens

<400> SEQUENCE: 28

Met Ala Leu Asp Pro Tyr Thr
1               5

<210> SEQ ID NO 29
<211> LENGTH: 7
<212> TYPE: PRT
<213> ORGANISM: Homo sapiens

<400> SEQUENCE: 29

Gln Pro Leu Arg Lys Tyr Val
1               5

<210> SEQ ID NO 30
<211> LENGTH: 7
<212> TYPE: PRT
<213> ORGANISM: Homo sapiens

<400> SEQUENCE: 30

Pro Ser Asp Phe Asp Gln Leu
1               5

<210> SEQ ID NO 31
<211> LENGTH: 7
<212> TYPE: PRT
```

<213> ORGANISM: Homo sapiens

<400> SEQUENCE: 31

Asp Asp Thr Asp Ser Met Tyr
1               5

<210> SEQ ID NO 32
<211> LENGTH: 7
<212> TYPE: PRT
<213> ORGANISM: Mus musculus

<400> SEQUENCE: 32

Ile Pro Leu Asp Pro Tyr Thr
1               5

<210> SEQ ID NO 33
<211> LENGTH: 7
<212> TYPE: PRT
<213> ORGANISM: Mus musculus

<400> SEQUENCE: 33

Glu Pro Val Arg Lys Tyr Val
1               5

<210> SEQ ID NO 34
<211> LENGTH: 7
<212> TYPE: PRT
<213> ORGANISM: Mus musculus

<400> SEQUENCE: 34

Pro Ser Asp Phe Asp Gln Leu
1               5

<210> SEQ ID NO 35
<211> LENGTH: 7
<212> TYPE: PRT
<213> ORGANISM: Mus musculus

<400> SEQUENCE: 35

Asp Asp Thr Asp Ser Leu Phe
1               5

<210> SEQ ID NO 36
<211> LENGTH: 7
<212> TYPE: PRT
<213> ORGANISM: Sus sp.

<400> SEQUENCE: 36

Gln Pro Leu Arg Lys Tyr Val
1               5

<210> SEQ ID NO 37
<211> LENGTH: 7
<212> TYPE: PRT
<213> ORGANISM: Sus sp.

<400> SEQUENCE: 37

Pro Thr Asp Phe Asp Gln Leu
1               5

<210> SEQ ID NO 38
<211> LENGTH: 7
<212> TYPE: PRT
<213> ORGANISM: Sus sp.

```
<400> SEQUENCE: 38

Asp Asp Thr Asp Ser Met Phe
1               5

<210> SEQ ID NO 39
<211> LENGTH: 7
<212> TYPE: PRT
<213> ORGANISM: Bos sp.

<400> SEQUENCE: 39

Met Ala Leu Asp Pro Tyr Thr
1               5

<210> SEQ ID NO 40
<211> LENGTH: 7
<212> TYPE: PRT
<213> ORGANISM: Bos sp.

<400> SEQUENCE: 40

Gln Pro Leu Arg Lys Tyr Val
1               5

<210> SEQ ID NO 41
<211> LENGTH: 7
<212> TYPE: PRT
<213> ORGANISM: Bos sp.

<400> SEQUENCE: 41

Pro Thr Asp Phe Asp Gln Leu
1               5

<210> SEQ ID NO 42
<211> LENGTH: 7
<212> TYPE: PRT
<213> ORGANISM: Bos sp.

<400> SEQUENCE: 42

Gly Met Thr Asp Ile Met Phe
1               5

<210> SEQ ID NO 43
<211> LENGTH: 7
<212> TYPE: PRT
<213> ORGANISM: Homo sapiens

<400> SEQUENCE: 43

Lys Thr Phe Arg Val Val Asp
1               5

<210> SEQ ID NO 44
<211> LENGTH: 7
<212> TYPE: PRT
<213> ORGANISM: Homo sapiens

<400> SEQUENCE: 44

Lys Glu Leu Ile Arg Met Cys
1               5

<210> SEQ ID NO 45
<211> LENGTH: 7
<212> TYPE: PRT
<213> ORGANISM: Mus Musculus

<400> SEQUENCE: 45
```

```
<210> SEQ ID NO 46
<211> LENGTH: 7
<212> TYPE: PRT
<213> ORGANISM: Mus musculus

<400> SEQUENCE: 46

Lys Glu Leu Ile Arg Leu Cys
1               5

<210> SEQ ID NO 47
<211> LENGTH: 7
<212> TYPE: PRT
<213> ORGANISM: Bos sp.

<400> SEQUENCE: 47

Lys Thr Phe Arg Ile Val Asp
1               5

<210> SEQ ID NO 48
<211> LENGTH: 7
<212> TYPE: PRT
<213> ORGANISM: Bos sp.

<400> SEQUENCE: 48

Lys Glu Leu Ile Arg Met Cys
1               5
```

(Lys Thr Phe Arg Ile Val Asp appears at the top of the page, ending SEQ ID NO 45.)

What is claimed:

1. A method of detecting a polymorphism in an EFHC1 gene in a human subject, comprising:
   (a) providing a biological sample from a human subject, wherein the sample comprises all, or a portion of, an EFHC1 gene;
   (b) contacting one or more labeled oligonucleotide probes under stringent hybridization conditions to the EFHC1 gene or the portion thereof, wherein each oligonucleotide probe is capable of hybridizing to a portion of the EFHC1 gene comprising the 330C>A or 763G>A polymorphism under stringent hybridization conditions but incapable of hybridizing to a portion of the EFHC gene that does not comprise the 330C>A and 763G>A polymorphisms under stringent hybridization conditions, wherein the EFHC1 gene comprises at least 85% sequence identity to SEQ ID NO: 3; and
   (c) detecting hybridization of the one or more labelled oligonucleotides with the EFHC1 gene or the portion thereof under stringent hybridization conditions;
   (d) detecting a polymorphism in an EFHC1 gene in the human subject.

2. The method of claim 1, wherein the probe is between 10 to 40 nucleotides in length.

3. The method of claim 1, wherein the-subject is at risk of juvenile myoclonic epilepsy (JME).

4. The method of claim 1, further comprising amplifying by PCR the EFHC1 gene or the portion thereof.

5. The method of claim 1, wherein the sample comprises neuronal cells.

* * * * *